(12) United States Patent
Li et al.

(10) Patent No.: US 8,501,911 B2
(45) Date of Patent: *Aug. 6, 2013

(54) METHODS OF REDUCING INFLAMMATION AND MUCUS HYPERSECRETION

(75) Inventors: Yuehua Li, Pearland, TX (US); Linda D. Martin, Apex, NC (US); Kenneth B. Adler, Raleigh, NC (US); Shuji Takashi, Nagano (JP); Indu Parikh, Chapel Hill, NC (US)

(73) Assignees: Biomarck Pharmaceuticals, Ltd, Raleigh, NC (US); North Carolina State University, Raleigh, NC (US)

(*) Notice: Subject to any disclaimer, the term of this patent is extended or adjusted under 35 U.S.C. 154(b) by 628 days.

This patent is subject to a terminal disclaimer.

(21) Appl. No.: 11/834,446

(22) Filed: Aug. 6, 2007

(65) Prior Publication Data

US 2009/0220581 A1    Sep. 3, 2009

Related U.S. Application Data

(63) Continuation-in-part of application No. 09/914,020, filed as application No. PCT/US00/05050 on Feb. 24, 2000, now Pat. No. 7,265,088, which is a continuation-in-part of application No. 09/256,154, filed on Feb. 24, 1999, now abandoned, application No. 11/834,446, which is a continuation-in-part of application No. PCT/US2007/005688, filed on Mar. 6, 2007, which is a continuation of application No. 11/367,449, filed on Mar. 6, 2006, now Pat. No. 7,544,772, which is a continuation-in-part of application No. 10/802,644, filed on Mar. 17, 2004, now abandoned, which is a continuation of application No. 10/180,753, filed on Jun. 26, 2002, now abandoned.

(60) Provisional application No. 60/300,933, filed on Jun. 26, 2001.

(51) Int. Cl.
*C07K 7/00*    (2006.01)

(52) U.S. Cl.
USPC .......... 530/326; 530/327; 514/21.4; 514/21.5

(58) Field of Classification Search
USPC ................. 530/324–330; 514/21.4, 21.5
See application file for complete search history.

(56) References Cited

U.S. PATENT DOCUMENTS

| | | |
|---|---|---|
| 4,753,945 A | 6/1988 | Gilbard et al. |
| 4,873,346 A | 10/1989 | Anderson |
| 5,292,498 A | 3/1994 | Boucher |
| 5,298,506 A | 3/1994 | Stamler et al. |
| 5,436,243 A | 7/1995 | Sachs et al. |
| 5,849,706 A | 12/1998 | Molina y Vedia et al. |
| 5,849,719 A | 12/1998 | Carson et al. |
| 5,858,784 A | 1/1999 | Debs et al. |
| 5,858,981 A | 1/1999 | Schreiber et al. |
| 5,861,502 A | 1/1999 | Prockop et al. |
| 6,245,320 B1 | 6/2001 | Kim |
| 6,407,058 B1 | 6/2002 | Staddon et al. |
| 6,506,779 B1 | 1/2003 | Cheng et al. |
| 7,265,088 B1 | 9/2007 | Li et al. |
| 7,919,469 B2 | 4/2011 | Li et al. |
| 2001/0033827 A1 | 10/2001 | Kim |
| 2003/0013652 A1 | 1/2003 | Martin et al. |
| 2004/0180836 A1 | 9/2004 | Martin et al. |
| 2006/0205664 A1 | 9/2006 | Parikh |
| 2006/0217307 A1 | 9/2006 | Takashi et al. |
| 2008/0020031 A1 | 1/2008 | Li et al. |

FOREIGN PATENT DOCUMENTS

| | | |
|---|---|---|
| AU | 766800 | 10/2003 |
| EP | 0 551 200 A1 | 7/1993 |
| EP | 1 154 786 | 8/2000 |
| EP | 1 538 162 A2 | 6/2005 |
| EP | 1 538 162 A3 | 6/2005 |
| JP | 06-502168 A | 3/1994 |
| WO | WO 90/05744 A1 | 5/1990 |
| WO | WO 92/05784 A1 | 4/1992 |
| WO | WO 93/00353 A1 | 1/1993 |
| WO | WO 95/27496 A1 | 10/1995 |
| WO | WO 96/18103 A1 | 6/1996 |
| WO | WO 00/50062 A2 | 8/2000 |
| WO | WO 01/20998 A1 | 3/2001 |
| WO | WO 03/000027 A2 | 1/2003 |
| WO | WO 03/000027 A3 | 5/2003 |
| WO | WO 2006/078899 A2 | 7/2006 |
| WO | WO 2006/078899 A3 | 12/2006 |
| WO | WO 2007/103368 A2 | 9/2007 |

OTHER PUBLICATIONS

Li, Y., (J. Biol. Chem. 276, 40982-40990, 2001).*
Brooks et al., "MARCKS functions as a novel growth suppressor in cells of melanocyte origin," Carcinogenesis 17(4):683-689 (1996).
Seki et al., "Binding of Myristoylated Alanine-Rich Protein Kinase C Substrate to Phosphoinositides Attenuates the Phosphoroylation by Protein Kinase C," Arch. Biochem. Biophys. 326(2):193-201 (1996).
Ito, "Office Action," 6 pages, Japan patent appl. No. 2000-600672, Japan Patent Office (mailed Mar. 24, 2010).
Salvino, Official Action, 4 pages, Canada patent appl. No. 2,366,951, Canadian Intellectual Property Office (Apr. 7, 2009).
Deck, "Communication pursuant to Article 96(2) EPC," 5 pages, Europe patent appl. No. 00912034.6, European Patent Office (Apr. 25, 2002).
Huse, "Communication pursuant to Article 96(2) EPC," 5 pages, Europe patent appl. No. 04024019.4, European Office (Mar. 15, 2007).
Huse, "Communication pursuant to Article 96(2) EPC," 4 pages, Europe patent appl. No. 04024019.4, European Patent Office (Mar. 22, 2006).

(Continued)

*Primary Examiner* — David Lukton
(74) *Attorney, Agent, or Firm* — Cooley LLP

(57) ABSTRACT

Methods and compounds for decreasing MARCKS-related inflammation and MARCKS-related mucus hypersecretion or decreasing MARCKS-related inflammation in a subject by the administration of a N-terminal myristoylated protein fragment of the N-terminal region of MARCKS protein or a peptide fragment thereof are disclosed.

31 Claims, 2 Drawing Sheets

OTHER PUBLICATIONS

Deck, "International Preliminary Examination Report," 6 pages, PCT appl. No. PCT/US00/05050, European patent Office (Nov. 27, 2000).

Epps, "Office Action Summary," 7 pages, U.S. Appl. No. 09/256,154, United States Patent and Trademark Office (mailed Feb. 3, 2000).

Epps-Ford, "Office Action Summary," 11 pages, U.S. Appl. No. 09/914,020, United States Patent and Trademark Office (mailed Mar. 22, 2007).

Epps-Ford, "Office Action Summary," 9 pages, U.S. Appl. No. 09/914,020, United States Patent and Trademark Office (mailed Aug. 28, 2006).

Epps-Ford, "Office Action Summary," 14 pages, U.S. Appl. No. 09/914,020, United States Patent and Trademark Office (mailed Dec. 7, 2005)

Epps-Ford, "Office Action Summary," 11 pages, U.S. Appl. No. 09/914,020, United States Patent and Trademark Office (mailed Jun. 6, 2005).

Epps-Ford, "Office Action Summary," 13 pages, U.S. Appl. No. 09/914,020, United States Patent and Trademark Office (mailed Feb. 23, 2004).

Epps-Smith, "Office Action Summary," 12 pages, U.S. Appl. No. 11/838,589, United States Patent and Trademark Office (mailed Jul. 19, 2010).

Abdullah et al., "P2u purinoceptor regulation of mucin secretion in SPOC1 cells, a goblet cell line from the airways," Biochem. J. vol. 316, 1996, pp. 943-951.

Abdullah et al., "Protein kinase C and Ca2+ activation of mucin secretion in airway goblet cells," Am. Physiol. Soc. 273:L201-L210 (1997).

Aderem, "The MARCKS family of protein kinase-C substrates," Biochem. Soc. Trans. 23:587-591 (1995).

Adler et al., "Effects of inflammatory mediators and drugs on mucus secretion and mucociliary function," Res. Immunol. 149(3):245-248 (1998).

Adler et al., "Hypersecretion of Mucin in Response to inflammatory Mediators by Guinea Piog Tracheal Epithelial Cells In Vitro Is Blocked by Inhibition of Nitric Oxide Synthase," Am. J. Respir. Cell Mol. Biol. 13:526-530 (1995).

Adler et al., "Myristoylated alanine-rich C-kinase substrate protein: A major intracellular regulatory molecule controlling secretion of mucin by human airway goblet cells," Chest 117(5 suppl. 1):266S-267S (2000).

Aigner et al., "Depletion of 43-kD growth associated protein in primary sensory neurons leads to diminished formation and spreading of growth cones," J. Cell Biol. 123(2):417-429 (1993).

Aragona et al., "Effects of a stable analogue pf PGE2 (11-deoxy-13, 14-didehydro-16 (S)-Methylester Methyl PGE2: FCE20700) on the secretory processes of conjunctival goblet cells of rabbit," Exp. Eye Res. 45(5):647-654 (1987).

Barnes, P.J., "Current and future therapies for airway mucus hypersecretion," Novartis Found Symp. 248:237-249 (2002).

Blackshear et al., "The MARCKS family of cellular protein kinase C substrates," J. Biol. Chem. 268(3):1501-1504 (1993).

Bouffard et al., National Center for Biotechnology Information Database, Accession No. G20124. Sep. 28, 1998.

Calle et al., "Glucose-induced phosphorylation of myristoylated alanine-rich C kinase substrate (MARCKS) in isolated rat pancreatic islets," J. Biol. Chem. 267(26):18723-18727 (1992).

Coffey et al., "Glutamate exocytosis and Marcks phosphorylation are enhanced by a metabotopic glutamate receptor coupled to a protein kinase C synergistically activated by diacylglycerol and arachidonic acid," J. Neurochem. 63(4):1303-1310 (1994).

Cross et al., "Antioxidant Protection: A Function of Tracheobronchial and Gastrointestinal Mucus," The Lancet, Jun. 16, 1984, pp. 1328-1329.

Dizier et al., "Genome screen for asthma and related phenotypes in the French EGEA study," American Journal Respiratory and Critical Care Medicine 162:1812-1818 (2000).

Dray-Charier et al., "Regulation of mucin secretion in human gallbladder epithelial cells: Predominant role of calcium and protein kinase C," Gastroenterology 112(3):978-990 (1997).

Driot et al., "Beneficial effects of a retinoic acid analog, CBS-211 A, on an experimental model of keraoconjunctivitis Sicca.," Invest. Opthalmol. Vis. Sci. 33(1):190-195 (1992).

Elzagallaai, A., et al. "Platelet Secretion Induced by Phorbol Esters Stimulation is Mediated Though Phosphorylation of MARCKS: a MARCKS-Derived Peptide Blocks MARCKS Phosphorylation and Serotonin Release without Affecting Pleckstrin Phosphorylation," Hemostatis, Thrombosis, and Vascular Biology. 95(3):894-902. (Feb. 1, 2000).

European Search Report for application No. 02756467.3 dated Sep. 3, 2004.

Fischer et al., "Tumor Necrosis Factor-α Stimulates Mucin Secretion and Cyclic GMP Production by Guinea Pig Tracheal Epithelial Cells In Vitro," Am. J. Respir. Cell Mol. Biol.. vol. 20. 1999, pp. 413-422.

Garcher et al., "CA 19-9 ELISA test: A new method for studying mucus changes in tears," Br. J. Ophthalmol. 82(1):88-90 (1998).

Gipson et al., "Cellular origin of mucins of the ocular surface tear film," Adv. Exp. Med. Biol. 438:221-227 (1998).

Graff et al., "Protein Kinase C Substrate and Inhibitor Characteristics of Peptides Derived from the Myristoylated Alanine-rich C Kinase Substrate (MARCKS) Protein Phosphorylation Site Domain," J. Biol. Chem. 266(22):14390-14398 (1991).

Harlan et al., "The human myristoylated alanine-rich C kinase substrate (MARCKS) gene (MACS)," J. Biol. Chem. 266(22):14399-14405 (1991).

Huse, "Partial European Search Report," 4 pages, from European Patent application No. 04024019.4, European Patent Office, The Hague, The Netherlands (mailed May 3, 2005).

International Search Report corresponding to PCT/US02/22270 mailed on Jan. 22, 2003.

International Search Report for PCT/US03/21963; mailed Sep. 9, 2004.

Kessler et al., "Stimulation of goblet cell mucous secretion by activation of nerves in rat conjunctiva," Curr. Eye Res. 14(11):985-992 (1995).

Kim et al., "Airway goblet cell mucin: its structure and regulation of secretion," Eur. Resp. J. 10(11):2644-2649 (1997).

Kim et al., "Airway Mucus," Eur. Respir. J. vol. 10, 1997, p. 1438.

King et al., "Alteration of Airway Reactivity by Mucus," Respiration Physiology, vol. 62, 1985, pp. 47-59.

Ko et al., "ATP-induced mucin release from cultured airway goblet cells involves, in part, activation of protein kinase C," Am. J. Resp. Cell Mol. Biol. 16:194-198 (1997).

Krunkosky et al., "Effects of TNFα on Expression of ICAM-1 in Human Airway Epithelial Cells In Vitro," Am. J. Respir. Cell Mol. Biol., vol. 22, 2000, pp. 685-692.

Larivee et al., "Platelet-Activating Factor Induces Airway Mucin Release via Activation of Protein Kinase C: Evidence of Translocation of Protein Kinase C to Membranes," Am. J. Respir. Cell Mol. Biol., vol. 11, 1994, pp. 194-205.

Lethem et al., "Nucleotide Regulation of Goblet Cells in Human Airway Epithelial Explants: Normal Exocytosis in Cystic Fibrosis," Am. J. Respir. Cell Mol. Biol., vol. 9, 1993, pp. 315-322.

Li, Y., et al., "MARCKS Protein is a Key Molecule Regulation Mucin Secretion by Human Airway Epithelial Cells in Vitro," The Journal of Biological Chemistry. 276(44):40982-40990. (Nov. 2, 2001).

Linsen et al., "Physiology of the lacrimal system," Bull. Soc. Belge. Ophtalmol. 238:35-44 (1990).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 105:217-226 (1994).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 101:247-256 (1994).

Lu et al., "Regulation of angiotensin II-induced neuromodulation by MARCKS in brain neurons," J. Cell Biol. 142(1):217-227 (1998).

Mastropasqua et al., "Tear deficiency in Fuchs' intermediate uveitis," Can. J. Ophthalmol. 31(1):18-20 (1996).

Murray et al., National Center for Biotechnology Information Database, Accession No. G08525. Feb. 5, 1997.

Murray et al., National Center for Biotechnology Information Database, Accession No. G08539. Feb. 5, 1997.

Myat et al., "Identification of the basolateral targeting determinant of a peripheral membrane protein, MacMARCKS, in polarized cells," Current Biology 8(12):677-683 (1998).

Nakamura et al., "Mucin-like glycoprotein secretion is mediated by cyclic-AMP and protein kinase C signal transduction pathways in rat corneal epithelium," Exp. Eye Res. 66(5):513-519 (1998).

Nichols et al., "Demonstration of the mucous layer of the tear film by electron microscopy," Invest. Ophthalmol. Vis. Sci. 26(4):464-473 (1985).

Prescott et al, "Chronic Mucus Hypersecretion in COPD and Death From Pulmonary Infection," Eur. Respir. J., vol. 8, 1995, pp. 1333-1338.

Ralph, "Conjunctival goblet cell density in normal subjects and in dry eye syndromes," Invest. Ophthalmol. Vis. Sci. 14(4):299-302 (1975).

Raufman et al., "Expression and phosphorylation of a MARCKS-Like Protein in Gastric Chief Cells: Further evidence for modulation of pepsinogen secretion by interaction of $CA^{2+}$/Calmodulin with protein kinase C," J. Cell. Biochem. 64:514-523 (1997).

Rogers, D.F. "Airway Goblet Cell Hyperplasia in Asthma: Hypersecretory and Anti—Inflammatory?" Clinical and Experimental Allergy. Editorial 32: 1124-1127 (2002).

Rogers, D.F., "Pulmonary mucus: Pediatric Perspective," Pediatric Pulmonology 36:178-188 (2003).

Shellans et al., "Conjunctival goblet cell response to vasoconstrictor use," J. Ocul. Pharmacol. 5(3):217-220 (1989).

Singer et al., "A MARCKS-related peptide blocks mucus hypersecretion in a moue model of asthma," Nat. Med. 10:193-196 (2004).

Steiger et al., "Concurrent Increases in the Storage and Release of Mucin-like Molecules by Rat Airway Epithelial Cells in Response to Bacterial Endotoxin," Am. J. Respir. Cell Mol. Biol., vol. 12, 1995, pp. 307-314.

Stein, "International Search Report," 5 pages, from intenational patent application PCT/US00/05050, European Patent Office, Rijswijk, The Netherlands (mailed Sep. 9, 2000).

Stormshak et al., "Dynamics of molecular mechanisms underlying ovarian oxytocin secretion," J. Reprod. Fertil. Suppl. 49:379-390 (1995).

Stumpo et al., "Molecular cloning, characterization, and expression of a cDNA encoding the '80-87-kDA' myristoylated alanine-rich C kinase substrate: A major cellular substrate for protein kinase C," Proc. Natl. Acad. Sci. USA 86:4012-4016 (1989).

Thelen et al., "Regulation by phosphorylation of the reversible association of a myristoylated protein kinase C substrate with the plasma membrane," Nature 351:320-322 (1991).

Thelen et al., "Tumor necrosis factor alpha modifies agonist-dependent responses in human neutrophils by inducing the synthesis and myristoylation of a specific protein kinase C substrate," Proc. Natl. Acad. Sci. USA 87(15):5603-5607 (1990).

Thornton et al., "Identification of Two Glycoforms of the MUC5B Mucin in Human Respiratory Mucus," The Journal of Biological Chemistry, vol. 272, No. 14, Apr. 4, 1997, pp. 9561-9566.

Tseng "Topical tretinoin treatment for severe dry-eye disorders," J. Am. Acad. Dermatol. 15(4 part 2):860-866 (1986).

Vergeres et al., "The myristoyl moiety of myristoylated alanine-rich C kinase substrate (MARCKS) and MARCKS-related protein is embedded in the membrane," J. Biol. Chem. 270(34):19879-19887 (1995).

Vishwanath et al., "Adherence of *Pseudomonas aeruginosa* to Human Tracheobronchial Mucin," Infection and Immunity, vol. 45, No. 1, Jul. 1984, pp. 197-202.

Ward, P.A. and Mulligan M.S., "Blocking of adhesion molecules in vivo as anti-inflammatory therapy." Ther. Immunol. 1(3):165-171 (1994).

Wjst et al., "A genome-wide search for linkage to asthma," Genomics 58:1-8, 1999.

Wright et al., "Oxidant stress stimulates mucin secretion and PLC in airway epithelium via a nitric oxide-dependent mechanism," American J. Physiol., vol. 271, pp. L854-L861 (1996).

Xu et al., "Genomewide screen and identification of gene-gene interactions for asthma-susceptibility in three U.S. populations: Collaborative study on the genetics of asthma," American Journal of Human Genetics. 68:1437-1446 (2001).

Zhao, Y., et al. "Role of MARCKS in regulating endothelial cell proliferation." Am J Physiol Cell Physiol. 279:C1611-C1620. (2000).

Ali et al., "Vasopressin-induced activation of Protein kinase C in renal epithelial cells," Biochim. Biophys. Acta. 1402:188-196 (1998).

McCool et al., "The T84 human colonic adenocarcinoma cell line produces mucin in culture and releases it in response to various secretagogues," Biochem J. 267:491-500 (1990).

Rogers, "Mucus hypersecretion in chronic obstructive pulmonary disease. Chronic Obstructive Pulmonary Disease: Pathogenesis to Treatment," Novartis Foundation. Symposium 234. vol. 234. (2001).

Steel and Hanrahan, "Muscarinic-induced mucin secretin and intracellular signaling by hamster tracheal goblet cells," Am. J. Physiol. Lung Cell Mol. Physiol. 272:230-237 (1997).

* cited by examiner

METHODS OF REDUCING INFLAMMATION AND MUCUS HYPERSECRETION

CROSS REFERENCE TO RELATED APPLICATION

The present application claims priority to as a continuation-in-part to U.S. application Ser. No. 09/914,020 filed on Dec. 31, 2001, now U.S. Pat. No. 7,265,088, issued on Sep. 4, 2007, which claims priority under 35 U.S.C. §371 from PCT Application No.: PCT/US00/05050, filed on Feb. 24, 2000, which claims benefit of U.S. application Ser. No. 09/256,154, now abandoned, filed on Feb. 24, 1999; and the present application further claims priority as a continuation-in-part to PCT Application No.: PCT/US07/05688, filed on Mar. 6, 2007, which claims priority to U.S. application Ser. No. 11/367,449 filed on Mar. 6, 2006, now U.S. Pat. No. 7,544,772, issued on Jun. 9, 2009, which claims priority as a continuation-in-part to U.S. application Ser. No. 10/802,644, now abandoned, filed on Mar. 17, 2004, which claims priority as a continuation to U.S. application Ser. No. 10/180,753, now abandoned, filed on Jun. 26, 2002, which claims priority to U.S. Provisional Application No. 60/300,933, filed Jun. 26, 2001, and all of the disclosures of which are incorporated herein by reference in their entirety.

STATEMENT OF FEDERAL SUPPORT

This invention was made with support in part from the United States Federal government under grant number R01 HL36982 from the National Institutes of Health. The United States government may have certain rights in this invention.

FIELD OF THE INVENTION

The present invention relates to methods of reducing inflammation by modulating cellular secretory processes, and more specifically by modulating the release of inflammatory mediators. The present invention additionally relates to also reducing or decreasing mucus hypersecretion. The present invention also relates to the intracellular signaling mechanism regulating airway mucin hypersecretion as well as illustrating several novel intracellular targets for pharmacological intervention in disorders involving aberrant secretion of respiratory mucins and/or secretion of inflammatory mediators from membrane-bound vesicles or granules in inflammatory cells. The present invention also relates to methods of reducing or decreasing both inflammation and mucus hypersecretion by modulating cellular secretory processes.

BACKGROUND OF THE INVENTION

Mucus is a biological liquid that is capable of forming gels. It is a mixture of components, including water and secretory products from a variety of cells. Expectorated human airway mucus contains approximately 95% water and 5% solids; the solids contents include 2-3% proteins and glycoproteins, 1% lipids, and 1% minerals. See Boat et al., *Biochemistry of Mucus*, In: *Airway Secretion*, Takashima and Shimura (eds.), Marcel Dekker, 1994. Mucins, also called mucous glycoproteins or epithelial glycoproteins, are glycoconjugates characterized by numerous oligosaccharide side chains linked to a peptide core by N- and O-linkages.

In the airways, mucins are released onto the airway surface from goblet cells on the surface epithelium, and from mucus cells of submucosal glands. The total amount of surface liquid (mucus) in the airways is the result of the rate of mucus secretion in conjunction with the rate of clearance of mucus (by epithelial reabsorption, evaporation, ciliary transport, and cough transport). Under "normal" conditions, the rate of secretion and clearance of mucus are balanced so that only a thin surface layer of liquid covers the tracheobronchial tree. Mucus hypersecretion (if not accompanied by a concomitant increase in mucus clearance) results in accumulation of airway mucus, which can result in airflow obstruction and increased retention of inhaled particulate matter and microbial matter. Existing strategies to reduce luminal mucus in the airways include inhibition of mucus hypersecretion using indirect pharmacological action, changing the physical characteristics of mucus to enhance ciliary action, and enhancement of cough clearance of mucus.

Hypersecretion of mucus contributes to the pathogenesis of a large number of airway inflammatory diseases in both human and non-human animals. Increased mucus secretion is seen in chronic disease states such as asthma, chronic obstructive pulmonary disease (COPD) and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza or the common cold. Accordingly, new methods and therapeutic compounds able to decrease or lessen mucus secretion are desirable.

Accompanying hypersecretion of mucus in many of these respiratory diseases is the constant presence of inflammatory cells in the airways. These cells contribute greatly to the pathology of these diseases via the tissue damage done by the inflammatory mediators released from these cells. One example of such damage and destruction via this chronic inflammation occurs in cystic fibrosis patients where mediators released from neutrophils (e.g. myeloperoxidase) induce the desquamation of the airway epithelial tissue.

Mammalian airways are lined by a thin layer of mucus produced and secreted by airway epithelial (goblet) cells and submucosal glands. In diseases such as asthma, chronic bronchitis, and cystic fibrosis, hypersecretion of mucus is a common lesion. Excess mucus can contribute to obstruction, susceptibility to infection, and even to destruction of airway walls and contiguous tissues. The major components of mucus are mucin glycoproteins synthesized by secretory cells and stored within cytoplasmic membrane-bound granules. Mucins are a family of glycoproteins secreted by the epithelial cells including those at the respiratory, gastrointestinal and female reproductive tracts. Mucins are responsible for the viscoelastic properties of mucus and at least eight mucin genes are known. Thornton, et al., J. Biol. Chem. 272, 9561-9566 (1997). Mucociliary impairment caused by mucin hypersecretion and/or mucus cell hyperplasia leads to airway mucus plugging that promotes chronic infection, airflow obstruction and sometimes death. Many airway diseases such chronic bronchitis, COPD, bronchiectacis, asthma, cystic fibrosis and bacterial infections are characterized by mucin overproduction. E. Prescott, et al., Eur. Respir. J., 8:1333-1338 (1995); K. C. Kim, et al., Eur. Respir. J., 10:1438 (1997); D. Steiger, et al. Am. J. Respir. Cell Mol. Biol., 12:307-314 (1995). Upon appropriate stimulation, mucin granules are released via an exocytotic process in which the granules translocate to the cell periphery where the granule membranes fuse with the plasma membrane, allowing for luminal secretion of the contents.

Despite the obvious pathophysiological importance of this process, intracellular signaling mechanisms linking stimulation at the cell surface to mucin granule release has only recently been elucidated. See, Li et al., Journal of Biological Chemistry, 276: 40982-40990 (2001). It is known that a wide variety of agents and inflammatory/humoral mediators provoke mucin secretion. These include cholinergic agonists, lipid mediators, oxidants, cytokines, neuropeptides, ATP and UTP, bacterial products, neutrophil elastase, and inhaled pollutants. See, Adler et al., Res. Immunol. 149, 245-248 (1998). Interestingly, many of these mucin secretagogues are also known to activate several protein kinases, and studies examining the regulation of excess secretion of mucin by airway epithelial cells from various species have consistently implicated involvement of either protein kinase C (PKC) or cGMP-dependent protein kinase (PKG) in the secretory process. See, e.g., Ko et al., Am. J. Respir. Cell Mol. Biol. 16, 194-198 (1997): Abdullah et al. Am. J. Physiol. 273, L201-L210 (1997); Abdullah et al., Biochem. J. 316, 943-954 (1996); Larivee et al. Am. J. Respir. Cell Mol. Biol. 11, 199-205 (1994); and Fischer et al., Am. J. Respir. Cell Mol. Biol. 20, 413-422 (1999). Coordinated interactions or "cross-talk" between these two protein kinases in regulation of mucin secretion has only recently been demonstrated to involve the MARCKS proteins. See, Li et al., Journal of Biological Chemistry, 276: 40982-40990 (2001). However, signaling events downstream of the coordinated action of these protein kinases that ultimately lead to the exocytotic release of mucin granules have not been fully elucidated. Interestingly, similar experimentation examining release of inflammatory mediators from neutrophils suggests that a similar pathway of kinase "cross-talk" regulates secretion in these inflammatory cells; thus suggesting the potential universality of secretory mechanisms that involve multiple kinases, in particular PKC and PKG.

Previously, procedures to culture normal human bronchial epithelial (NHBE) cells in an air/liquid interface system in which the cells differentiate to a heterogeneous population containing secretory (goblet), ciliated, and basal cells that mimic their in vivo appearance and function was reported. Krunkosky et al., Am. J. Respir. Cell Mol. Biol. 22, 685-692 (2000). These cell cultures may provide an in vitro model system to study mechanisms regulating mucin secretion from human airway epithelium. Yet, there is a need in the field to understand the mechanisms regulating mucin secretion from human airway epithelium cells and to develop methods of regulating mucin secretion and to improve upon anti-inflammatory therapy. Further efforts to elucidate mechanisms responsible for secretion of inflammatory mediators from inflammatory cells may also lead to the ability to inhibit both types of secretion (mucus and inflammatory mediators) via targeting an intracellular molecule or event common to both types of secretory pathways.

MARCKS, a protein of approximately 82 kD, has three evolutionarily-conserved regions (Aderem et al., Nature 1988; 332:362-364; Thelen et al., Nature 1991; 351:320-322; Hartwig et al., Nature 1992; 356:618-622; Seykora et al., J Biol Chem 1996; 271:18797-18802): an N-terminus, a phosphorylation site domain (PSD), and a multiple homology 2 (MH2) domain. The N-terminus, a 24 amino acid sequence with a myristic acid moiety attached to a terminal glycine residue via an amide bond is involved in binding of MARCKS to membranes (Seykora et al., J Biol Chem 1996; 271:18797-18802) and possibly to calmodulin (Matsubara et al., J Biol Chem 2003; 278:48898-48902). This 24 amino acid sequence is known as the MANS peptide. The MANS peptide and active fragments thereof, can compete with native MARCKS in cells for membrane binding.

Involvement of MARCKS protein in release of inflammatory mediators from the granules of infiltrating leukocytes is relevant to inflammation in diseases in all tissues and organs, including lung diseases characterized by airway inflammation, such as asthma, COPD and cystic fibrosis. However, inflammation and mucus secretion in the airways are two separate and independent processes (Li et al., J Biol Chem 2001; 276:40982-40990; Singer et al., Nat Med 2004; 10:193-196). While mucus production and secretion can be provoked by a number of factors, including mediators released by inflammatory cells, there is no known link between excess mucus and inflammation which leads directly to inflammation.

In view of the foregoing, methods and compositions are disclosed that are able to decrease or reduce inflammation, or that are able to decrease or reduce both inflammation and mucus hypersecretion, by the administration of a peptide or a composition containing the peptide that inhibits the MARCKS protein-mediated release of inflammatory mediators and/or mucus from granules inside inflammatory cells and/or inside a mucus-secreting cell.

SUMMARY OF THE INVENTION

The invention relates to a method of decreasing MARCKS-related mucus secretion and MARCKS-related inflammation secretory processes in cells and tissues of a subject in need of such treatment comprising administration to a subject a pharmaceutical composition comprising a N-terminal myristoylated protein fragment of the N-terminal region of MARCKS protein, in a dual function therapeutically effective amount to reduce MARCKS-related secretion of at least one inflammatory mediator from at least one inflammatory cell in the subject and to reduce MARCKS-related mucus hypersecretion from at least one mucus secreting cell or tissue, whereby inflammation and mucus hypersecretion in the subject are reduced compared to that which would occur in the absence of said administration of the pharmaceutical composition.

The invention also relates to a method of decreasing MARCKS-related inflammation secretory processes in cells and tissues of a subject in need of such treatment comprising: administration to the subject a pharmaceutical composition comprising a N-terminal myristoylated protein fragment of the N-terminal region of MARCKS protein, in a therapeutically effective amount to reduce MARCKS-related secretion of at least one inflammatory mediator from at least one inflammatory cell or tissue in the subject or tissue, whereby inflammation in the subject is reduced compared to that which would occur in the absence of said administration of the pharmaceutical composition.

The invention relates to a new use for a N-terminal myristoylated protein fragment of the N-terminal region of MARCKS protein, the 24 amino acid, myristoylated polypeptide, also known as the MANS peptide, and for active peptide fragments thereof.

The invention also relates to a new method for blocking any cellular secretory process, especially those that involve the release of inflammatory mediators from inflammatory cells, whose stimulatory pathways involve the protein kinase C (PKC) substrate MARCKS protein and release of contents from intracellular vesicles or granules.

The present invention is directed to a method of inhibiting the exocytotic release of at least one inflammatory mediator from at least one inflammatory cell comprising contacting the at least one inflammatory cell, which cell comprises at least one inflammatory mediator contained within a vesicle inside the cell, with at least one peptide selected from the group consisting of a MANS peptide and an active fragment thereof in an effective amount to reduce the release of the inflammatory mediator from the inflammatory cell as compared to the release of the inflammatory mediator from the same type of inflammatory cell that would occur in the absence of the at least one peptide.

The present invention also relates to a method of reducing inflammation in a subject. More specifically, the method comprises blocking or reducing certain cellular secretory processes, such as those that involve the release of inflammatory mediators from inflammatory cells, whose stimulatory pathways involve the protein kinase C (PKC) substrate MARCKS protein and release of contents (i.e., MARCKS-related release) from membrane-bound vesicles.

The present invention also relates to a method of reducing inflammation in a subject comprising the administration of a therapeutically effective amount of a pharmaceutical composition comprising a MANS peptide (a 24 amino acid, N-terminal myristoylated peptide of the MARCKS protein, SEQ ID NO: 1) or an active fragment thereof.

The present invention is further directed to a method of inhibiting the release of at least one inflammatory mediator from at least one inflammatory cell in a tissue or fluid of a subject comprising the administration to the subject's tissue and/or fluid, which comprises at least one inflammatory cell comprising at least one inflammatory mediator contained within a vesicle inside the cell, a therapeutically effective amount of a pharmaceutical composition comprising at least one peptide selected from the group consisting of a MANS peptide and an active fragment thereof in a therapeutically effective amount to reduce the release of the inflammatory mediator from at least one inflammatory cell as compared to release of the inflammatory mediator from at least one of the same type of inflammatory cell that would occur in the absence of the at least one peptide. More specifically, inhibiting the release of an inflammatory mediator comprises blocking or reducing the release of an inflammatory mediator from the inflammatory cell, and more specifically, blocking or reducing the release of an inflammatory mediator from a granule inside the inflammatory cell.

The present invention also includes a method for regulating a cellular secretory process in a subject comprising the administration to a site of inflammation in the subject of a therapeutically effective amount of a compound comprising a MANS peptide or an active fragment thereof, effective to modulate secretory release of an inflammatory mediator from an inflammatory cell in the subject at the inflammation site.

Further, the present invention includes methods of reducing an inflammation at a tissue site in a subject comprising administering a therapeutically effective amount of a compound that inhibits the MARCKS-related release of an inflammatory mediator from a cell at a tissue site of a subject, whereby the inflammation in the tissue of the subject is reduced compared to that which would occur in the absence of said treatment.

The present invention also includes a method for reducing inflammation and mucus hypersecretion in a subject comprising the administration of a therapeutically effective amount of a compound that inhibits the MARCKS-related release of an inflammatory mediator and MARCKS-related release of mucus, whereby inflammation and mucus secretion in the subject are reduced compared to that which would occur in the absence of said treatment. Additionally, both the inflammation and mucus secretion may be reduced simultaneously. The term simultaneously means that both inflammation and mucus secretion are reduced at the same time (or concomitantly).

The present invention also discloses methods of reducing or inhibiting inflammation at a tissue site in a subject comprising the administration (to the tissue site) of a therapeutically effective amount of a MANS peptide or an active fragment thereof effective to modulate release of an inflammatory mediator from an inflammatory cell at the inflammation site.

More particularly, the present invention includes a method of reducing inflammation in a subject comprising the administration of a therapeutically effective amount of a pharmaceutical composition comprising a MANS peptide [i.e., N-myristoyl-GAQFSKTAAKGEAAAERPGEAAVA (SEQ ID NO: 1)] or an active fragment thereof. In one aspect, an active fragment comprises the first six amino acid sequence of the MANS peptide which is myristoylated by an amide bond at the N-terminal amine of the peptide. Thus, in one aspect, an active fragment of the MANS peptide comprises the myristoylated sequence: N-myristoyl-GAQFSK (SEQ ID NO: 19), wherein the active fragment is at least six amino acids in length.

The MANS peptide or an active fragment useful in the present invention to reduce MARCKS-related mucus secretion and MARCKS-related inflammation comprises at least one myristoylated N-terminal peptide fragment of MANS (SEQ ID NO: 1) which comprises at least five or at least six amino acids, wherein the first, or N-terminal, amino acid of said fragment begins at the N-terminal glycine of SEQ ID NO: 1 (MANS peptide). More specifically, an active fragment can be selected from the group consisting of N-myristoyl-GAQFSKTAAKGEAAAERPGEAAV (SEQ ID NO: 2); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAER-PGE (SEQ ID NO: 5); N-myristoyl-GAQFSK-TAAKGEAAAERPG (SEQ ID NO: 6); N-myristoyl-GAQF-SKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); N-myristoyl-GAQFSK (SEQ ID NO: 19); and N-myristoyl-GAQFS (SEQ ID NO: 20). These fragments of the MANS peptide are therefore also N-terminal fragments of the MARCKS peptide.

In another aspect, this invention discloses a pharmaceutical composition of the MANS peptide, or an active fragment thereof, which is useful to block inflammation and which is useful to decrease mucin hypersecretion.

The present invention also includes methods for regulating a cellular secretory process, wherein the secretory process comprises secretion from a vesicle or granule, in a subject comprising the administration of a therapeutically effective amount of a compound comprising a MANS peptide or an active fragment thereof, which regulates release of an inflammatory mediator in a subject. In this aspect, the administration is selected from the group consisting of topical administration, parenteral administration, rectal administration, pulmonary administration, inhalation administration, nasal administration, and oral administration, wherein pulmonary administration generally comprises use of an aerosol, such as produced from a dry powder inhaler, from a metered dose inhaler, or from a nebulizer.

The present invention also includes methods of reducing inflammation in a subject comprising the administration of a therapeutically effective amount of a compound that inhibits the MARCKS-related release of at least one inflammatory mediator, whereby the release of at the least one inflammatory mediator in the subject is reduced compared to that which would occur in the absence of said administration.

The present invention further includes methods of reducing inflammation in a subject comprising administering a therapeutically effective amount of a compound that inhibits the MARCKS-related release of inflammatory mediators, whereby the inflammation in the subject is reduced as compared to that which would occur in the absence of said treatment or administration (for administering). The present invention also discloses methods of reducing or inhibiting inflammation in a subject comprising the administration of a therapeutically effective amount of a MANS peptide or an active fragment thereof effective to modulate (reduce) release from a granule in an inflammatory cell of an inflammatory mediator at the inflammation site.

The present invention further relates to MANS peptide and active fragments thereof that can be useful in the prevention or reduction in amount of inflammation in a tissue in an animal caused by inflammatory mediators. MANS peptide and active fragments thereof can also be useful in the prevention or reduction in amount of tissue damage in an animal produced or caused by inflammatory mediators.

In another aspect, the present invention is also a method of inhibiting mucus secretion by a mucus-secreting cell, by administering to the cell a mucus-inhibitory amount of a compound that inhibits MARCKS protein-related mucus secretion.

BRIEF DESCRIPTION OF THE DRAWINGS

In another aspect.

DETAILED DESCRIPTION OF PREFERRED EMBODIMENTS

Figure 1:
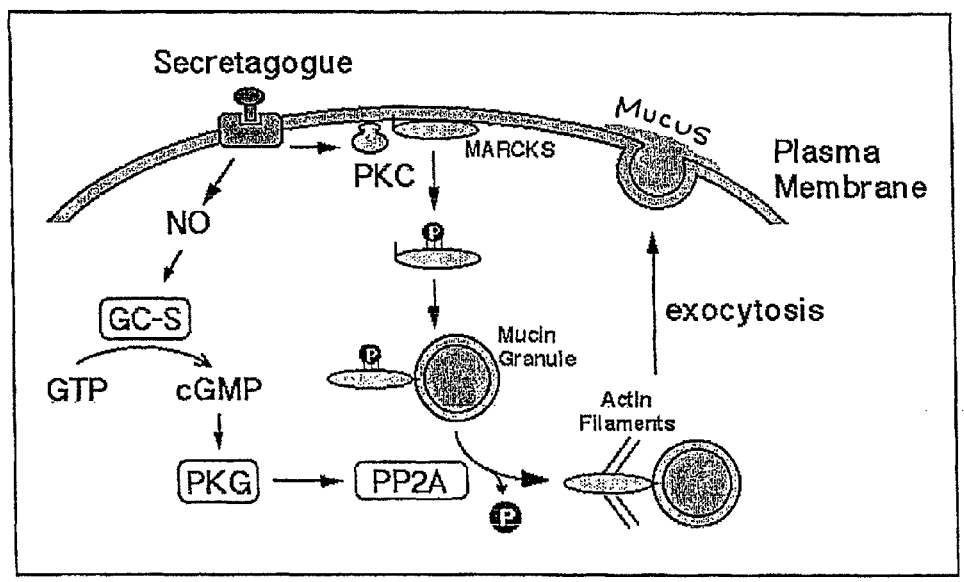
FIG. 1 is an illustration of a proposed signaling pathway of MARCKS-mediated mucin secretion by human epithelial cells. In this Figure, PKC=protein kinase C; PKG=cGMP-dependent protein kinase; GC-S=soluble guanylyl cyclase; PP2A=protein phosphatase 2A; NO=nitric oxide; GTP=guanosine triphosphate; and cGMP=cyclic guanosine monophosphate. In this proposed pathway, mucin secretagogues (shown in FIG. 1 as binding to a receptor) interact with airway epithelial (goblet) cells and activate two separate protein kinases: PKC and PKG. Activated PKC phosphorylates MARCKS, causing its translocation from the plasma membrane to the cytoplasm, where it is targeted to the mucin granule membrane with the assistance of MARCKS-associated proteins. PKG, activated via the nitric oxide (NO)-cGMP-PKG pathway, in turn activates a cytoplasmic protein phosphatase 2A (PP2A), which dephosphorylates MARCKS, thus stabilizing its attachment to the granule membrane and allowing MARCKS to cross-link actin filaments. This tethers the granule to the cytoskeleton for movement and exocytosis.

The present invention will now be described more fully hereinafter with reference to the accompanying figures, in which preferred embodiments of the invention are illustrated. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. The use of the words "a" or "an" herein to describe any aspect of the present invention is to be interpreted as indicating one or more.

Mucus is the clear viscous secretion of the mucous membranes, and comprises water, mucin, lipids, and various inorganic salts. Mucin is a carbohydrate-rich glycoprotein that is secreted by specialized epithelial cells (known as goblet cells), the submaxillary glands, and other mucous glandular cells. Goblet cells are epithelial cells specialized for secretion and containing an accumulation of mucous secretory granules.

Mucous tissue (or mucosa) lines various anatomic structures in the mammalian and avian body, including the eyes, respiratory tract (alveoli, bronchi, oral cavity, larynx, nasal cavity, pharynx, trachea), gastrointestinal tract (esophagus, stomach, small and large intestine, rectum), and genitourinary tract (urethra, urinary bladder, uterus and vagina).

Alterations in the quantity of mucus secretions may be due to various underlying factors, including a change in the amount of mucous glycoproteins secreted from mucus-secreting cells, a change in the total number of mucus-secreting cells, or combinations thereof. Mediators released by the inflammatory response are known to act as mucus secretagogues, including lipid mediators, oxygen metabolites, and other cell-specific products. Larivee et al., In: *Airway Secretion*, Takishima and Shimura (Eds.), Marcel Dekker Inc., 1994, pages 469-511.

The present invention recognizes that the compounds and methods of the present invention are useful to decrease, reduce or block the secretion of inflammatory mediators from inflammatory cells, such as macrophages, neutrophils and others. The methods and compositions of the present invention also are useful to inhibit or reduce (decrease) mucus secretion occurring from any mucus-secreting cell (such as goblet cells) or tissue (such as mucous membranes of the airways). In this way, the compounds of the present invention possess a dual function of decreasing mucus secretion (including decreasing release of mucin) and decreasing inflammation (including decreasing release of inflammatory mediators from inflammatory cells).

The present invention relates to methods for regulating (attenuating) cellular and granular secretory processes, especially those releasing inflammatory mediators from inflammatory cells and releasing mucus from mucus-secreting cells. As used herein, the term "regulating" means blocking, inhibiting, decreasing, reducing or attenuating. As used herein "reducing" generally means a lessening of the effects of inflammation. Preferably, release of inflammatory mediators is inhibited or blocked or attenuated by the methods disclosed.

Also as used herein, the term "inhibiting" means a reduction in the amount of inflammatory mediator secretion. The term "completely inhibiting" means a reduction to zero in the amount of inflammatory mediator secretion.

The term "exocytotic process" means exocytosis, i.e., a process of cellular secretion or excretion in which substances contained in a vesicle (or granule), which vesicle resides inside a cell, are discharged from the cell by fusion of the vesicular membrane of the vesicle with the outer cell membrane. "Degranulation" means the release of cellular granule contents. The term "degranulation-inhibiting" means a reduction in the release of inflammatory mediator contained within the granules of the inflammatory cell. Thus, a degranulation-inhibiting amount of the MANS peptide or an active fragment thereof is the amount of the peptide that is sufficient to reduce the release of an inflammatory mediator contained in the granules as compared to release in the absence of the same peptide.

Further as used herein, the term "modulate" encompasses both "increase" or "decrease", but with respect to MANS peptide and to active fragments thereof and their effect on release of inflammatory mediators and on release of mucus from granules in cells, "modulate" is intended to mean "decrease".

As used herein, "hypersecretion" of mucus refers to production of mucus above a normal or basal amount, or production of mucus in an above-normal amount that leads to pathological changes or symptoms. As used herein, the "inhibiting mucus secretion" refers to a lessening or reduction in mucus secretion; it is not meant to imply the complete cessation of mucus secretion. A treatment that inhibits mucus secretion results in decreased mucus production compared to that which would occur, or would be expected, in the absence of such treatment. Amounts of mucus secreted by a cell in culture, or by a tissue in vivo can be measured or assessed using methods as are known in the art. As used herein, "stimulated mucus secretion" refers to mucus secretion that occurs in response to a secretagogue; this is contrasted to "basal mucus secretion" that occurs under normal physiological conditions.

A "mucus inhibitory" or "mucus inhibiting" amount of a compound is that amount which reduces or inhibits mucus secretion, compared to that which would occur in the absence of the compound. The most effective amount of a particular peptide will vary depending upon the peptide, route of administration, and condition being treated. As used herein, the term "compound" is to be broadly construed to include proteins, peptide fragments, nucleotides, oligonucleotides, and other non-protein chemicals.

A number of cellular secretory processes involve the release of contents from membrane-bound (i.e., membrane-surrounded) vesicles or granules within cells. A membrane-bound vesicle or granule is defined as an intracellular particle, which is primarily vesicular (or a vesicle inside a cell) and which contains stored material that can be secreted, such as mucin in one aspect and an inflammatory mediator in another aspect. Some of the contents of these vesicles, such as those vesicles contained in inflammatory cells, upon secretion have been found to be responsible for a variety of pathologies in numerous mammalian tissues. Some of the effects of these secretions appear to include damage of previously healthy tissue during inflammation. This invention provides a means of blocking secretion from membrane-bound vesicles or granules, including those found in inflammatory cells, by targeting a specific molecule important in the intracellular secretory pathway with a synthetic peptide. This approach may be of therapeutic importance for the treatment of a wide variety of hypersecretory and inflammatory conditions in humans and animals.

In one aspect, the present invention targets inflammatory cells that contain the inflammatory mediators in one or more granules or vesicles within each cell's cytoplasm. The cells are contacted (treated) with one or more peptides that are selected from the group consisting of the MANS peptide and an active fragment thereof, all of which are described in detail herein. Preferably the contact (treatment) of the inflammatory cell with the peptide is via administration to a subject afflicted by or suffering from a disease in which these inflammatory cells are present in specific tissue or fluid within the tissue. Upon administration or contact of the peptide with the cell, the peptide competes for and competitively inhibits the binding of the native MARCKS protein to the membrane of the intracellular granules or vesicles which contain the inflammatory mediators. As a result of blocking the binding of the MARCKS protein to the vesicles in the inflammatory cells, these vesicles in these cells do not move to the plasma membrane of the cells as they would normally do when stimulated to exocytotically release their contents of inflammatory mediators out of the cells. Thus, the method of the present invention inhibits the movement of the vesicles to the cells' plasma membrane, which in turn, reduces the release of the inflammatory mediators from the inflammatory cells. The amount of inflammatory mediators released from the cells over time is reduced because both the rate of release and the amount of release of the mediators from the inflammatory cells is dependent upon the concentration of the peptide administered and contacted with the inflammatory cells.

A benefit of the present invention is that it may combine a therapy that includes the direct blocking (attenuation) of mucus secretion (e.g., a reduction of mucus hypersecretion) with a unique anti-inflammatory therapy. A benefit of the present invention over current anti-inflammation therapies that affect a general suppression of the immune system is that the peptide is thought to block secretion of only membrane-bound (i.e., membrane-contained or vesiculated) components secreted from inflammatory cells. Thus, many aspects of the immune system should still function without the release of a number of damaging agents.

A method of the present invention includes a method of decreasing or inhibiting or reducing MARCKS-related mucus secretion and MARCKS-related inflammation secretory processes in cells and tissues of a subject in need of such treatment comprises the administration to the subject a pharmaceutical composition comprising a N-terminal myristoylated protein fragment of the N-terminal region of MARCKS protein, in a dual function therapeutically effective amount to reduce MARCKS-related secretion of at least one inflammatory mediator from at least one inflammatory cell in the subject and to reduce MARCKS-related mucus hypersecretion from at least one mucus secreting cell or tissue in the subject, whereby inflammation and mucus hypersecretion in the subject are reduced compared to that which would occur in the absence of said administration of the pharmaceutical composition.

A method of the present invention can also include a method of only decreasing or inhibiting or reducing the MARCKS-related secretory process in inflammatory cells of a subject in need of such treatment comprising: administration to said subject a pharmaceutical composition comprising a N-terminal myristoylated protein fragment of the N-terminal region of MARCKS protein, in a therapeutically effective amount to reduce MARCKS-related release of at least one inflammatory mediator from at least one inflammatory cell in the subject, whereby inflammation in the subject is reduced compared to that which would occur in the absence of said administration of the pharmaceutical composition.

Both of the methods described above for decreasing the MARCKS-related secretory process of inflammatory cells alone or MARCKS-releated secretory process of inflammatory cells and mucus secreting cells include the administration of a N-terminal myristoylated protein fragment of the N-terminal region of MARCKS protein that consists of the myristoylated N-terminal peptide (SEQ ID NO:1) or a N-terminal myristoylated peptide fiagment thereof consisting of at least five contiguous amino acids of SEQ ID NO: 1. The N-terminal myristoylated peptide fragment may alternatively consist of at least amino acids, at least 15 amino acids or at least 20 amino acids of SEQ ID NO: 1.

The N-terminal myristoylated protein fragment may further be selected from the group consisting of N-myristoyl-GAQFSKTAAKGEAAAERPGEAAVA (SEQ ID NO: 1); N-myristoyl-GAQFSKTAAKGEAAAERPGEAAV (SEQ ID NO: 2); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16): N-myristoyl-GAQFSKTA (SEQ ID NO: 17); N-myristoyl-GAQFSKT (SEQ ID NO: 18); N-myristoyl-GAQFSK (SEQ ID NO: 19); and N-myristoyl-GAQFS (SEQ ID NO: 20). The pharmaceutical composition administered by these methods may comprise a combination of the above-identified N-terminal myristoylated peptide fragments for administration. Preferably, the pharmaceutical composition comprises a combination of two of the N-terminal myristoylated peptide fragments but combinations of three or four N-terminal myristoylated peptide fragments may also be administered if such administration results in the desired reduction of the MARCKS-related secretory process of inflammatory cells and mucus secreting cells in the subject treated as compared to no treatment or treatment with only one of the N-terminal myristoylated peptide fragments.

The inflammatory mediator is secreted from an infiltrating inflammatory cell at a site of inflammation in the subject. The mucus secreting cell is an epithelial cell in the airways of the subject. The inflammation and mucus hypersecretion that the subject is afflicted with are caused by or are the clinical symptoms of a respiratory disease. Examples of respiratory diseases that could cause such clinical symptoms include asthma, chronic bronchitis, chronic obstructive pulmonary disease (COPD), bronchiectasis, emphysema, pneumonia, influenza, rhinitis the common cold, or a combination thereof. The subject that is treated is preferably a mammal and more preferably a human. Additionally, the inflammation and mucus hypersecretion that the subject is afflicted with may be caused by or are the clinical symptoms of inflammatory bowel diseases or digestive disorders.

The inflammation treated by the method of the administration of a pharmaceutical composition comprising a N-terminal myristoylated protein fragment of the N-terminal region of MARCKS protein may be caused by or is a major clinical symptom of a bowel disease, a skin disease, an autoimmune disease or a pain syndrome. This clinical symptom of inflammation may be caused by or is a clinical symptom of arthritis, ulcerative colitis, multiple sclerosis, Guillain-Barre syndrome, Crohn's disease, irritable bowel syndrome, psoriasis, rosacea, eczema, psoriasis, severe acne, systemic lupus erythematosus or insulin-dependent diabetes mellitus.

The administration of the pharmaceutical composition may be by any known route but preferably by topical administration, parenteral administration, rectal administration, pulmonary administration, inhalation administration, nasal administration, and oral administration. The pulmonary administration includes the use of an aerosol, such as produced from a dry powder inhaler, from a metered dose inhaler, or from a nebulizer. The therapeutically effective amount of the pharmaceutical composition is administered orally, parenterally, rectally, or through an air passage.

The inflammatory cell that releases the inflammatory mediator from a granule may be a leukocyte, especially a granulocyte, such as a neutrophil, a basophil, an eosinophil, a monocyte, a macrophage, or a mast cell.

The method also may include the administration to the subject of a second molecule selected from the group consisting of an antibiotic, an antiviral compound, an antiparasitic compound, an anti-inflammatory compound, and an immunosuppressant.

The method of decreasing or inhibiting or reducing MARCKS-related mucus secretion and MARCKS-related inflammation secretory processes in cells and tissues of a subject in need of such treatment alternatively includes the administration of a pharmaceutical composition comprising an antisense oligonucleotide that hybridizes to nucleotide molecules encoding a MARCKS protein or an active fragment thereof, wherein said oligonucleotide inhibits expression of said MARCKS protein when administered to said cells in said subject. The antisense oligonucleotide is at least eighteen nucleotides in length. The antisense oligonucleotide may be introduced into the subject in a liposome.

The above described methods of inhibiting the MARCKS-related secretory process in inflammatory cells and in mucus secreting cells or inflammatory cells alone apply to inhibiting this MARCKS-related release for both types of cells or only inflammatory cells to treat the clinical symptoms caused by the release of inflammatory mediators and mucus in subject(s) afflicted with the diseases disclosed herein.

The compounds of the invention may regulate, i.e. block or decrease (attenuate) inflammatory mediator release from cells. This inhibition (truncation, attenuation) of inflammatory mediator release and consequent inhibition (truncation, attenuation) of inflammation is an attractive means for treating subjects suffering from a variety of disorders, e.g., diseases and pathological conditions involving inflammation, including diseases where mucus hypersecretion obtains. Thus, the compounds of the invention may be useful for the treatment of inflammation and also of mucus hypersecretion in such diseases and conditions. These encompass airway inflammatory diseases including such chronic diseases as asthma, COPD and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza, sinusitis or the common cold. Compounds of the invention may also be useful for the treatment of inflammation in chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat or alleviate inflammatory symptoms in other disorders associated with the activity of elevated levels of proinflammatory enzymes, such as responses to various infectious agents and a number of diseases of autoimmunity such as rheumatoid arthritis, toxic shock syndrome, diabetes and inflammatory bowel diseases.

Uses of the peptides and methods of the invention include therapies to combat or attenuate (reduce) inflammation along with therapies that will combine the anti-inflammatory activity of the peptide with its ability to block or attenuate (reduce) mucus hypersecretion. Diseases that may be treated by the peptide's ability to attenuate release of inflammatory mediators to block (reduce) inflammation and to attenuate release of mucus to block (reduce) mucus hypersecretion include but are not limited to inflammatory bowel diseases, digestive disorders (e.g., inflamed gall bladder, Menetier's disease) and inflammatory airway diseases. The peptide may also be used to block or attenuate (reduce) release of excess insulin from pancreatic islet cells.

Other proinflammatory mediators have been correlated with a variety of disease states that correlate with influx of neutrophils into sites of inflammation or injury. Blocking antibodies have been demonstrated as useful therapies in the neutrophil-associated tissue injury in acute inflammation (Harada et al., 1996, Molecular Medicine Today 2, 482). Other cells that may release inflammatory mediators include basophils, eosinophils, granular leukocytes, monocytes and lymphocytes; and therapies to prevent or reduce tissue injury may be directed against secretion of inflammatory mediators (especially membrane-contained or vesiculated mediators) from these cells.

Neutrophils, eosinophils, and basophils are each a type of granulocyte, i.e., a leukocyte that has granules in its cytoplasm. Leukocytes synthesize a number of inflammatory mediators that are packaged and stored in cytoplasmic granules. Among these mediators are, for example, myeloperoxidase [MPO] in neutrophils (Borregaard N, Cowland J B. Granules of the human neutrophilic polymorphonuclear leukocyte. Blood 1997; 89:3503-3521), eosinophil peroxidase [EPO] and major basic protein [MBP] in eaosinophils (Gleich G J. Mechanisms of eosinophil-associated inflammation. J Allergy Clin Immunol 2000; 105:651-663), lysozyme in monocytes/macrophages (Hoff T, Spencker T, Emmendoerffer A., Goppelt-Struebe M. Effects of glucocorticoids on the TPA-induced monocytic differentiation. J Leukoc Biol 1992; 52:173-182; Balboa M A, Saez Y, Balsinde J. Calcium-independent phospholipase A2 is required for lysozyme secretion in U937 promonocytes. J Immunol 2003; 170:5276-5280), and granzyme in natural killer (NK) cells and cytotoxic lymphocytes (Bochan M R, Goebel W S, Brahmi Z. Stably transfected antisense granzyme B and perforin constructs inhibit human granule-mediated lytic ability. Cell Immunol 1995; 164:234-239; Gong J H., Maki G, Klingemann HG. Characterization of a human cell line (NK-92) with phenotypical and functional characteristics of activated natural killer cells. Leukemia 1994; 8:652-658; Maki G, Klingemann H G, Martinson J A, Tam Y K. Factors regulating the cytotoxic activity of the human natural killer cell line, NK-92. J Hemather Stem Cell Res 2001; 10:369-383; and Takayama H, Trenn G, Sitkovsky M V. A novel cytotoxic T lymphocyte activation assay. Immunol Methods 1987; 104:183-1907-10). These mediators can be released at sites of injury and can contribute to inflammation and repair, such as in the lung and elsewhere, as a result of the infiltration of these cells to the tissue site of injury or disease. Leukocytes release these granules via an exocytotic mechanism (Burgoyne R D, Morgan A. Secretory granule exocytosis. Physiol Rev 2003; 83:581-632; Logan M R, Odemuyiwa S O, Moqbel R. Understanding exocytosis in immune and inflammatory cells: the molecular basis of mediator secretion. J Allergy Clin Immunol 2003; 111: 923-932), Mast cells, which usually do not circulate in the blood stream, and basophils contain secretory cytoplasmic granules which store and can release, upon cell activation, preformed inflammatory (anaphylactic) mediators, such as histamine; proteoglycans, such as heparin and chondroitin sulphate; proteases such as tyrptase, chymase, carboxypeptidase, and cathepsin G-like protease; chemotactic factors, cytokines and metabolites of arachidonic acid that act on the vasculature, smooth muscle, connective tissue, mucous glands and inflammatory cells.

Neutrophils, also known as polymorphonuclear leukocytes (PMN), comprise 50 to 60% of the total circulating leukocytes. Neutrophils act against infectious agents, such as bacteria, fungi, protozoa, viruses, virally infected cells, as well as tumor cells, that penetrate the body's physical barriers at sites of infection or injury. Neutrophils mature through six morphological stages: myeloblast, promyeloblast, myelocyte, metamyelocyte, non-segmented (band) neutrophil, and segmented (functionally active) neutrophil.

In neutrophils, inflammatory mediators are stored in primary (azurophil), secondary (specific), and tertiary (gelatinase) granules, as well as in secretory vesicles. Among numerous mediators of inflammation, primary (azurophil) granules contain myeloperoxidase (MPO), lysozyme, defensins, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, and proteinase 3 (see, for example, Hartwig J H, Thelen M, Rosen A, Janmey P A, Nairn A C, Aderem A. MARCKS is an actin filament crosslinking protein regulated by protein kinase C and calcium-calmodulin. Nature 1992; 356:618-622); secondary (specific) granules contain lysozyme, lactoferrin, collagenase, complement activator, phospholipase $A_2$, complement receptors, e.g. CR3. CR4, N-formylmethionyl-leucyl-phenylalanine (FMLP) receptors, laminin receptors, cytochrome $b_{558}$, monocyte-chemotactic factor, histaminase, and vitamin B12 binding protein; and small storage granules contain gelatinase, plasminogen activator, cathepsin B, cathepsin D, beta-D-glucuronidase, alpha-mannosidase, and cytochrome $b_{558}$.

Neutrophil granules contain antimicrobial or cytotoxic substances, neutral proteinases, acid hydrolases and a pool of cytoplasmic membrane receptors. Among azurophil granule constituents myeloperoxidase (MPO) is a critical enzyme in the conversion of hydrogen peroxide to hypochlorous acid. Together with hydrogen peroxide and a halide cofactor it forms an effective microbicidal and cytotoxic mechanism of leukocytes—the myeloperoxidase system.

Defensins, which constitute 30 to 50% of azurophilic granule protein, are small (molecule weight<4000) potent antimicrobial peptides that are cytotoxic to a broad range of bacteria, fungi and some viruses. Their toxicity may be due to membrane permeabilization of the target cell which is similar to other channel-forming proteins (perforins).

Bacterial permeability-increasing (BPI) protein is a member of perforins. It is highly toxic to gram-negative bacteria but not to gram-positive bacteria or fungi and can also neutralize endotoxin, the toxic lipopolysaccharide component of gram-negative bacterial cell envelope.

Lactoferrin sequesters free iron, thereby preventing the growth of ingested microorganisms that survive the killing process and increases bacterial permeability to lysozyme.

Serine proteases such as elastase and cathepsin G hydrolyze proteins in bacterial cell envelopes. Substrates of granulocyte elastase include collagen cross-linkages and proteoglycans, as well as elastin components of blood vessels, ligaments, and cartilage. Cathepsin D cleaves cartilage proteoglycans, whereas granulocyte collagenases are active in cleaving type I and, to a lesser degree, type III collagen from bone, cartilage, and tendon. Collagen breakdown products have chemotactic activity for neutrophils, monocytes, and fibroblasts.

Regulation of tissue destructive potential of lysosomal proteases is mediated by protease inhibitors such as alpha2- macroglobulin and alpha1-antiprotease. These antiproteases are present in serum and synovial fluids. They may function by binding to and covering the active sites of proteases. Protease-antiprotease imbalance can be important in the pathogenesis of emphysema.

Azurophil granules function predominantly in the intracellular milieu (in the phagolysosomal vacuole), where they are involved in the killing and degradation of microorganisms. Neutrophil specific granules are susceptible to release their contents extracellularly and have an important role in initiating inflammation. Specific granules represent an intracellular reservoir of various plasma membrane components including cytochrome b (component of NADPH oxidase, an enzyme responsible for the production of superoxide), receptors for complement fragment iC3b (CR3, CR4), for laminin, and formylmethionyl-peptide chemoattractants. In addition to others, there is histaminase which is relevant for the degradation of histamine, vitamin binding protein, and plasminogen activator which is responsible for plasmin formation and cleavage of C5a from C5.

The importance of neutrophil granules in inflammation is apparent from studies of several patients with congenital abnormalities of the granules. Patients with Chediak-Higashi syndrome have a profound abnormality in the rate of establishment of an inflammatory response and have abnormally large lysosomal granules. The congenital syndrome of specific granule deficiency is an exceedingly rare disorder characterized by diminished inflammatory responses and severe bacterial infections of skin and deep tissues.

Although mechanisms regulating exocytotic secretion of these granules are only partially understood, several key molecules in the process have been identified, including intracellular Ca2+ transients (Richter et al. Proc Natl Acad Sci USA 1990; 87:9472-9476; Blackwood et al., Biochem J 1990; 266:195-200), G proteins, tyrosine and protein kinases (PK, especially PKC) (Smolen et al., Biochim Biophys Acta 1990; 1052:133-142; Niessen et al., Biochim. Biophys. Acta 1994; 1223:267-273; Naucler et al., Pettersen et al., Chest 2002; 121; 142-150), Rac2 (Abdel-Latif et al., Blood 2004; 104: 832-839; Lacy et al., J Immunol 2003; 170:2670-2679) and various SNARE's, SNAP's and VAMP's (Sollner et al., Nature 1993; 362: 318-324; Lacy, Pharmacol Ther 2005; 107:358-376).

SNARE (Soluble N-ethylmaleimide attachment protein receptor) proteins are a family of membrane-associated proteins characterized by an alpha-helical coiled-coil domain called the SNARE motif (Li et al., Cell. Mol. Life. Sci. 60: 942-960 (2003)). These proteins are classified as v-SNAREs and t-SNAREs based on their localization on vesicle or target membrane; another classification scheme defines R—SNAREs and Q-SNAREs, as based on the conserved arginine or glutamine residue in the centre of the SNARE motif. SNAREs are localized to distinct membrane compartments of the secretory and endocytic trafficking pathways, and contribute to the specificity of intracellular membrane fusion processes. The t-SNARE domain consists of a 4-helical bundle with a coiled-coil twist. The SNARE motif contributes to the fusion of two membranes. SNARE motifs fall into lour classes: homologues of syntaxin 1a (t-SNARE), VAMP-2 (v-SNARE), and the N- and C-terminal SNARE motifs of SNAP-25. One member from each class may interact to form a SNARE complex. The SNARE motif is found in the N-terminal domains of certain syntaxin family members such as syntaxin 1a, which is required for neurotransmitter release (Lerman et al., Biochemistry 39: 8470-8479 (2000)), and syntaxin 6, which is found in endosomal transport vesicles (Misura et al., Proc. Natl. Acad. Sci. U.S.A. 99: 9184-9189 (2002)).

SNAP-25 (synaptosome-associated protein 25 kDa) proteins are components of SNARE complexes, which may account for the specificity of membrane fusion and to directly execute fusion by forming a tight complex (the SNARE or core complex) that brings the synaptic vesicle and plasma membranes together. The SNAREs constitute a large family of proteins that are characterized by 60-residue sequences known as SNARE motifs, which have a high propensity to form coiled coils and often precede carboxy-terminal transmembrane regions. The synaptic core complex is formed by four SNARE motifs (two from SNAP-25 and one each from synaptobrevin and syntaxin 1) that are unstructured in isolation but form a parallel four-helix bundle on assembly. The crystal structure of the core complex has revealed that the helix bundle is highly twisted and contains several salt bridges on the surface, as well as layers of interior hydrophobic residues. A polar layer in the centre of the complex is formed by three glutamines (two from SNAP-25 and one from syntaxin 1) and one arginine (from synaptobrevin) (Rizo et al., Nat Rev Neurosci 3: 641-653 (2002)). Members of the SNAP-25 family contain a cluster of cysteine residues that can be palmitoylated for membrane attachment (Risinger et al. J. Biol. Chem. 268: 24408-24414 (1993)).

The major role of neutrophils is to phagocytose and destroy infectious agents. They also limit the growth of some microbes, prior to onset of adaptive (specific) immunological responses. Although neutrophils are essential to host defense, they have also been implicated in the pathology of many chronic inflammatory conditions and in ischemia-reperfusion injury. Hydrolytic enzymes of neutrophil origin and oxidatively inactivated protease inhibitors can be detected in fluid isolated from inflammatory sites. Under normal conditions, neutrophils can migrate to sites of infection without damage to host tissues. However, undesirable damage to a host tissue can sometimes occur. This damage may occur through several independent mechanisms. These include premature activation during migration, extracellular release of toxic products during the killing of some microbes, removal of infected or damage host cells and debris as a first step in tissue remodeling, or failure to terminate acute inflammatory responses. Ischemia-reperfusion injury is associated with an influx of neutrophils into the affected tissue and subsequent activation. This may be triggered by substances released from damaged host cells or as a consequence of superoxide generation through xanthine oxidase.

Under normal conditions, blood may contain a mixture of normal, primed, activated and spent neutrophils. In an inflammatory site, mainly activated and spent neutrophils are present. Activated neutrophils have enhanced production of reactive oxygen intermediates (ROI). A subpopulation of neutrophils with the enhanced respiratory burst has been detected in the blood of people with an acute bacterial infection and patients with the adult respiratory distress syndrome (ARDS). This is an example of a neutrophil paradox. Neutrophils have been implicated in the pathology of this condition because of the large influx of these cells into the lung and the associated tissue damage caused by oxidants and hydrolytic enzymes released from activated neutrophils. The impairment of neutrophil microbicidal activity that occurs as the ARDS worsens may be a protective response on the part of the host, which is induced locally by inflammatory products.

The acute phase of thermal injury is also associated with neutrophil activation, and this is followed by a general impairment in various neutrophil functions. Activation of neutrophils by immune complexes in synovial fluid contributes to the pathology of rheumatoid arthritis. Chronic activation of neutrophils may also initiate tumor development because some ROI generated by neutrophils damage DNA and proteases promote tumor cell migration. In patients suffering from severe burns, a correlation has been established between the onset of bacterial infection and reduction in the proportion and absolute numbers of neutrophils positive for antibody and complement receptors. Oxidants of neutrophil origin have also been shown to oxidize low-density lipoproteins (LDL), which are then more effectively bound to the plasma membrane of macrophages through specific scavenger receptors. Uptake of these oxidized LDL by macrophages may initiate atherosclerosis. In addition, primed neutrophils have been found in people with essential hypertension, Hodgkin's disease, inflammatory bowel disease, psoriasis, sarcoidosis, and septicemia, where priming correlates with high concentrations of circulating TNF-alpha (cachectin).

Hydrolytic damage to host tissue and therefore chronic inflammatory conditions may occur when antioxidant and antiprotease screens are overwhelmed. Antiprotease deficiency is thought to be responsible for the pathology of emphysema. Many antiproteases are members of the serine protease inhibitor (SERPIN) family. Although the circulation is rich in antiproteases, these large proteins may be selectively excluded at sites of inflammation because neutrophils adhere to their targets. Oxidative stress may initiate tissue damage by reducing the concentration of extracellular antiproteases to below the level required to inhibit released proteases. Chlorinated oxidants and hydrogen peroxide can inactivate antiproteases such as alpha1-protease inhibitor and alpha2-macroglobulin, which are endogenous inhibitors of elastase, but simultaneously activate latent metalloproteases such as collagenases and gelatinase, which contribute to the further inactivation of antiproteases.

Cytoplasmic constituents of neutrophils may also be a cause of formation of specific anti-neutrophil cytoplasmic antibodies (ANCA), which are closely related to the development of systemic vasculitis and glomerulonephritis. ANCA are antibodies directed against enzymes that are found mainly within the azurophil or primary granules of neutrophils. There are three types of ANCA that can be distinguished by the patterns they produce by indirect immunofluorescence on normal ethanol-fixed neutrophils. Diffuse fine granular cytoplasmic fluorescence (cANCA) is typically found in Wegener's granulomatosis, in some cases of microscopic polyarteritis and Churg Strauss syndrome, and in some cases of crescentic and segmental necrotizing glomerulonephritis. The target antigen is usually proteinase 3. Perinuclear fluorescence (pANCA) is found in many cases of microscopic polyarteritis and glomerulonephritis. These antibodies are often directed against myeloperoxidase but other targets include elastase, cathepsin G, lactoferrin, lysozyme and beta-D-glucuronidase. The third group designated "atypical" ANCA includes neutrophil nuclear fluorescence and some unusual cytoplasmic patterns and while a few of the target antigens are shared with pANCA, the others have not been identified yet. pANCA are also found in a third of patients with Crohn's disease. The reported incidence of ANCA in rheumatoid arthritis and SLE varies considerably but the patterns are predominantly pANCA and atypical ANCA.

The eosinophil is a terminally differentiated, end-stage leukocyte that resides predominantly in submucosal tissue and is recruited to sites of specific immune reactions, including allergic diseases. The eosinophil cytoplasm contains large ellipsoid granules with an electron-dense crystalline nucleus and partially permeable matrix. In addition to these large primary crystalloid granules, there is another granule type that is smaller (small granule) and lacks the crystalline nucleus. The large specific granules of eosinophils contain at least four distinct cationic proteins, which exert a range of biological effects on host cells and microbial targets: major basic protein (MBP), eosinophil cationic protein (ECP), eosinophil derived neurotoxin (EDN), and eosinophil peroxidase (FPO). Basophils contain about one fourth as much major basic protein as eosinophils together with detectable amounts of EDN, ECP and EPO. Small amounts of EDN and ECP are also found in neutrophils (Gleich G J. Mechanisms of eosinophil-associated inflammation. J Allergy Clin Immunol 2000; 105:651-663). MBP appears to lack enzymatic activity but is a highly cationic polypeptide which may exert its toxic activities by interactions with lipid membranes leading to their derangement. Both MBP and EPO can act as selective allosteric inhibitors of agonist binding to M2 muscarinic receptors. These proteins may contribute to M2 receptor dysfunction and enhance vagally mediated bronchoconstriction in asthma. EDN can specifically damage the myelin coat of neurons. Histaminase and a variety of hydrolytic lysosomal enzymes are also present in the large specific granules of eosinophils. Among the enzymes in small granules of eosinophils are aryl sulphatase, acid phosphatase, and a 92 kDa metalloproteinase, a gelatinase. Eosinophils can elaborate cytokines which include those with potential autocrine growth-factor activities for eosinophils and those with potential roles in acute and chronic inflammatory responses. Three cytokines have growth-factor activities for eosinophils: granulocyte-macrophage colony-stimulating factor (GM-CSF), IL-3 and IL-5. Other cytokines produced by human eosinophils that may have activities in acute and chronic inflammatory responses include IL-1-alpha, IL-6, IL-8, TNF-alpha and both transforming growth factors, TGF-alpha and TGF-beta.

Eosinophils contain crystalloid granules that contain MBP, eosinophil cationic protein, EPO, and eosinophil-derived neurotoxin (Gleich, J Allergy Clin Immunol 2000; 105:651-663). The human promyelocytic cell line HL-60 clone 15 can be used to examine secretion of EPO. This cell line was established from a clone of HL-60 that had been grown at an elevated pH for two months (Fischkoff, Leuk Res 1988; 12:679-686) and then treated with butyric acid to allow the cells to differentiate so as to exhibit many of the characteristics of peripheral blood eosinophils, including expression of eosinophil-specific granule proteins (Rosenberg et al., J Exp Med 1989; 170:163-176; Tiffany et al., J Leukoc Biol 1995; 58:49-54; Badewa et al., Exp Biol Med 2002; 227:645-651).

Eosinophils can participate in hypersensitivity reactions, especially through two lipid inflammatory mediators, leukotriene $C^4$ ($LTC^4$) and platelet activating factor (PAF). Both mediators contract airway smooth muscle, promote the secretion of mucus, alter vascular permeability and elicit eosinophil and neutrophil infiltration. In addition to the direct activities of these eosinophil-derived mediators, MBP can stimulate the release of histamine from basophils and mast cells, and MBP can stimulate the release of EPO from mast cells. Eosinophils can serve as a local source of specific lipid mediators as well as induce the release of mediators from mast cells and basophils. Eosinophil granule content is released following similar stimuli to neutrophil granules, e.g. during phagocytosis of opsonized particles and by chemotactic factors. Neutrophil lysosomal enzymes act primarily on material engulfed in phagolysosomes, while the eosinophil granule contents act mainly on extracellular target structure such as parasites and inflammatory mediators.

Monocyte and macrophage development takes place in the bone marrow and passes through the following steps: stem cell; committed stem cell; monoblast; promonocyte; monocyte in bone marrow; monocyte in peripheral blood; and macrophage in tissues. Monocyte differentiation in the bone marrow proceeds rapidly (1.5 to 3 days). During differentiation, granules are formed in monocyte cytoplasm and these can be divided as in neutrophils into at least two types. However, they are fewer and smaller than their neutrophil counterparts (azurophil and specific granules). Their enzyme content is similar.

Granule-bound enzymes of monocytes/macrophages include lysozyme, acid phosphatase, and beta-glucuronidase. As a model for in vivo studies, lysozyme secretion from U937 cells was used. This cell line is derived from a human histiocytic lymphoma and has been used as a monocytic cell line that can be activated by a variety of agonists, such as PMA (Hoff et al., J Leukoc Biol 1992; 52:173-182; Balboa et al., J Immunol 2003; 170:5276-5280; Sundstrom et al., Int J Cancer 1976; 17:565-577).

Natural killer (NK) cells and cytotoxic lymphocytes contain potent cytotoxic granules including perforin, a pore-forming protein, and granzymes, lymphocyte-specific serine proteases. For example, the NK-92 cell line is an IL-2-dependent human line established from a patient with rapidly progressive non-Hodgkin's lymphoma (Gong J H., Maki G, Klingemann H G. Characterization of a human cell line (NK-92) with phenotypical and functional characteristics of activated natural killer cells. Leukemia 1994; 8:652-658). NK-92 cells express high levels of molecules involved in the perforin-granzyme cytolytic pathway that targets a wide range of malignant cells (Gong et al, vide infra, and Maki G, Klingemann H G, Martinson J A, Tam Y K. Factors regulating the cytotoxic activity of the human natural killer cell line, NK-92. J Hematother Stem Cell Res 2001: 10:369-383).

Granzymes are exogenous serine proteases that are released by cytoplasmic granules within cytotoxic T cells and natural killer cells. Granzymes can induce apoptosis within virus-infected cells, thus destroying them.

Extracellular release of a mediator of inflammation (inflammatory mediator) from a granulocyte (or leukocyte), and extracellular release of more than one mediator of inflammation (inflammatory mediator) from a granulocyte (or leukocyte) are sometimes referred to herein as degranulation. In a preferred embodiment, the release of a mediator of inflammation comprises release of said mediator from a granule located in the interior of a granulocyte or leukocyte. The release of inflammatory mediator is preferably the release of an inflammatory mediator from these granules.

Neutrophils and macrophages, upon priming by pro-inflammatory agents (inflammatory stimulants) such as TNFα, dramatically increase their synthesis of MARCKS protein: as much as 90% of the new protein formed by neutrophils in response to either TNFα or lipopolysaccharide (LPS) is MARCKS (Thelen M, Rosen A, Nairn A C, Aderem A. Tumor necrosis factor alpha modifies agonist-dependent responses in human neutrophils by inducing the synthesis and myristoylation of a specific protein kinase C substrate. Proc Natl Acad Sci USA 1990; 87:5603-5607). MARCKS can thus have an important role in subsequent release of inflammatory mediators when granule-containing cells, such as neutrophils and macrophages, are stimulated by agonists, especially those that work by activating PKC (Burgoyne et al., Physiol Rev 2003; 83:581-632; Logan et al. J Allergy Clin Immunol 2003; 111: 923-932; Smolen et al., Biochim Biophys Acta 1990; 1052:133-142; Niessen et al., Biochim. Biophys. Acta 1994; 1223:267-273; Naucler et al., Leukoc Biol 2002; 71:701-710).

The present invention is also directed to a method of inhibiting the exocytotic release of at least one inflammatory mediator from at least one inflammatory cell comprising contacting the at least one inflammatory cell, which cell comprises at least one inflammatory mediator contained within a vesicle inside the cell, with at least one peptide selected from the group consisting of a MANS peptide and an active fragment thereof in an effective amount to reduce the release of the inflammatory mediator from the inflammatory cell as compared to the release of the inflammatory mediator from the same type of inflammatory cell that would occur in the absence of the at least one peptide.

The present invention is further directed to a method of inhibiting the release of at least one inflammatory mediator from at least one inflammatory cell in a tissue or fluid of a subject comprising the administration to the subject's tissue and/or fluid, which comprises at least one inflammatory cell comprising at least one inflammatory mediator contained within a vesicle inside the cell, a therapeutically effective amount of a pharmaceutical composition comprising at least one peptide selected from the group consisting of a MANS peptide and an active fragment thereof in a therapeutically effective amount to reduce the release of the inflammatory mediator from at least one inflammatory cell as compared to release of the inflammatory mediator from at least one of the same type of inflammatory cell that would occur in the absence of the at least one peptide. More specifically, reducing the release of an inflammatory mediator comprises blocking or inhibiting the MARCKS-related mechanism that releases an inflammatory mediator from the inflammatory cell.

The MANS peptide used in the present methods comprises SEQ ID NO: 1. An active fragment useful in the present invention comprises at least one myristoylated N-terminal fragment of MANS (SEQ ID NO: 1), which comprises at least five or at least six amino acids, wherein the first, or N-terminal, amino acid of said fragment begins at the N-terminal glycine of SEQ ID NO: 1 (MANS peptide). More specifically, an active fragment can be selected from the group consisting of N-myristoyl-GAQFSKTAAKGEAAAERPGEAAV (SEQ ID NO: 2); N-myristoyl-GAQFSKTAAKGEAAAER-PGEAA (SEQ ID NO: 3); N-myristoyl-GAQFSK-TAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11) N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); N-myristoyl-GAQFSK (SEQ ID NO: 19) and N-myristoyl-GAQFS (SEQ ID NO: 20).

The presence of the hydrophobic N-terminal myristoyl moiety in these peptides can enhance their compatibility with and presumably their permeability to plasma membranes, and potentially enable the peptides to be taken up by cells. The hydrophobic insertion of myristate into a bilayer can provide a partition coefficient or apparent association constant with lipids of up to $10^4$ M$^{-1}$ or a unitary Gibbs free binding energy of about 8 kcal/mol (see, for example, Peitzsch, R. M., and McLaughlin, S., *Binding of acylated peptides and fatty acids to phospholipid vesicles: pertinence to myristoylated proteins*, Biochemistry 32: 10436-10443, 1993) which is sufficient, at least in part, to permit a partitioning of the MANS peptide and of myristoylated MANS peptide fragments as described herein into the plasma membrane of a cell while additional functional groups and their interactions within the MANS peptide (which is myristoylated) and within myristoylated MANS peptide fragments can potentiate their relative membrane permeabilities. The fragments can each exhibit partition coefficients and membrane affinities that are representative of their respective structure. The fragments can be prepared by methods of peptide synthesis known in the art, such as by solid phase peptide synthesis (see, for example, the methods described in Chan, Weng C. and White, Peter D. Eds., Fmoc Solid Phase Peptide Synthesis: A Practical Approach, Oxford University Press, New York, N.Y. (2000); and Lloyd-Williams, P. et al. Chemical Approaches to the Synthesis of Peptides and Proteins (1997)) and purified by methods known in the art, such as by high pressure liquid chromatography. Molecular weight of each peptide can be confirmed by mass spectroscopy with each showing a peak with an appropriate molecular mass. Efficacy of the individual peptides and of combinations of individual peptides (for example, combinations of 2 of the peptides, combinations of 3 of the peptides, combinations of 4 of the peptides) in the methods of this disclosure can be readily determined without undue experimentation using the procedures described in the examples disclosed herein. A preferred combination will comprise two of the peptides; a preferred molar ratio of the peptides can be from 50:50 to 99.99 to 0.01, which ratio can be readily determined using the procedures described in the examples disclosed herein.

In some embodiments, it is possible that a peptide of the present invention may block secretory processes that are physiologically important, including basal secretory functions. Although inventors do not wish to be bound to any particular theory of the invention, it is thought that the mechanisms regulating such basal secretion are different than those regulating stimulated secretion. Alternatively, basal secretory mechanisms may require less MARCKS protein than stimulated secretion. Since therapies to block MARCKS-mediated secretion are unlikely to eliminate all MARCKS function, basal secretion may accordingly be preserved.

The present invention demonstrates that the myristoylated alanine-rich C kinase substrate (MARCKS), a widely distributed PKC substrate, may be a key regulatory molecule mediating mucin granule release by normal human bronchial epithelial (NHBE) cells. Secretion of mucin from these cells may be maximized by activation of both PKC and PKG. It is believed that MARCKS serves as the point of convergence for coordinating the actions of these two protein kinases to control mucin granule release. The mechanism appears to involve PKC-dependent phosphorylation of MARCKS, which releases MARCKS from the plasma membrane into the cytoplasm, where it is, in turn, dephosphorylated by a protein phosphatase 2A (PP2A) that is activated by PKG. This dephosphorylation may allow MARCKS to regain its membrane-binding capability, enabling its attachment to membranes of cytoplasmic mucin granules. In addition, MARCKS interacts with actin and myosin in the cytoplasm and thus may be able to tether the granules to the cellular contractile apparatus, thus, mediating subsequent granule movement and exocytosis. Interestingly, secretion of the inflammatory mediator MPO from neutrophils may also be maximized by activation of both PKC and PKG.

It is believed by the inventors that MARCKS also serves as the point of convergence for coordinating actions of these two protein kinases (PKC and PKG) that control secretion from membrane-bound (i.e., membrane-encapsulated=vesiculated) compartments in inflammatory cells (e.g., secretion of MPO from neutrophils). The inventors believe that secretion of an inflammatory mediator from a membrane-bound (i.e., membrane-encapsulated or vesiculated) compartment in an inflammatory cell, which mediator may be associated with local tissue inflammation and with chemotaxic migration of additional inflammatory cells such as neutrophils (e.g., as a function of an inflammatory mediator concentration gradient) is at least in part controlled or modulated or attenuated in a MARCKS-related mechanism in a manner analogous to the mechanism associated with release of mucin from mucin granules.

Transformed cell lines of airway epithelium tend to contain altered signaling pathways, and cell lines or nondifferentiated cells may not respond to exogenous stimuli in a manner similar to differentiated cells in vivo. The NHBE cells utilized in the present study were cultured at the air/liquid interface, resulting in fully differentiated primary cell cultures that maintained a well documented structure and function similar to those in in vivo studies. See, Krunkosky et al. supra; Adler et al., Am. J. Respir. Cell Mol. Biol. 2, 145-154 (1990); Kaartinen et al., In Vitro Cell. Dev. Biol. Anim. 29A, 481-492 (1993); Gray et al., Am. J. Respir. Cell Mol. Biol. 14, 104-112 (1996). This air/liquid methodology to culture airway epithelial cells was developed several years ago to provide an in vitro model system to study mechanisms involved in various cellular processes in airway epithelium. The cell cultures contain secretory cells as well as ciliated and basal cells. Results obtained from this culture system are relevant to the response of cells in vivo because the heterogeneous cell-cell contacts and polarized epithelial structure of in vivo systems are maintained, which likely influence cell behavior in situ. Although MARCKS is likely present in non-secretory cells also, the clear and rapid causal associations between modifications of MARCKS and secretory outcomes suggest that mucin secretion is the direct effect of the MARCKS-related molecular events occurring within the secretory cells.

The present invention demonstrates concurrent activation of both PKC and PKG was able to enhance mucin secretion from differentiated NHBE cells, and that activation of either kinase alone may not be sufficient to elicit a robust secretory response. Similarly, secretion of the inflammatory mediator MPO from canine or human neutrophils was enhanced by concurrent activation of both PKC and PKG, while activation of either kinase alone was insufficient to induce a maximal secretory response. An enhanced secretory response to PMA alone was documented in NHBE cells (see Example 5), and in neutrophils, although the magnitude of the response was much less than that observed by others in a rat goblet-like cell line. See, Abdullah et al, supra. In addition, although it was reported previously that a cGMP analogue could induce significant mucin secretion from cultured guinea pig tracheal epithelial cells (Fischer et al., supra), it should be noted that this response did not reach significant levels until 8 h of exposure. A secretory response uwith such a long lag period is unlikely to be a direct effect and probably involves de novo protein synthesis as opposed to release of preformed and stored cytoplasmic granules. Nevertheless, the apparent synergistic effect involving cooperative activation of both PKC and PKG may suggest a complex and stringent signaling mechanism mediating mucin secretion and/or inflammatory mediators. Applicants note that the pathway disclosed below was used to study inflammatory mediator release from neutrophils and is likely the same pathway as that used to study goblet cell secretions.

In one aspect, the present invention is directed to the contact and/or administration of the peptide described above and throughout the specification with an inflammatory cell that may be contained in the tissue or fluid of a subject, which cell contains at least one inflammatory mediator contained within a vesicle inside the cell. The inflammatory cell is preferably a leukocyte, more preferably a granulocyte, which can be further classified as a neutrophil, a basophil, an eosinophil or a combination thereof. The inflammatory cells contacted in the present method may also be a monocyte/macrophage.

The present invention is also directed to reducing the release of inflammatory mediators contained within the vesicles of inflammatory cells. These inflammatory mediators can be selected from the group consisting of myeloperoxidase (MPO), eosinophil peroxidase (EPO), major basic protein (MBP), lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucyl-phenylalanine (FMLP) receptor, laminin receptor, cytochrome $b_{558}$, monocyte-chemotactic factor, histaminase, vitamin B12 binding protein, gelatinase, plasminogen activator, beta-D-glucuronidase, and a combination thereof. Preferably, these inflammatory mediators are selected from the group consisting of myeloperoxidase (MPO), eosinophil peroxidase (EPO), major basic protein (MBP), lysozyme, granzyme, and a combination thereof.

In one aspect, the present invention contacts an effective amount of the peptide with an inflammatory cell, wherein the effective amount is defined as a degranulation-inhibiting amount of MANS peptide or an active fragment thereof that reduces the amount of an inflammatory mediator released from at least one inflammatory cell from about 1% to about 99% as compared to the amount released from at least one inflammatory cell in the absence of MANS peptide or an active fragment thereof. More preferably, this effective amount of the contacted peptide comprises a degranulation-inhibiting amount of MANS peptide or an active fragment thereof that reduces the amount of an inflammatory mediator released from at least one inflammatory cell from between about 5-50% to about 99% as compared to the amount released from at least one inflammatory cell in the absence of MANS peptide or an active fragment thereof.

Administration of a composition comprising a degranulation-inhibiting amount of the MANS peptide or a degranulation-inhibiting amount of an active fragment thereof, such as a pharmaceutical composition of the MANS peptide or an active fragment thereof, for human or animal use, provides the MANS peptide or active fragment thereof at least to the site in or on a tissue or to a fluid-containing or mucus-containing layer in contact with the surface of a tissue where an inflammatory granulocytic cell resides or into which an inflammatory granulocytic cell will invade, thus enabling the MANS peptide or an active fragment thereof to contact the inflammatory granulocytic cell. In one aspect, administration of such a composition can be made at the first onset or first detection of inflammation or first perception of inflammation by the human or animal or at the first perceptible change in the level of inflammation in a human or animal to reduce the amount of inflammation that would otherwise occur in the absence of the MANS peptide or active fragment thereof. In another aspect, administration can be made during an ongoing inflammation of a tissue in the human or animal to reduce the amount of additional inflammation that would otherwise occur in the absence of the MANS peptide or active fragment thereof. While the amount and frequency of dose can be determined by clinical evaluation and be a function of the disease or source of inflammation and the extent of tissue involved and the age and size of the patient, it is anticipated that dosing of a pharmaceutical composition can be repeated after 3 to 8 hours, preferably after 6 to 8 hours after the first administration of the pharmaceutical composition.

In one aspect of this invention, administration of a degranulation-inhibiting amount of MANS peptide or an active fragment thereof as described herein to a site of inflammation in a subject, which site of inflammation has resulted from the onset of entry of a disease, a condition, a trauma, a foreign body, or a combination thereof at the site of inflammation in the subject, can reduce the amount of a mediator of inflammation released from infiltrating leukocytes at the site of inflammation, where the leukocytes are preferably granulocytes. The administration of the MANS peptide and/or at least one active fragment thereof can reduce the amount of a mediator of inflammation released from leukocytes such as granulocytes infiltrating into the site of inflammation. The degranulation-inhibiting amount of MANS peptide, or the degranulation-inhibiting amount of an active fragment thereof, is sufficient to reduce or inhibit the exocytotic release of inflammatory mediators from granules contained within the inflammatory cells infiltrating into the site. Degranulation-inhibiting efficacy is measured at a time after administration of the MANS peptide or the fragment thereof by comparison of the percent of inhibition (i.e., percent of reduction) of the release of mediators of inflammation from said cells (leukocytes or granulocytes or other inflammatory cells) relative to the level or amount or concentration of said mediators of inflammation released or produced at approximately the same time in the absence of MANS peptide and/or in the absence of the active fragment thereof. Additionally, a skilled clinician can determine whether inflammation at the tissue site has been reduced by measuring symptoms and parameters of inflammation known as indicators of the disease to determine whether a sufficient or therapeutically effective amount MANS peptide and/or an active fragment thereof has been administered. A sufficient degranulation-inhibiting amount is the percentage of reduction of a mediator of inflammation released from a granulocyte, at the site of inflammation, which is from about 1% to about 99%, preferably from 5% to about 99%, more preferably from about 10% to about 99%, even more preferably from about 25% to 99%, and even more preferably from about 50% to about 99% of the amount of said mediator of inflammation released from said granulocyte in the absence of MANS peptide or an active fragment thereof tested under the same conditions. Reductions of greater than 99%, such as up to 99.9% and up to 99.99%, approaching 100%, are also considered to be a part of this invention.

In one aspect of this invention, administration of a degranulation-inhibiting amount of MANS peptide to a site of inflammatory stimulation in an animal, which site of inflammatory stimulation has been created by administration of an inflammation-stimulating amount of an inflammatory stimulant to said site, can reduce the amount of a mediator of inflammation released from a granulocyte, which granulocyte is stimulated by said inflammatory stimulant at said site of inflammatory stimulation, from about 1% to about 99%, preferably from 5% to about 99%, more preferably from about 10% to about 99%, even more preferably from about 25% to 99%, and even more preferably from about 50% to about 99% of the amount of said mediator of inflammation released from said granulocyte in the absence of MANS peptide in the presence of the identical inflammation-stimulating amount of said inflammatory stimulant.

In another aspect of this invention, administration of a degranulation-inhibiting amount of MANS peptide to a site of inflammatory stimulation in an animal, which site of inflammatory stimulation has been created by administration of an inflammation-stimulating amount of an inflammatory stimulant to said site, can reduce the amount of a mediator of inflammation released from a granulocyte, which granulocyte is stimulated by said inflammatory stimulant at said site of inflammatory stimulation, by 100% of the amount of said mediator of inflammation released from said granulocyte in the absence of MANS peptide in the presence of the identical inflammation-stimulating amount of said inflammatory stimulant.

An example of an inflammatory stimulant used in in vitro examples herein is phorbol 12-myristate 13-acetate (PMA). Monocyte chemoattractant protein (MCP-1) is early as effective as C5a, and much more potent than IL-8, in the degranulation of basophils, resulting in histamine release. Histamine release can occur after stimulation with chemokines (i.e., chemoattractant cytokines), RANTES and MIP-1.

In a preferred embodiment, relative to the basal concentration of MARCKS peptide present at the site of inflammatory stimulation, the degranulation-inhibiting amount of MANS peptide administered to a site of inflammatory stimulation in an animal comprises from about 1 time to about 1,000,000 times the concentration of the MARCKS peptide at said site of inflammatory stimulation, preferably from about 1 time to about 100,000 times the concentration of the MARCKS peptide at said site of inflammatory stimulation, more preferably from about 1 time to about 10,000 times the concentration of the MARCKS peptide at said site of inflammatory stimulation, even more preferably from about 1 time to about 1,000 times the concentration of the MARCKS peptide at said site of inflammatory stimulation, even more preferably from about 1 time to about 100 times the concentration of the MARCKS peptide at said site of inflammatory stimulation, and even more preferably from about 1 time to about 10 times the concentration of the MARCKS peptide at said site of inflammatory stimulation.

In a preferred embodiment, the granulocyte resides on or in the airway of an animal, preferably a human, and the MANS peptide or an active fragment thereof is administered by inhalation, such as by inhalation of a pharmaceutical composition comprising the MANS peptide, for example a pharmaceutical composition comprising the MANS peptide or an active fragment thereof and an aqueous solution, which composition is administered in the form of an aerosol, or a pharmaceutical composition comprising the MANS peptide or an active fragment thereof in the form of a dry powder, which composition is administered using a dry powder inhaler. Other methods and devices known in the art for administration of a solution or powder by inhalation such as, for example, droplets, sprays, and nebulizers, can be useful.

The present invention in one embodiment is directed to the administration of at least one peptide comprising a MANS peptide or an active fragment thereof in a therapeutically effective amount into tissue or fluid of a subject where the subject is afflicted by a respiratory disease, which is preferably asthma, chronic bronchitis or COPD. In a further embodiment, the subject may be afflicted by a bowel disease, a skin disease, an autoimmune disease, a pain syndrome, and combinations thereof. The bowel disease may be ulcerative colitis, Crohn's disease or irritable bowel syndrome. The subject may be afflicted with a skin disease, such as rosacea, eczema, psoriasis or severe acne. The subject may also be afflicted with arthritis, such as rheumatoid arthritis, psoriatic arthritis, systemic lupus erythematosus. Subjects afflicted by cystic fibrosis may also be treated by the present method and peptides. The present method is preferably useful for the treatment of subjects, such as mammals, and preferably humans, canines, equines and felines.

As used herein, a compound that inhibits the MARCKS protein-mediated release (MARCKS-related release) of mucin from mucin-containing granules (or release of mucus) includes any of those compounds that acts upon a step in the MARCKS protein-mediated signaling pathway that results in mucus secretion, the compound thereby causing a reduction in mucus secretion.

As used herein, "endogenous" refers to compounds that are naturally occurring in a cell. Endogenous MARCKS protein thus refers to MARCKS protein that is found within a cell, as opposed to MARCKS protein introduced into that cell (either administered directly or by genetic engineering techniques).

As used herein, an "active fragment" of a MARCKS protein is one that affects (inhibits or attenuates) the MARCKS protein-mediated release of mucus that occurs in response to a secretagogue such as UTP (uridine 5'-triphosphate). Preferably the active fragment blocks or decreases or attenuates release of inflammatory mediators from inflammatory cells and thereby blocks or decreases or attenuates inflammation. An active peptide fragment of MARCKS comprises an amino acid sequence that is identical or substantially identical to a contiguous sequence of amino acids found in a naturally occurring MARCKS protein. Active MARCKS protein fragments are typically at least about five, ten, fifteen, twenty or twenty-five amino acids in length, but are shorter than the complete MARCKS protein. Such an active peptide fragment of MARCKS comprises a peptide having an amino acid sequence that comprises from about 10 to about 50 contiguous amino acids from an N-terminal sequence of a MARCKS protein. Preferably the peptide is N-terminally myristoylated. A preferred active fragment is an N-terminal myristoylated peptide consisting of an amino acid sequence of from 10 to 50 contiguous amino acids that is identical to a contiguous sequence of amino acids beginning at the N-terminal glycine residue of the MARCKS protein as shown in the myristoylated 24 amino acid MANS peptide, SEQ ID NO: 1, wherein the peptide reduces MARCKS protein-related release of inflammatory mediators from inflammatory cells thereby reducing or attenuating inflammation in a tissue or wherein the peptide both reduces MARCKS protein-related release of inflammatory mediators from inflammatory cells thereby reducing or attenuating inflammation in a tissue and reduces MARCKS protein-related mucus hypersecretion in a cell or tissue, and whereby inflammation in the tissue or mucus hypersecretion in the cell or tissue is reduced compared to that which would occur in the absence of the peptide. Because the MANS peptide is the N-terminal myristoylated sequence (SEQ ID NO: 1) of the MARCKS protein (SEQ ID NOS: 22 or 24), this preferred active peptide is an N-terminal myristoylated peptide consisting of an amino acid sequence of at least 10 contiguous amino acids that is identical to a contiguous sequence of amino acids beginning at the N-terminal glycine residue of the MANS peptide as shown in SEQ ID NO: 1. Additionally, active MARCKS protein fragments may have fewer than about fifty, seventy-five, one hundred or two hundred amino acids.

As used herein, a peptide inhibitor of MARCKS-related mucus secretion (or release of mucin) is a peptide that, when provided to a mucus secreting cell, inhibits or reduces the secretion of mucus compared to that which would occur in the absence of said peptide.

As used herein, "oligonucleotide" refers to DNA or RNA and can include sense and/or antisense strands as appropriate to the desired effect. Oligonucleotides useful in the present invention may be incorporated into recombinant expression vectors that include a promoter and other sequences necessary for expression of the desired translation products (such as a peptide). Alternatively, 'naked' oligonucleotides may be delivered to target cells, as is known in the art (see, e.g., Felgner et al., U.S. Pat. No. 5,580,859).

Mucosa or mucous membranes, as used herein, refers to mucosal tissues of a host wherever they may be located in the body including but not limited to respiratory passages (nasal, oral, tracheal, bronchial), genital passages (vaginal, cervical, and penile), anal and urinary passages (urethra, bladder), and the eyes.

The present invention provides methods and compositions that are useful in inhibiting mucus secretion from epithelial cells. The present inventors have determined that mucin secretory processes in epithelial cells involve the protein kinase C (PKC) substrate MARCKS protein (myristolated alanine-rich C-kinase substrate). By blocking or inhibiting the function and/or production of MARCKS protein in secretory epithelial cells, mucin secretion is reduced over that which would otherwise occur (i.e., that would occur in the absence of such blocking or inhibiting treatment).

The present inventors have shown that use of a fragment of the MARCKS protein reduces mucus secretion by epithelial cells. Additionally, use of antisense fragments directed against the MARCKS mRNA sequence also has been shown to decrease mucus production in epithelial cells.

Despite the previous identification of numerous mucus secretagogues, common signaling pathways and intracellular molecules involved in mucin secretion have not previously been elucidated. The present invention exploits the unexpected discovery that the N-terminal myristolated alanine-rich C-kinase substrate (MARCKS) protein is involved in the secretory process of cells, and particularly in the secretion of mucus from epithelial cells (such as goblet cells). MARCKS protein is a major cellular substrate for protein kinase C (PKC), and the present inventors' studies indicate that it is a central, convergent molecule controlling release of mucin granules. While not wishing to be held to any single theory of the present invention, the MARCKS-related secretion of mucus appears to involve the interaction of mucin secretagogues with airway epithelial (goblet) cells and the activation of two separate protein kinases: PKC and PKG. Activated PKC phosphorylates MARCKS, causing its translocation from the plasma membrane to the cytoplasm, where it is targeted to the mucin granule membrane with the assistance of MARCKS-associated proteins. PKG, activated via the nitric oxide (NO)-cGMP-PKG pathway, in turn activates a cytoplasmic protein phosphatase 2A (PP2A), which dephosphorylates MARCKS, stabilizing its attachment to the granule membrane and allowing MARCKS to cross-link actin filaments, thereby tethering the granule to the cytoskeleton for movement and exocytosis. This proposed signaling pathway is generally depicted in FIG. 1.

The present inventors identified MARCKS mRNA and protein in human bronchial epithelial cells, and both mRNA and protein levels increased with secretory cell differentiation in vitro. The MARCKS in these cells was phosphorylated by the phorbol ester PMA (phorbol 12-myristate 13-acetate), while subsequent addition of a cGMP activator (8-bromo-cGMP), caused dephosphorylation. Mucin secretion provoked (i.e., stimulated) by the pathophysiologically relevant secretagogue uridine triphosphate (UTP) (or by a combination of PMA and 8-bromo-cGMP) was inhibited in a dose-dependent manner by a N-terminal myristoylated peptide fragment of the N-terminal region of MARCKS protein (the proposed site of the protein's attachment to granule membranes). Accordingly, this myristoylated peptide fragment of the N-terminal region of MARCKS protein, as well as other active peptide fragments, are useful in methods of inhibiting mucus secretion. As described further herein, the administration of certain active fragments of MARCKS protein to epithelial mucus-secreting cells has been found to be capable of decreasing mucus secretion by those epithelial mucus-secreting cells.

The present inventors have discovered that antisense oligonucleotides directed against MARCKS protein block or inhibit mucin secretion, as described further herein. Accordingly, such antisense oligonucleotides find use in methods of inhibiting mucus secretion.

Additionally, certain non-protein inhibitors of components in the mucus secretion signaling pathway illustrated in FIG. 1 inhibit mucus secretion in mucus-secreting cells, and are thus useful in the practice of methods the present invention. For example, inhibitors of PKC such as calphostin C, inhibitors of cyclic GMP, such as Rp-8-Br-PET-cGMP, inhibitors of PKG such as Rp-8-Br-PET-cGMP, inhibitors of soluble guanylyl cyclase such as LY83585 and inhibitors of phosphatase such as okadaic acid each inhibit mucin secretion in cells stimulated by the above-listed secretagogues. Accordingly, such inhibitors of components of the mucin secretion signaling pathway find use in methods of inhibiting mucus secretion.

The present invention thus provides methods and compositions useful in regulating (decreasing or attenuating) mucus secretion. Such methods and compositions are useful in the treatment of medical conditions in which mucus hypersecretion occurs, and are particularly useful in the respiratory tract.

Accordingly, the present invention provides methods and compositions for regulating mucus secretion, by regulating (attenuating or decreasing) the effects of MARCKS protein in the mucus-secretory pathway. Such regulation (attenuation) can be achieved by administering active fragments of MARCKS protein in pre-determined amounts, or administration of these or other compounds (alone or in combination) that inhibit the MARCKS-related secretory pathway. Such compounds include those that block the dephosphorylated MARCKS protein binding event that leads to mucin release. Such compounds may bind to and block the site that is bound by endogenous MARCKS protein, or may bind to the MARCKS protein at the pertinent site. The MANS peptide described herein is believed to compete with endogenous MARCKS protein for the pertinent binding site in the cell, thus blocking the MARCKS-mediated release of mucin within the cell. Alternatively, an antibody directed to the N-terminal sequence of the MARCKS protein (e.g., the MANS sequence) would be predicted to bind to endogenous MARCKS protein and block binding.

While not wishing to be held to a single theory underlying the present invention, it is believed that compounds (such as the MA-PSD peptide; SEQ ID NO: 2) that increase MARCKS-related mucus secretion when administered to a mucus-secreting cell may be binding to endogenous proteins in the cell that would otherwise bind to MARCKS protein and inhibit MARCKS from completing a step in the mucus-secretion pathway. Calmodulin is one such endogenous inhibitor of MARCKS; calmodulin binds to MARCKS and prevents phosphorylation, thus preventing the MARCKS protein from disengaging from the plasma membrane. As used herein, "endogenous inhibitors of MARCKS protein" are compounds naturally present in a cell that bind to MARCKS protein and prevent the completion of a step in the MARCKS-related mucus secretion pathway. A peptide or other compound that binds to a MARCKS inhibitor would leave more endogenous MARCKS protein free to function in the mucus secretion pathway. Thus, a method for increasing mucus secretion is to administer to a mucus-secreting cell, a compound that binds to a MARCKS protein inhibitor.

It will be desirable, in many therapeutic situations, to maintain some level of mucus secretion (i.e., a basal or normal level), for the protective effects of mucus. Maintenance of basal mucus secretion may be achieved by regulating the dose of the active compound utilized. Additionally, while not wishing to be held to a single theory of the invention, the present inventors suggest that in some secretory epithelia, a basal level of mucus secretion may be maintained by a pathway separate from the MARCKS-related pathway and stimulated mucus secretion.

The present invention provides methods and compositions able to decrease or reduce mucus hypersecretion that occurs in many pathological conditions, including pathological conditions related to inflammatory, viral, bacterial, or genetic causes. In particular, the present methods and compositions provide methods of treating airway diseases in which mucus secretion is increased over that which occurs in the absence of the disease (i.e., is increased over basal levels, or over normally-occurring levels of mucus secretion). Subjects to be treated by the present methods include human and non-human subjects. Non-human subjects include companion animals such as cats and dogs, as well as livestock such as cattle, horses, sheep and swine.

The present methods and compositions may be used to reduce mucus secretion, or to inhibit mucus hypersecretion, in any secretory epithelium, or epithelial cell, including but not limited to airway epithelial cells (e.g., oral, nasal, bronchial), ocular epithelial cells, gastric or intestinal epithelial cells, and epithelial cells lining the reproductive tract (e.g., vaginal, cervical). As will be apparent to those skilled in the art based on the subject and the condition being treated, it may be desirable to maintain a basal level of mucus secretion, while reducing hypersecretion of mucus. As used herein, a treatment that reduces or inhibits mucus secretion refers to a treatment that reduces the amount of secreted mucus compared to that which would occur in the subject in the absence of such treatment.

The peptides and compounds of the present invention block mucus secretion in response to known activators of PKC and protein kinase G, and to physiologically relevant stimuli (e.g., UTP).

The present invention thus provides methods and compositions for treating epithelial cells or epithelial tissue, where it is desirable to decrease the amount of mucus secreted by those cells or tissue. In particular the present invention provides methods and compositions for treating respiratory conditions where it is desirable to decrease the amount of mucus present in the airways. Conditions suitable for treatment by the present methods include human and animal inflammatory, viral or bacterial airway disease (e.g., asthma, COPD, common cold, rhinitis, acute or chronic bronchitis, pneumonia, and kennel cough), allergic conditions (atopy, allergic inflammation), bronchiectasis, and certain genetic conditions (e.g., cystic fibrosis).

Normal mucus secretion in the lung plays an important role in clearing inhaled foreign particles and pathogens from the airways. Mucus traps inhaled particles, and is then removed from the airways by ciliary action or by coughing. Above-normal levels of mucus secretion (hypersecretion) in the airways can lead to intraluminal mucus accumulation, resulting in airflow obstruction and an increased susceptibility to infectious agents. Secretory cells in the airways include submucosal glands and superficial epithelial mucus cells (goblet cells).

Airway mucus secretion is an important determinant in the prognosis and clinical features of pulmonary diseases. Hypertrophy and/or hyperplasia of airway secretory cells (bronchial glands and epithelial goblet cells) are often found in conditions associated with chronic airway inflammation. In subjects with chronic bronchitis and bronchial asthma, goblet cell hyperplasia has been observed, with a two- to three-fold increase in the numbers of goblet cells compared to controls. Cutz et al., *Histopathology* 2:407-421 (1978), Glynn & Michaels *Thorax* 15:142-153 (1960). Inflammation of the airways may induce mucus hypersecretion by multiple mechanisms, including the release of chemical mediators from surrounding tissues and cells. Airway mucus hypersecretion is a particularly dominant clinical finding in cystic fibrosis, bronchitis, COPD, emphysema, and bronchial asthma. See, e.g., *Airway Secretion*, Takishima and Shimura (Eds.), Marcel Dekker Inc., 1994. The presence of excessive bronchial mucus can lead to bacterial infection and respiratory failure. Lungs of asthmatic patients, at autopsy, often show the presence of excessive bronchial mucus and mucus plugging. Methods of reducing airway mucus secretion would be useful for the treatment of such conditions, as well as in treating bacterial or viral infections (e.g., pneumonia, influenza, and the common cold); in animals, such methods are further useful in treating kennel cough and equine COPD.

Various methods are currently in use to reduce mucus secretion when needed in disease states. Some therapies act to decrease the signals or stimuli that upregulate mucus secretion. For example, inflammatory mediators may upregulate mucus secretion; steroid treatments are often used to decrease inflammation and thus indirectly decrease mucus secretion. Antihistamines are used to block the responses to allergens which can trigger attacks of allergic asthma. The thickened mucus present in patients with cystic fibrosis is removed by compression therapy, and infections occurring due to the thickened mucus are treated with antibiotics. The methods and compounds of the present invention vary from the above treatments in that cellular secretion of mucus in response to a variety of stimuli is directly blocked at the cellular level.

The present invention may be used in a pharmaceutical composition or pharmaceutical formulation comprising a peptide of the invention and a pharmaceutically acceptable carrier.

The present invention may be used in a pharmaceutical composition or pharmaceutical formulation comprising a peptide of the invention and a pharmaceutically acceptable excipient. Suitable excipients will be understood by those skilled in the art and may be found, for example, in the *National Formulary*, 19: 2404-2406 (2000), the disclosure of pages 2404 to 2406 being incorporated herein in their entirety. Examples of suitable excipients include, but are not limited to, starches, gum arabic, calcium silicate, microcrystalline cellulose, methacrylates, shellac, polyvinylpyrrolidone, cellulose, water, syrup, and methylcellulose. The drug product formulations additionally can include lubricating agents such as, for example, talc, magnesium stearate and mineral oil; wetting agents; emulsifying and suspending agents; preserving agents such as methyl- and propyl hydroxybenzoates; sweetening agents; or flavoring agents.

Polyols, buffers, and inert fillers also may be used. Examples of polyols include, but are not limited to, mannitol, sorbitol, xylitol, sucrose, maltose, glucose, lactose, dextrose, and the like. Suitable buffers include, but are not limited to, phosphate, citrate, tartrate, succinate, and the like. Other inert fillers that may be used include those that are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

In certain embodiments, the drug product is present in a solid pharmaceutical composition that may be suitable for oral administration. A solid composition of matter according to the present invention may be formed and may be mixed with and/or diluted by an excipient. The solid composition of matter also may be enclosed within a carrier, which may be, for example, in the form of a capsule, sachet, tablet, paper, or other container. When the excipient serves as a diluent, it may be a solid, semi-solid, or liquid material that acts as a vehicle, carrier, or medium for the composition of matter.

In one aspect, the invention relates to a method of administering a pharmaceutical composition. The pharmaceutical composition comprises a therapeutically effective amount of a known compound and a pharmaceutically acceptable carrier. A "therapeutically effective" amount as used herein is an amount of a compound that is sufficient to ameliorate symptoms exhibited by a subject. The therapeutically effective amount will vary with the age and physical condition of the patient, the severity of the condition of the patient being treated, the duration of the treatment, the nature of any concurrent treatment, the pharmaceutically acceptable carrier used and like factors within the knowledge and expertise of those skilled in the art.

The method of the present invention can be used to reduce (i.e., decrease or attenuate or inhibit) the production of mucus secretions by mucous membranes or mucus-secreting cells, in a subject in need of such treatment. Using methods of administration as are known in the art, the present therapies can be directed to the mucous membranes or mucus-secreting cells of a particular target organ (including but not limited to the oral cavity, nasal cavity, lungs, gastrointestinal tract, eye and reproductive tract), in order to reduce the amount of mucus secreted by, or retained upon, the surfaces being treated. The change (reduction) in mucus is assessed by comparison to that which was present prior to treatment (or in the absence of treatment), or to that which would be expected in the absence of such treatment in view of the subject's condition.

The methods of the present invention may be used in conjunction with other therapies or compounds, including steps to remove retained mucus secretions from the airways of subjects prior to the step of administering the present compounds. This facilitates application of the active agent to the respiratory epithelia during the administering step. Such removal of retained mucus secretions can be carried out by any suitable physical or medicinal means as are known in the art.

Mucosal delivery of peptide-based drugs is discussed in Chien, Novel Drug Delivery Systems, Chapter 4 (Marcel Dekker, 1992); nasal drug delivery is discussed in Chien, supra, in Chapter 5. See also Chang et al., Nasal Drug Delivery, "Treatise on controlled Drug Delivery", Chapter 9 (Marcel Dekker, 1992). Agents known to enhance absorption of drugs through the skin are described in Sloan, Chapter 5, "Prodrugs: Topical and Ocular Drug Delivery" (Marcel Dekker, 1992). The peptides of the present invention can be administered into target cells directly, for example using liposomes. It is expected that those skilled in the art may adapt such techniques and other known drug delivery techniques for use with the compounds of the present invention without undue experimentation.

Precise delivery of the MARCKS-blocking peptide may also overcome any potential limitations of blocking or reducing important secretory processes. Delivering such agents to the respiratory tract should be readily accomplished with inhaled formulations. Since these agents may be useful in treating inflammatory bowel disease, one can envision delivery of the blocking agents into the rectum/colon/intestinal tract via enema or suppositories. Injections or transdermal delivery into inflamed joints may yield relief to patients with arthritic or autoimmune diseases by limiting the secretion from localized inflammatory cells. Injection into areas surrounding nerve endings may inhibit secretion of some types of neurotransmitters, blocking transmission of severe pain or uncontrolled muscle spasms. Delivery of the peptide for the treatment of inflammatory skin diseases should be readily accomplished using various topical formulations known in the art.

Pharmaceutical compositions for use in the present method of treatment include those suitable for inhalation, oral, rectal, vaginal, topical (including buccal, dermal and ocular) administration. The compositions may be prepared by any of the methods well known in the art. The most suitable route of administration in any case will depend upon the location of the tissue to be treated, the nature and severity of the condition being treated, and the particular active compound which is being used, as will be apparent to those skilled in the art.

The present method of treatment of subjects is by the administration of one or more peptides including the MANS peptide or an active fragment thereof described herein. The administration is generally selected from the group consisting of topical administration, parenteral administration, rectal administration, pulmonary administration, inhalation and nasal or oral administration, wherein pulmonary administration generally includes or can be selected from an aerosol, such as an aerosol produced by a dry powder inhaler, a metered dose inhaler, and a nebulizer. The dosage of active compound for treatment of diseases of the respiratory tract will vary depending on the condition being treated and the state of the subject. One skilled in the art would be able to determine appropriate dosages of specific compounds without undue experimentation, using dose response studies as are known in the art. Additionally, the disclosed method may further comprise the administration to the subject of a second molecule selected from the group consisting of an antibiotic, an antiviral compound, an antiparasitic compound, an anti-inflammatory compound, and an immunosuppressant.

The active compounds disclosed herein may be administered to the airways of a subject by any suitable means, but are preferably administered by generating an aerosol comprised of respirable particles, the respirable particles comprised of the active compound, which particles the subject inhales. The respirable particles may be liquid or solid. The particles may optionally contain other therapeutic ingredients. (See, e.g., U.S. Pat. No. 5,849,706 to Molina y Vedia et al.)

In methods of treating the bronchi and/or alveoli, particles comprised of active compound for practicing the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable, especially in human lungs. Particles of non-respirable size which are included in the aerosol tend to deposit in the throat and be swallowed, and the quantity of non-respirable particles in aerosols intended for treatment of the alveoli and/or bronchi is preferably minimized. For nasal administration, a particle size in the range of 10-500 microns is preferred to ensure retention in the nasal cavity.

Liquid pharmaceutical compositions of active compound for producing an aerosol can be prepared by combining the active compound with a suitable vehicle, such as sterile pyrogen free water.

Administration of the active compounds may be carried out therapeutically or prophylactically (e.g., before substantial lung blockage due to retained mucus secretions has occurred, or at a time when such retained secretions have been at least in part removed, as discussed above.)

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, typically water or a dilute aqueous alcoholic solution, and preferably made isotonic with body fluids.

Aerosols of solid particles comprising the active compound may likewise be produced with any solid particulate medicament aerosol generator. One illustrative type of solid particulate aerosol generator is an insufflator. Another is a dry powder inhaler, such as a dry powder inhaler suitable for single dosing use, or a dry powder inhaler suitable for multiple use dosing such as from a reservoir containing sufficient dry powder formulation to provide for repeated dosing or from a dry powder inhaler containing segregated unit doses such as a blister package containing multiple doses.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). Formulations for oral administration may optionally include enteric coatings known in the art to prevent degradation of the formulation in the stomach and provide release of the drug in the small intestine.

To form tablets for oral administration, the composition of matter of the present invention may be made by a direct compression process. In this process, the active drug ingredients may be mixed with a solid, pulverant carrier such as, for example, lactose, saccharose, sorbitol, mannitol, starch, amylopectin, cellulose derivatives or gelatin, and mixtures thereof, as well as with an antifriction agent such as, for example, magnesium stearate, calcium stearate, and polyethylene glycol waxes. The mixture may then be pressed into tablets using a machine with the appropriate punches and dies to obtain the desired tablet size. The operating parameters of the machine may be selected by the skilled artisan. Alternatively, tablets for oral administration may be formed by a wet granulation process. Active drug ingredients may be mixed with excipients and/or diluents. The solid substances may be ground or sieved to a desired particle size. A binding agent may be added to the drug. The binding agent may be suspended and homogenized in a suitable solvent. The active ingredient and auxiliary agents also may be mixed with the binding agent solution. The resulting dry mixture is moistened with the solution uniformly. The moistening typically causes the particles to aggregate slightly, and the resulting mass is pressed through a stainless steel sieve having a desired size. The mixture is then dried in controlled drying units for the determined length of time necessary to achieve a desired particle size and consistency. The granules of the dried mixture are sieved to remove any powder. To this mixture, disintegrating, antifriction, and/or anti-adhesive agents may be added. Finally, the mixture is pressed into tablets using a machine with the appropriate punches and dies to obtain the desired tablet size. The operating parameters of the machine may be selected by the skilled artisan.

If coated tablets are desired, the above prepared core may be coated with a concentrated solution of sugar or cellulosic polymers, which may contain gum arabic, gelatin, talc, titanium dioxide, or with a lacquer dissolved in a volatile organic solvent or a mixture of solvents. To this coating various dyes may be added in order to distinguish among tablets with different active compounds or with different amounts of the active compound present. In a particular embodiment, the active ingredient may be present in a core surrounded by one or more layers including enteric coating layers.

Soft gelatin capsules may be prepared in which capsules contain a mixture of the active ingredient and a liquid vehicle such as, for example, an oil such as a vegetable oil, a fish oil, a synthetic mono-, di- or triglyceride, and combinations thereof. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, and/or gelatin.

Formulations suitable for rectal or vaginal administration may be presented as unit dose suppositories. These may be prepared by admixing the active compound with one or more conventional solid carriers, for example, cocoa butter, and then shaping the resulting mixture.

Formulations suitable for topical application to the eye, mouth, nasal or other surfaces may take the form of an ointment, cream, lotion, paste, gel, spray, aerosol, or oil. Liquid preparations for oral administration may be prepared in the form of syrups or suspensions, e.g. solutions containing an active ingredient, sugar, and a mixture of ethanol, water, glycerol, and propylene glycol. If desired, such liquid preparations may comprise one or more of following: coloring agents, flavoring agents, and saccharin. Thickening agents such as carboxymethylcellulose also may be used. In the event that the above pharmaceuticals are to be used for parenteral administration, such a formulation may comprise sterile aqueous injection solutions, non-aqueous injection solutions, or both, comprising the composition of matter of the present invention. When aqueous injection solutions are prepared, the composition of matter may be present as a water soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may comprise suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

The composition of matter also may be formulated such that it may be suitable for topical administration (e.g., skin cream). These formulations may contain various excipients known to those skilled in the art. Suitable excipients may include, but are not limited to, cetyl esters wax, cetyl alcohol, white wax, glyceryl monostearate, propylene glycol, monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

The myristoylated alanine-rich C kinase substrate (MARCKS) protein is a major cellular substrate for protein kinase C. MARCKS is regulated in a cell-, tissue- and developmental stage-specific manner, and expression of MARCKS can be stimulated by various cytokines. MARCKS has been identified in human, bovine, rodent and avian species. Harlan et al., *J. Biol. Chem.* 266:14399 (1991); Graff et al., *J. Biol. Chem.* 266:14390 (1991); Graff et al., *Mol. Endocrinol.* 3:1903 (1989); Stumpo et al., *Proc. Natl. Acad. Sci. USA* 86:4012-16 (June 1989). It is known that MARCKS protein is post-translationally myristoylated by replacing the initiation methionine at its N-terminus with a myristic acid which results in the myristic acid directly attaching to an N-terminal glycine. The enzyme, myristoyl CoA:protein N-myristoyltransferase (NMT), catalyzes the addition of myristic acid to the amino terminal glycine residues of a number of eukaryotic proteins. Towler et al., Proc. Natl. Acad. Sci. USA 84: 2708-2712, (1987), discloses that the methionine residue is removed prior to myristoylation. Additionally, Vergeres et al., Biochem J. 330: 5-11 (1998) discloses that the N-terminal glycine residue of MARCKS proteins is myristoylated via a reaction catalyzed by myristoyl CoA:protein N-myristoyl transferase (NMT) and that the myristoyl group is involved in membrane binding. Thus, the mature MARKCS protein begins with a myristoylated glycine amino acid residue as does the MANS peptide which is the first 24 amino acids of the human MARCKS protein.

The present inventors have identified specific active fragments of MARCKS protein that are able to affect mucus secretion. A myristoylated polypeptide, 24 amino acids in length, with sequence Myristic acid-GAQFSK-TAAKGEAAAERPGEAAVA (SEQ ID NO:1), is abbreviated and referred to herein as the MANS peptide for the myristoylated N-terminal sequence. Additionally, N-terminal myristoylated active fragments of MANS peptide (i.e., SEQ ID NOS: 2 through 20) are also useful for reducing mucus hypersecretion. These peptides inhibit secretion of mucus from mucous membranes and mucus-secreting cells, including human airway epithelial cells and inhibit inflammation by attenuating release of granular contained inflammatory mediators from inflammatory cells. The present inventors' data suggest that this MANS peptide blocks the attachment of MARCKS protein to the mucin granule, thus blocking or inhibiting the release of mucin granules and the secretion of mucus by the cell.

A second peptide corresponding to the PSD (phosphorylation) site of MARCKS was also tested. At some concentrations this peptide stimulates mucus secretion, while at other doses (higher) it has no effect on stimulated secretion (e.g., see Example 9), and it is predicted that even higher doses will decrease stimulated mucus secretion. The PSD peptide sequence is myristic acid—KKKKKRFSFKKSFKLSGFS-FKKNKK (SEQ ID NO: 25), referred to herein as the MA-PSD peptide. While not wishing to be held to a single theory underlying the present invention, the inventors believe that MARCKS protein fragments that are able to increase mucus secretion (such as the MA-PSD peptide, SEQ ID NO: 25) may be binding to endogenous proteins in the cell that competitively inhibit the phosphorylation of MARCKS, thus inhibiting the release of MARCKS from the plasma membrane into the cell interior (see FIG. 1). One such inhibitor of MARCKS phosphorylation is calmodulin. Other "MARCKS inhibitors", for purposes of the present invention, are those endogenous compounds that prevent the MARCKS protein from completing a necessary step in the mucus-secretion pathway. MARCKS inhibitors may thus act to inhibit the phosphorylation or the dephosphorylation of MARCKS (each of which is necessary in the present pathway), or bind to MARCKS to prevent its binding to the mucin granule membrane. Compounds of the present invention that increase the secretion of mucus may be acting by binding to such endogenous inhibitors, thus freeing endogenous MARCKS protein to complete the mucus-secretion pathway.

Thus, peptide fragments of the MARCKS protein may be designed, tested and selected for their ability to inhibit or enhance mucus secretion, using the present disclosure and methods known in the art.

The nucleotide and amino acid sequences of human MARCKS cDNA and protein as reported by Harlan et al., *J. Biol. Chem.* 266:14399 (1991) (GenBank Accession No. M68956) are provided as SEQ ID NO: 21 and SEQ ID NO: 22. The nucleotide and amino acid sequences of human MARCKS cDNA and protein as reported by Sakai et al., Genomzics 14:175 (1992) are provided as SEQ ID NO: 23 and SEQ ID NO: 24. An additional publication (Harlan et al., *J. Biol. Chem.* 266(22):14399 (1991) provides a nucleotide sequence for human MARCKS that differs from that of Sakai et al. at nucleotides 619 and 724; in this sequence, G is substituted for T at position 619 and C is substituted for G at position 724. Additional allelic variants of human and other MARCKS proteins would be expected.

While not wishing to be held to a single theory underlying the present invention, the present inventors propose that the pathway for the involvement of MARCKS in mucus secretion in airway epithelium is as shown in FIG. 1. It is currently believed that active peptide fragments of MARCKS affect mucus secretion at the level of the interaction of MARCKS with the mucin granules, which contain the major protein components of mucus. As shown in FIG. 1, the present inventors believe that MARCKS must be dephosphorylated to bind to the mucin granule, which triggers mucin exocytosis and results in mucus secretion.

The methods of the present invention include the use of isolated DNA molecules encoding the peptides of the present invention. Such isolated DNA molecules are useful in producing the therapeutic peptides, and may additionally be used in an appropriate gene expression vector for gene therapy, using methods as are known in the art for the expression of the peptide in vivo. Cell-specific or inducible promoters may further be used to control the expression of the therapeutic peptide in vivo. Methods of delivering DNA encoding a desired peptide to achieve a therapeutic effect is disclosed, e.g. in U.S. Pat. Nos. 5,580,859 and 5,703.055 to Felgner et al.

Analogs of the therapeutic peptides disclosed herein are an aspect of the present invention. As used herein, an "analog" is a chemical compound similar in structure to a first compound, and having a similar physiologic action as the first compound. With particular reference to the present invention, MARCKS peptide analogs are those compounds which, while not having the exact amino acid sequences of the native MARCKS fragment, are capable of binding to the same sites as the native MARCKS fragment. Such analogs may be peptide or non-peptide analogs, including nucleic acid analogs, as described in further detail below.

In protein and peptide molecules which interact with a receptor, the interaction between the protein and the receptor must take place at surface-accessible sites in a stable three-dimensional molecule. By arranging the critical binding site residues in an appropriate conformation, peptides which mimic the essential surface features of the p20 ligands may be designed and synthesized in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, Science, 247, 28029 (1990); Rossmann, Nature, 333, 392-393 (1988); Weis et al., Nature, 333, 426-431 (1988); James et al. Science, 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met. preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg, preferably with Arg; Arg may be replaced with Lys, Asp or Glu, preferably Lys; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules which bind to sites bound by the native MARCKS fragments disclosed herein. See, e.g., Knight, BIO/Technology, 8, 105 (1990). Itzstein et al, Nature, 363, 418 (1993); Lam et al, Science, 263, 380 (January 1994) (rational design of bioavailable nonpeptide cyclic ureas that function as HIV protease inhibitors). Analogs may also be developed by generating a library of molecules, selecting for those molecules which act as ligands for a specified target, and identifying and amplifying the selected ligands. See, e.g., Kohl et al., Science, 260, 1934 (1993). Techniques for constructing and screening combinatorial libraries of oligomeric biomolecules to identify those that specifically bind to a given receptor protein are known. Suitable oligomers include peptides, oligonucleotides, carbohydrates, non-oligonucleotides (e.g., phosphorothioate oligonucleotides; see Chem. and Engineering News, page 20, 7 Feb. 1994) and nonpeptide polymers (see, e.g., "peptoids" of Simon et al., Proc. Natl. Acad. Sd. USA, 89, 9367 (1992)). See also U.S. Pat. No. 5,270,170 to Schatz; Scott and Smith, Science, 249, 386-390 (1990); Devlin et al., Science 249, 404-406 (1990); Edgington, BIO/Technology, 11, 285 (1993). Peptide libraries may be synthesized on solid supports, or expressed on the surface of bacteriophage viruses (phage display libraries). Known screening methods may be used by those skilled in the art to screen combinatorial libraries to identify suitable peptide analogs. Techniques are known in the art for screening synthesized molecules to select those with the desired activity, and for labelling the members of the library so that selected active molecules may be identified. See, e.g., Brenner and Lerner, Proc. Natl. Acad. Sci. USA, 89, 5381 (1992); PCT U593/06948 to Berger et al.; Simon et al., Proc. Natl. Acad. Sci. USA, 89, 9367, (1992); U.S. Pat. No. 5,283,173 to Fields et al.

As used herein, "combinatorial library" refers to collections of diverse oligomeric biomolecules of differing sequence, which can be screened simultaneously for activity as a ligand fbr a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. (See, e.g., Edgington, BIO/Technology, 11, 285 (1993).) U.S. Pat. No. 5,270,163 to Gold and Tuerk describes a method for identifying nucleic acid ligands for a given target molecule by selecting, from a library of RNA molecules with randomized sequences, those molecules that bind specifically to the target molecule. A method for the in vitro selection of RNA molecules immunologically cross-reactive with a specific peptide is disclosed in Tsai, Kenan and Keene, Proc. Nail. Acad. Sci. USA, 89, 8864 (1992) and Tsai and Keene, J. Immunology, 150, 1137 (1993).

The present inventors have further demonstrated that antisense oligonucleotides directed against MARCKS mRNA decreases (inhibits) mucus secretion in human airway epithelial cells. (See Example 10).

It has been demonstrated that antisense oligonucleotides that are complementary to specific RNAs can inhibit the expression of cellular genes as proteins. See Erickson and Izant, Gene Regulation: Biology Of Antisense RNA And DNA, Vol. 1, Raven Press, New York, 1992. For example, selective inhibition of a p21 gene that differed from a normal gene by a single nucleotide has been reported. Chang et al., Biochemistry 1991, 30:8283-8286. Many hypotheses have been proposed to explain the mechanisms by which antisense oligonucleotides inhibit gene expression, however, the specific mechanism involved may depend on the cell type studied, the RNA targeted, the specific site on the RNA targeted, and the chemical nature of the oligonucleotide. Chiang et al., J. Biol. Chem. 1991, 266:18162-18171; Stein and Cohen, Cancer Res. 1988, 48:2659-2668.

The present invention provides oligonucleotides substantially complementary to a MARCKS protein nucleotide sequence that occurs endogenously in a mucus-secreting cell.

Such oligonucleotides are useful in decreasing mucus production by cells into which they are delivered. "Nucleotide sequence" refers to a polynucleotide formed from a series of joined nucleotide units. The term "substantially complementary", as used herein, refers to that amount of sequence complementarity between the oligonucleotide and a MARCKS gene nucleotide sequence which allows for interstrand hybridization under physiological conditions and enables the oligonucleotide to inhibit the expression of the MARCKS gene. Interstrand hybridization is the interaction between the oligonucleotide and the MARCKS nucleotide sequence. The potential of forming a stable interstrand hybrid can be determined by those skilled in the art using methods known in the art, such as, for example, determination of the melting temperature for the hybrid by mathematical modeling or empirical analysis, or solid support nucleic acid hybridizations. (See. e.g., Marmur and Doty, *J. Mol. Biol.* 1962, 5, 113).

Antisense DNAs used in the present invention are able to produce the corresponding antisense RNAs. An antisense RNA molecule has the nucleotide bases in the reverse or opposite order for expression. Such antisense RNAs are well known in the art, see e.g., U.S. Pat. No. 4,801,540 to Calgene Inc.

As used herein, the term "MARCKS nucleotide sequence" refers to any nucleotide sequence derived from a gene encoding a MARCKS protein, including, for example, DNA or RNA sequence, DNA sequence of the gene, any transcribed RNA sequence, RNA sequence of the pre-mRNA or mRNA transcript, and DNA or RNA bound to protein.

Oligonucleotides targeted to sequences in MARCKS genes can be used to inhibit mucus production in epithelial cells. The oligonucleotide may be any length of sequence capable of forming a stable hybrid with the endogenous MARCKS nucleotide sequence under physiologic conditions. It is preferred that the length of the oligonucleotide be between 5 and 200 nucleotides. It is more preferred that the oligonucleotide be between and 50 nucleotides in length. It is most preferred that the oligonucleotide be between 15 and 25 nucleotides in length.

The nucleotides of the oligonucleotides may be any known in the art including natural and synthetic moieties. The term "oligonucleotide" as used herein refers to a polynucleotide formed from joined nucleotides. Moreover, the term "oligonucleotide" includes naturally occurring oligonucleotides or synthetic oligonucleotides formed from naturally occurring subunits or analogous subunits designed to confer special properties on the oligonucleotide so that it is more stable in biological systems or binds more tightly to target sequences. It also includes modifications of the oligonucleotides such as chemically linking them to other compounds that will enhance delivery to cells or to the nucleus and other compartments of cells. Oligonucleotides of the invention may be synthesized by any method known in the art, including synthetic chemical methods. See, e.g., Vu and Hirschbein. *Tetrahedron Lett.* 1991, 32:30005-30008. Oligonucleotides may be modified via chemical methods known to those skilled in the art, including encapsulation in liposomes, or chemical linkage to steroids, antibodies, and cell receptors.

A preferred embodiment of the invention is an oligonucleotide complementary to an endogenous MARCKS nucleotide sequence found in the cell to be treated, or having sufficient complementarity to allow stable interstrand hybridization between the oligonucleotide and an endogenous MARCKS nucleotide, and that inhibits the expression of the MARCKS gene. A preferred oligonucleotide is one that is complementary to a MARCKS nucleotide sequence derived or selected from a mammal, in particular, a human.

The oligonucleotides of the present invention may be oligodeoxyribonucleotides or oligoribonucleotides, including modified oligodeoxynucleotides and oligoribonucleotides. Moreover, the oligonucleotides of the invention may be comprised of combinations of deoxyribonucleotides and ribonucleotides. Further, oligonucleotides of the invention may also include modified subunits. For example, the invention may include phosphorothioate oligodeoxyribonucleotides. It is preferred that the oligonucleotides of the invention be modified to increase stability and prevent intracellular and extracellular degradation. It is more preferred that the oligonucleotides of the invention be modified to increase their affinity for target sequences, and their transport to the appropriate cells and cell compartments when they are delivered into a mammal in a pharmaceutically active form.

It is preferred that the oligonucleotides of the invention be antisense oligonucleotides. The oligonucleotides of the invention may be targeted to a non-coding portion of a MARCKS or targeted to coding sequences of the gene, and may include an intron-exon junction (i.e., several nucleotides on either or both sides of the intron-exon junction).

The oligonucleotides of the invention may be administered by any method that produces contact of the oligonucleotide with the target tissue or cell in the subject being treated, including but not limited to oral administration, topical administration, and inhalation. The pharmaceutical compositions comprising the oligonucleotides may be in solid dosage forms, such as capsules, tablets, and powders, or in liquid dosage forms, such as elixirs, syrups, and suspensions. The dosage administered varies depending upon factors such as: pharmacodynamic characteristics; its mode and route of administration; age, health, and weight of the recipient; nature and extent of symptoms; kind of concurrent treatment; and frequency of treatment and the effect desired. Effective dosages are those which are able to inhibit mucus production in the airways at a level which alleviates, reduces, or eliminates the symptoms or conditions associated with the mucus production.

The oligonucleotides may be administered singly, or in combination with other compounds of the invention, other pharmaceutical compounds, or therapies. The oligonucleotides are preferably administered with a pharmaceutically acceptable carrier or diluent selected on the basis of the selected route of administration and standard pharmaceutical practice.

Inhibition of secretion of mucus, via inhibition of MARCKS protein function in epithelial secretory cells, is a focus of this invention. To achieve this end, the invention provides methods of inhibiting mucus secretion which comprises contacting a mucus-secretory cell with a MARCKS gene expression inhibitory amount of an oligonucleotide substantially complementary to an endogenous MARCKS gene nucleotide sequence. The invention also includes a method whereby the contacting step comprises lipofectin as a carrier for the oligonucleotide. The oligonucleotides of the invention are administered to mammals or avians, and preferably to humans, in therapeutically effective amounts or concentrations which are effective to inhibit or reduce mucus production in the target tissue or organ.

The oligonucleotides of the invention will be capable of reaching their intracellular target to inhibit or reduce the expression of MARCKS protein therein. The invention therefore provides methods of inhibiting mucus secretion which comprise contacting at least one element of MARCKS gene expression machinery with a gene expression inhibitory amount of an oligonucleotide. For the purposes of the invention, the elements of the gene expression machinery may comprise any nucleotide sequence of a MARCKS gene, the nucleotide sequence of spliced mRNAs transcribed from a gene, unspliced RNAs and partially spliced RNAs transcribed from a gene, DNA-RNA hybrids comprising sequence derived from a gene, such as in actively transcribing genes, RNA transcribed from a gene bound to protein, and any molecule or structure known in the art to be involved in gene expression.

U.S. Pat. No. 5,858,784 to Debs et al. provides a method of administering nucleic acids to the lung cells of a subject by preparing a liposome-nucleic acid mixture suitable for nebulization, nebulizing the mixture, and depositing the resulting nebulized mixture in the lungs of the subject. The nucleic acid sequence may include DNA sequences which encode polypeptides which are directly or indirectly responsible for a therapeutic effect, or active nucleotide sequences such as antisense sequences and ribozymes. The nucleic acid constructs can be provided to the cells of the subject as expression cassettes; preferably, the construct does not become integrated into the host cell genome and is introduced into the host as part of a non-integrating expression vector. (The disclosures of all US patents cited herein are intended to be incorporated herein in their entirety.)

It has recently been shown that the introduction of exogenous double-stranded RNA (dsRNA) can specifically disrupt the activity of genes containing homologous sequences, possibly by post-transcriptional effects. Montgomery et al., *Proc. Natl. Acad. Sci. USA* 95:15502 (1998); Ngo et al., *Proc. Natl. Acad. Sci. USA* 95:14687 (1998). Accordingly, the methods of the present invention may be carried out by introducing exogenous dsRNA into a mucus-secreting cell, where the dsRNA has sufficient sequence similarity to the RNA of an endogenous MARCKS gene to result in a reduction in MARCKS protein in the cell (compared to that which would occur in the absence of the exogenous dsRNA).

The administration of dsRNA may be carried out using the methods discussed above regarding peptide and antisense oligonucleotide administration.

In an alternate embodiment of the present invention, DNA encoding an enzymatic RNA molecule (ribozyme) may be introduced into the target cell. Ribozymes are directed against and cleave the mRNA transcript of the cell's endogenous MARCKS protein. DNA encoding enzymatic RNA molecules may be produced in accordance with known techniques (see e.g., U.S. Pat. No. 4,987,071. Production of such an enzymatic RNA molecule and disruption of MARCKS protein production affects mucus production by the target cell in essentially the same manner as production of an antisense RNA molecule.

The present invention also provides a method of screening compounds for their ability to affect (inhibit) mucus production. Combinatorial chemistry processes as are known in the art may be used to generate large numbers of structurally diverse compounds, which can then be screened. Such screening methods comprise providing a culture of mucus-secreting cells, such as the cultures of normal human bronchial epithelial cells described herein. A test compound is administered to the cells, and the cells may also be exposed to a compound known to stimulate mucus production (e.g., PMA, UTP, 8-bromo-cGMP). The test compound and the stimulatory compound may be administered to the cells, for example, by exposing the cells to media containing the compounds. The cells may, for example, be pre-incubated with the test compound first, then co-incubated with the stimulatory compound and the test compound. Alternatively, the pre-incubation step may be omitted. The ability of the test compound to bind to either the mucin granule membrane (or a mucin granule membrane-related receptor) or to endogenous MARCKS protein at the mucin granule membrane binding site is assessed by detecting whether the test compound inhibits binding of endogenous MARCKS to the mucin granule. Such detection can be carried out using methods known in the art, for example, by labelling the test compound with a detectable molecule.

Molecules detectable by spectroscopic, photochemical, biochemical, immunochemical, electrical and optical means are known. Optically detectable molecules include fluorescent labels (fluorescein, Texas Red, Green Fluorescent Protein). Methods for viewing intact cells are known, including real-time confocal laser-scanning microscopy and two-photon laser-scanning microscopy.

Mucus secreted by the cells may also be measured after a pre-determined time period, for example using an ELISA assay as is known in the art. The mucus secretion of the cells exposed to the test compound can also be compared to that of control cells that were not exposed to the test compound. A decrease in mucus secretion by the test cells compared to the control cells indicates that the test compound inhibits mucus secretion, and an increase in mucus secretion by the test cells compared to the control cells indicates that the test compound enhances mucus secretion.

The following are described in greater detail in the Examples below: Inhibition of release of myeloperoxidase (MPO) from human neutrophils; Inhibition of Eosinophil peroxidase Release from HL-60 Cells; Inhibition of Lysozyme Release from U937 Cells; Inhibition of LPS-induced lung inflammation; LPS model for inflammation; Neutrophil chemotactic migration assay; and Ozone mouse model for COPD.

In one embodiment, this invention discloses a method of regulating an inflammation in a subject comprising administering a therapeutically effective amount of a pharmaceutical composition comprising a MANS peptide or an active fragment thereof. In one aspect of this embodiment, said active fragment of the MANS protein comprises at least six amino acids. In another aspect, said inflammation is caused by respiratory diseases, bowel diseases, skin diseases, autoimmune diseases and pain syndromes. In another aspect, said respiratory diseases are selected from the group consisting of asthma, chronic bronchitis, and COPD. In another aspect, said bowel diseases are selected from the group consisting of ulcerative colitis, Crohn's disease and irritable bowel syndrome. In another aspect, said skin diseases are selected from the group consisting of rosacea, eczema, psoriasis and severe acne. In another aspect, said inflammation is caused by arthritis or cystic fibrosis. In another aspect, said subject is a mammal. Additionally, in another aspect, said mammal is selected from the group consisting of humans, canines, equines and felines. In another aspect, said administering step is selected from the group consisting of topical administration, parenteral administration, rectal administration, pulmonary administration, nasal administration, inhalation and oral administration. In another aspect, said pulmonary administration comprises use of an aerosol, which can be generated using a device selected from the group of a dry powder inhaler, a metered dose inhaler, and a nebulizer.

In another embodiment, this invention discloses a method for regulating a cellular secretory process in a subject comprising administering a therapeutically effective amount of a pharmaceutical composition comprising at least one compound comprising a MANS peptide or an active fragment thereof, that regulates an inflammatory mediator in a subject.

In one aspect of this embodiment, said active fragment of the MANS protein comprises at least six amino acids. In another aspect, said regulating a cellular secretory process is blocking or reducing a cellular secretory process. In another aspect, said inflammatory mediator is caused by respiratory diseases, bowel diseases, skin diseases, autoimmune diseases and pain syndromes. In another aspect, said respiratory diseases are selected from the group consisting of asthma, chronic bronchitis, and COPD. In another aspect, said bowel diseases are selected from the group consisting of ulcerative colitis, Crohn's disease and irritable bowel syndrome. In another aspect, said skin diseases are selected from the group consisting of rosacea, eczema, psoriasis and severe acne. In another aspect, said inflammatory mediator is caused by arthritis or cystic fibrosis. In another aspect, said subject is a mammal. In another aspect, said mammal is selected from the group consisting of humans, canines, equines and felines. In another aspect, said administering step is selected from the group consisting of topical administration, parenteral administration, rectal administration, pulmonary administration, nasal administration, inhalation and oral administration. In another aspect, said pulmonary administration is selected from the group of an aerosol produced from a dry powder inhaler, an aerosol produced from a metered dose inhaler, and an aerosol produced from a nebulizer.

In another embodiment, this invention discloses a method of reducing inflammation in a subject comprising administering a therapeutically effective amount of a compound that inhibits the MARCKS-related release of inflammatory mediators, whereby the release of inflammatory mediators in the subject is reduced compared to that which would occur in the absence of said treatment. In one aspect of this embodiment, said compound is at least one active fragment of a MARCKS protein. In another aspect, said active fragment is at least six amino acids in length. In another aspect, said compound is a MANS peptide or an active fragment thereof. In another aspect, said compound is an antisense oligonucleotide directed against the coding sequence of a MARCKS protein or an active fragment thereof. In another aspect, said active fragment is at least six amino acids in length.

In another embodiment, this invention discloses a method of reducing inflammation in a subject comprising administering a therapeutically effective amount of a pharmaceutically active composition comprising a compound that inhibits the MARCKS-related release of inflammatory mediators, whereby the inflammation in the subject is reduced compared to that which would occur in the absence of said treatment. In one aspect of this embodiment, said compound is an active fragment of a MARCKS protein. In another aspect, said active fragment is at least six amino acids in length. In another aspect, said compound is a MANS peptide or an active fragment thereof. In another aspect, said compound is an antisense oligonucleotide directed against the coding sequence of a MARCKS protein or an active fragment thereof. The present invention is intended to encompass a composition that contains one or more of the MANS peptide or its active fragments and use thereof in the treatment of inhibiting the release of inflammatory mediators from granules or vesicles of inflammatory cells.

In another embodiment, this invention discloses a method of regulating mucin granule release in a subject comprising administering a compound that regulates mucin granule release, whereby release from said mucin granules is reduced as compared to that which would occur in the absence of said compound. In one aspect of this embodiment, said compound is an active fragment of a MARCKS protein. In another aspect, said compound is a MANS peptide.

In another embodiment, this invention discloses a method of regulating exocytotic secretion of airway mucin granules in a subject comprising: administering a compound that regulates mucin granule release, whereby release from said mucin granules is reduced as compared to that which would occur in the absence of said compound. In one aspect of this embodiment, said compound is an active fragment of a MARCKS protein. In another aspect, said compound is a MANS peptide.

In another embodiment, this invention discloses a method of modulating mucus secretion in a cell of a subject comprising: administering a therapeutic amount of an antisense sequence that are complementary to sequences encoding a MARCKS protein or an active fragment thereof, wherein mucus secretion by said cell is inhibited compared to that which would occur in the absence of such administration. In one aspect of this embodiment, said sequence is at least eighteen nucleic acids in length. In another aspect, said compound is complementary to sequences encoding a MANS peptide or an active fragment thereof. In another aspect, said modulating mucus secretion is blocking or reducing mucus secretion.

In another embodiment, this invention discloses a method of reducing or inhibiting inflammation in a subject comprising administering a therapeutically effective amount of at least one peptide comprising MANS peptide or an active fragment thereof effective to modulate an inflammatory mediator at the inflammation site. In one aspect of this embodiment, said active fragment is at least six amino acids in length. In another aspect, said inflammatory mediator is produced by cells selected from the group consisting of neutrophils, basophils, eosinophils, monocytes and leukocytes. Preferably the cells are leukocytes, more preferably granulocytes, and even more preferably neutrophils, basophils, eosinophils or a combination thereof. In another aspect, the agent is administered orally, parenterally, cavitarily, rectally or through an air passage. In another aspect, said composition further comprises a second molecule selected from the group consisting of an antibiotic, an antiviral compound, an antiparasitic compound, an anti-inflammatory compound, and an immunosuppressant.

In another aspect, the methods disclosed in this invention can be accomplished by use of or administration of combinations of the peptides disclosed herein, i.e., by use of or administering of a N-terminal myristoylated peptide fragment of at least 5 or at least 6 contiguous amino acids of the MANS peptide (SEQ ID NO: 1), which N-terminal myristoylated peptide fragment is selected from the group consisting of N-myristoyl-GAQFSKTAAKGEAAAERPGEAAV (SEQ ID NO: 2); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKAAKGIEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO:14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); N-myristoyl-GAQFSK (SEQ ID NO: 19); and N-myristoyl-GAQFS (SEQ ID NO: 20), and combinations thereof. Preferably a single peptide is used or administered in the methods disclosed herein.

In response to protein kinase C (PKC) activation by an inflammatory stimulant, degranulation in a cell selected from the group consisting of neutrophils, eosinophils, monocytes/macrophages and lymphocytes can be attenuated by pre-incubation and by co-incubation with a peptide identical to the N-terminal region of MARCKS protein, wherein the peptide is selected from the group consisting of the MANS peptide (SEQ ID NO: 1) and myristoylated N-terminal fragments thereof (SEQ ID NOS: 2 through 20). Although time courses and concentrations can vary among cell types, in all cases the MANS peptide attenuates PKC-induced degranulation.

Having now described the invention, the same will be illustrated with reference to certain examples, which are included herein only to more fully illustrate the present invention, and which are not intended to be limiting of the invention.

EXAMPLES

Example 1

Mucin Hypersecretion from NHBE Cells Involves Activation of Both PKC and PKG

This example demonstrates that mucin hypersecretion by NHBE cells is maximized by activation of both PKC and PKG.

To determine the potential role of PKC and/or PKG in the mucin secretory process, NHBE cells were exposed to the following two specific protein kinase activators: the phorbol ester, phorbol 12-myristate 13-acetate (PMA), for activation of PKC, and the nonhydrolyzable cGMP analogue, 8-Br-cGMP, for activation of PKG. Preliminary studies examining mucin secretion in response to PMA stimulation at various concentrations for different times (up to 1 micromolar ($\mu$M) for 2 h) indicated that activation of PKC alone did not induce significant mucin secretion from NHBE cells, although a moderate secretory response was repeatedly observed at PMA concentrations higher than 100 nM ($0.05 < p < 0.1$). Also, the cells did not respond to the cGMP analogues at concentrations as high as 500 $\mu$M for up to 2 h of exposure. However, a combination of PMA+8-Br-cGMP, affecting dual activation of PKC and PKG, provoked a rapid increase in secretion, approximately doubling it within 15 min of exposure (see Results-I-1A).

Results-I-1A: Mucin secretion as % of control (i.e., medium alone) was found as follows:

I-1A-1: medium (control), gave mucin secretion as percent of control normalized as 100%;

I-1A-2: DMSO (0.1%), (vehicle) gave mucin secretion as percent of control=106%;

I-1A-3: 4-alpha-PMA (100 nM), negative control for phorbol ester PMA, gave mucin secretion as percent of control=104%;

I-1A-4: PMA (100 nM), a PCK activator, gave mucin secretion as percent of control=123% (#);

I-1A-5: 8-Br-cGMP (1 $\mu$M), a PKG activator, gave mucin secretion as percent of control=109%;

I-1A-6: 4-alpha-PMA (100 nM)+8-Br-cGMP (1 $\mu$M), gave mucin secretion as percent of control=111%;

I-1A-7: PMA (100 nM)+8-Br-cGMP (1 $\mu$M), gave mucin secretion as percent of control=211% (*);

I-1A-8: Rp-8-Br-PET-cGMP (1 $\mu$M), a PKG inhibitor, gave mucin secretion as percent of control=102%

I-1A-9: PMA (100 nM)+Rp-8-Br-PET-cGMP (1 $\mu$M), gave mucin secretion as percent of control=117%

I-1A-10: Rp-8-Br-cGMP (1 $\mu$M), a PKG inhibitor and a cGMP-gated ion channel activator, gave mucin secretion as percent of control=100%

I-1A-11: PMA (100 nM)+Rp-8-Br-cGMP (1 $\mu$M), gave mucin secretion as percent of control=123%.

This secretory response induced by PMA+8-Br-cGMP was concentration-dependent, with maximal stimulation at 100 nM PMA+1 $\mu$M 8-Br-cGMP (see Results-I-1B and Results-I-1C).

Results-I-1B: Mucin secretion as % of control in the presence of increasing amounts of 8-Br-cGMP ($\mu$M)+constant amount of PMA (100 nM).

I-1B-1: control, gave mucin secretion which was normalized as percent of control=100%;

I-1B-2: PMA (100 nm)+8-Br-cGMP (0.01 $\mu$M), gave mucin secretion as percent of control=132%;

I-1B-3: PMA (100 nm)+8-Br-cGMP (0.1 $\mu$M), gave mucin secretion as percent of control=168% (*);

I-1B-4: PMA (100 nm)+8-Br-cGMP (1 $\mu$M), gave mucin secretion as percent of control=235% (*);

I-1B-5: PMA (100 nm)+8-Br-cGMP (10 $\mu$M), gave mucin secretion as percent of control=224% (*);

I-1B-6: PMA (100 nm)+8-Br-cGMP (100 $\mu$M), gave mucin secretion as percent of control=232% (*);

I-1B-7: PMA (100 nm)+8-Br-cGMP (500 $\mu$M), gave mucin secretion as percent of control=244% (*).

Results-I-1C: Mucin secretion as % of control in the presence of increasing amounts of PMA (nM)+constant amount of 8-Br-cGMP (1 $\mu$M)

I-1C-1: control, gave mucin secretion which was normalized as percent of control=100%;

I-1C-2: PMA (1 nM)+8-Br-cGMP (1 $\mu$M), gave mucin secretion as percent of control=121%;

I-1C-3: PMA (10 nM)+8-Br-cGMP (1 $\mu$M), gave mucin secretion as percent of control=172%;

I-1C-4: PMA (100 nM)+8-Br-cGMP (1 $\mu$M), gave mucin secretion as percent of control=224%;

I-1C-5: PMA (1000 nM)+8-Br-cGMP (1 $\mu$M), gave mucin secretion as percent of control=229%.

Results-I-1D: Mucin secretion as % of control in the presence of UTP (100 $\mu$M) of selected inhibitors as identified below.

I-1D-a: control, in the absence of UTP (100 $\mu$M), gave mucin secretion which was normalized as percent of control=100%;

I-1D-b: control, in the presence of UTP (100 $\mu$M), gave mucin secretion as percent of control=159% (*);

I-1D-1: Calphostin C (500 nM), a PKC inhibitor, gave mucin secretion as percent of control=120% (‡);

I-1D-2: Rp-8-Br-PET-cGMP (10 $\mu$M), a PKG inhibitor, gave mucin secretion as percent of control=129% (‡);

I-1D-3: LY83583 (50 $\mu$M), a GC-S inhibitor, gave mucin secretion as percent of control=111% (‡);

I-1D-4: KT5720 (500 nM), a PKA inhibitor, gave mucin secretion as percent of control=157% (*).

In Results-I-1A, in Results-I-1B, and in Results-I-1C, NHBE cells were exposed to indicated reagent(s) or medium alone (CTL; i.e., control) for 15 min.

In Results-I-1D, NHBE cells were preincubated with the indicated inhibitor for 15 min and then stimulated with 100 $\mu$M UTP for 2 h. Secreted mucin in response to the treatment was collected and assayed by ELISA. Data are presented as mean±S.E. (n=6 at each point). The (*) stands for significantly different from medium control ($p < 0.05$); (#) stands for different from medium control (0.05<p<0.1); and (1) stands for significantly different from UTP stimulation CD<0.05).

UTP is a well defined pathophysiologically relevant mucin secretagogue. Lethem ct al., Am. J. Respir. Cell Mol. Biol. 9, 315-322 (1993). The present invention further demonstrates that UTP, at various concentrations, preferably 40 to 140 µM, may induce a significant increase in mucin secretion from NHBE cells after a 2 h exposure. To determine whether PKC and PKG were involved in regulation of mucin secretion in response to a pathophysiological stimulus, effects of PKC/PKG inhibitors on UTP-induced mucin secretion were investigated. NHBE cells were preincubated with various inhibitors for 15 min and then exposed to UTP (100 µM) plus the inhibitor for 2 h. The secreted mucin was measured by ELISA. The results indicated that mucin secretion provoked by UTP may require both PKC and PKG activities, as the secretory response was attenuated independently by the PKC inhibitor calphostin C (500 nM), the PKG inhibitor Rp-8-Br-PET-cGMP (10 µM), or the soluble guanylyl cyclase (GC-S) inhibitor LY83583 (50 µM) but likely not by the protein kinase A (PKA) inhibitor KT5720 (500 nM) (see Results-I-1D). Apparently, mucin secretion in NHBE cells may be regulated by a signaling mechanism involving both PKC and PKG.

To address involvement of PKG in the secretory process, 8-Br-cGMP was utilized in these studies. Although the primary physiological effect of 8-Br-cGMP is to activate PKG, it also has been reported to act as an agonist for cGMP-gated ion channels in some cells and, at high concentrations, to cross-activate PKA. To preclude the possibility that cGMP-gated ion channels and/or PKA may play a role in mucin secretion by NHBE cells, Rp-8-Br-cGMP, a unique cGMP analogue that can activate cGMP-gated ion channels similar to 8-Br-cGMP but inhibit PKG activity, was used as an agonist to distinguish the effects of PKG and cGMP-gated ion channels on mucin release.

As illustrated in these Results, particularly, in Results-I-1A (entry I-1A-11), Rp-8-Br-cGMP did not enhance mucin secretion when added to the cells with PMA.

Likewise, the specific PKA inhibitor, KT5720 (500 nM), did not affect mucin secretion induced by either PMA+8-Br-cGMP or UTP (Results-I-1D, entry I-1D-4).

These studies may negate the possibility that cGMP-gated ion channels or PKA are associated with mucin secretion, indicating that activation of PKG in NHBE cells is the mechanism whereby 8-Br-cGMP contributes to enhanced secretion. Furthermore, because UTP-induced mucin hypersecretion can be attenuated by the soluble guanylyl cyclase (GC-S) inhibitor LY83583, it is likely that activation of PKG occurs via the signaling pathway of nitric oxide (NO) Γ C-S Γ cGMP Γ PKG, as illustrated previously in differentiated guinea pig tracheal epithelial cells in vitro.

Given the participation of both PKC and PKG in the mucin secretory process, the present invention examines potential intracellular substrates of these enzymes that could play a role in signaling events downstream of the kinase activation. Numerous intracellular substrates can be phosphorylated by PKC or PKG, and phosphorylation by PKC of one such substrate, MARCKS protein, seemed to be of particular interest. MARCKS phosphorylation has been observed to correlate with a number of cellular processes involving PKC signaling and cytoskeletal contraction, such as cell movement, mitogenesis, and neural transmitter release. Because the dynamic process of secretion requires both kinase activation and translocation of intracellular granules to the cell periphery, MARCKS appeared to be a candidate for a mediator molecule connecting PKC/PKG activation and mucin granule exocytosis.

Example 2

MARCKS is a Key Molecule Linking PKC/PKG Activation to Mucin Secretion in NHBE Cells Results-I-2A as well as Results-I-2B-1 and Results-I-2B-2 demonstrate that the MARCKS protein is a key component of the mucin secretory pathway.

To address the signaling mechanism downstream of protein kinase activation, MARCKS protein, a specific cellular substrate of PKC that might play a role in linking kinase activation to granule release was studied. First, the presence of MARCKS in NHBE cells by [$^3$H]myristic acid-labeled immunoprecipitation assay was confirmed. MARCKS was expressed in NHBE cells, and it was found that the majority of this protein was membrane-associated under unstimulated conditions. In this regard, cells were labeled with [$^3$H]myristic acid overnight, and the membrane and the cytosol fractions were then isolated by differential centrifugation. MARCKS was found in each fraction at the same position (i.e. tritiated MARCKS migrated to reside between references of 66 kDa and 97 kDa at a position of approximately 90 kDa in each fraction) using an immunoprecipitation assay. A role for MARCKS as a key regulatory component of the mucin secretory pathway may be demonstrated in three different ways.

Figure 2:
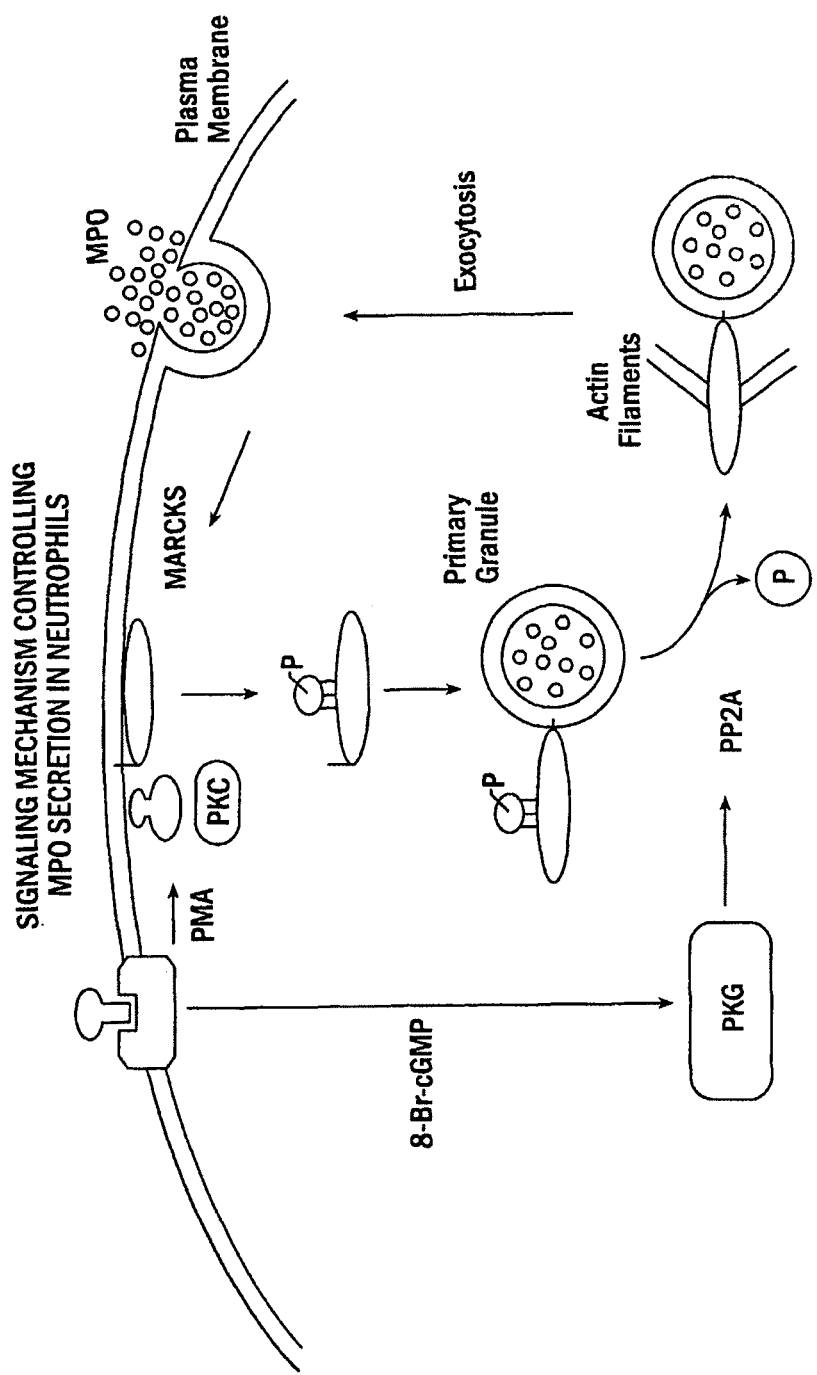
FIG. 2 depicts a signaling mechanism controlling secretion of an inflammatory mediator, myeloperoxidase (MPO), by a human neutrophil, which is an infiltrating inflammatory cell.

As stated above, direct involvement of MARCKS in mucin secretion by NHBE cells may be demonstrated by three separate lines of evidence. First, mucin secretion in response to stimulation by PMA+8-Br-cGMP or UTP was inhibited in a concentration-dependent manner by the MANS peptide, which had the amino acid sequence identical to the N-terminal region of MARCKS, whereas the corresponding control peptide (RNS), containing the same amino acid composition but arranged in a random order, did not affect secretion. The N-terminal myristoylated domain of MARCKS is known to mediate the MARCKS-membrane association. As indicated schematically in FIG. 2, MARCKS may function as a molecular linker by interacting with granule membranes at its N-terminal domain and binding to actin filaments at its PSD site, thereby tethering granules to the contractile cytoskeleton for movement and exocytosis. FIG. 2 shows a possible mechanism depicting that mucin secretagogue interacts with airway epithelial (goblet) cells and activates two separate protein kinases, PKC and PKG. Activated PKC phosphorylates MARCKS, causing MARCKS translocation from the plasma membrane to the cytoplasm, whereas PKG, activated via the nitric oxide (NO) Γ GC-δ cGMP Γ PKG pathway, in turn activates a cytoplasmic PP2A, which dephosphorylates MARCKS. This dephosphorylation stabilizes MARCKS attachment to the granule membranes. In addition, MARCKS also interacts with actin and myosin, thereby linking granules to the cellular contractile machinery for subsequent movement and exocytotic release. The attachment of MARCKS to the granules after it is released into the cytoplasm may also be guided by specific targeting proteins or some other forms of protein-protein interactions in which the N-terminal domain of MARCKS is involved. In either case, the MANS peptide, or an active fragment thereof, comprising at least 6 amino acids, would act to inhibit competitively targeting of MARCKS to the membranes of mucin granules, thereby blocking secretion.

A second test demonstrated the inhibitory effect of a MARCKS-specific antisense oligonucleotide on mucin secretion. It was shown by gel electrophoresis that an antisense oligonucleotide directed against MARCKS down-regulates MARCKS expression and attenuates mucin hypersecretion.

The antisense oligonucleotide down-regulated MARCKS mRNA and protein levels in NHBE cells and substantially attenuated mucin secretion induced by PKC/PKG activation. The inhibition was not as dramatic as that seen with the MANS peptide, which might be due to the high levels of endogenous MARCKS protein in NHBE cells and the relatively long half-life of MARCKS mRNA ($t_{1/2}$=4 to 6 h).

NHBE cells were treated with the antisense or the control oligonucleotide for 3 days and then stimulated with PMA (100 nM)+8-Br-cGMP (1 µM) for 15 min. Mucin secretion was analyzed by ELISA. Total RNA and protein were isolated from treated cells. MARCKS mRNA was assessed by Northern hybridization, and protein was assessed by Western blot. In the PMA (100 nM)+8-Br-cGMP (1 µM) a Northern blot (Results-I-3A-1) showed a decrease of about 15% in MARCKS mRNA compared with controls. In this regard, MARCKS mRNA as a percent of control is shown in the following results which are designated as Results-I-3A-2:

I-3A-2-1: medium was normalized as 100% (control);
I-3A-2-2: stimulation with PMA (100 nM)+8-Br-cGMP (1 µM) was observed as 95% of medium control;
I-3A-2-3: CTO (control oligonucleotide) with PMA (100 nM)+8-Br-cGMP (1 µM) was observed as 99% of medium control; and
I-3A-2-4: ASO (an antisense oligonucleotide) with PMA (100 nM)+8-Br-cGMP (1 µM) was observed as 71% of medium control.

A Western blot, Results-I-3B-1, associated with results designated as Results-I-3B-2 (below) showed a decrease of about 30% in MARCKS protein. In this regard, MARCKS protein as % of control was found as Results-I-3B-2 as follows;

I-3B-2-1: medium was normalized as 100% (control);
I-3B-2-2: stimulation with PMA (100 nM)+8-Br-cGMP (1 µM) was observed as 103% of medium control;
I-3B-2-3: CTO with PMA (100 nM)+8-Br-cGMP (1 µM) was observed as 105% of medium control; and
I-3B-2-4: ASO with PMA (100 nM)+8-Br-cGMP (1 µM) was observed as 42% of medium control.

Mucin hypersecretion was found to be attenuated significantly by the antisense oligonucleotide, whereas the control oligonucleotide had no effect.

In this regard, mucin secretion as a % of control was found in experimental results designated as Results-I-3C as follows:

I-3C-1: medium, was normalized as 100% (control);
I-3C-2: stimulation with PMA (100 nM)+8-Br-cGMP (1 µM) was observed as 216% of medium control (*);
I-3C-3: CTP with PMA (100 nM)+8-Br-cGMP (1 µM) was observed as 227% of medium control (*); and
I-3C-4: ASO with PMA (100 nM)+8-Br-cGMP (1 µM) was observed as 176% of medium control (†).

Data are presented as mean±S.E. (n=6 at each point) wherein the * is significantly different from medium control (p<0.05); and the t is significantly different from PMA+8-Br-cGMP stimulation (p<0.05).

The term CTO is the control oligonucleotide, while the term ASO is an antisense oligonucleotide.

It has been demonstrated that antisense oligonucleotides that are complementary to specific RNAs can inhibit the expression of cellular genes as proteins. See Erickson and Izant, Gene Regulation: Biology Of Antisense RNA And DNA, Vol. 1, Raven Press, N.Y., 1992. For example, selective inhibition of a p21 gene that differed from a normal gene by a single nucleotide has been reported. Chang et al., Biochemistry 1991, 30:8283-8286. Many hypotheses have been proposed to explain the mechanisms by which antisense oligonucleotides inhibit gene expression, however, the specific mechanism involved may depend on the cell type studied, the RNA targeted, the specific site on the RNA targeted, and the chemical nature of the oligonucleotide. Chiang et al., J. Biol. Chem. 1991, 266:18162-18171; Stein and Cohen, Cancer Res. 1988, 48:2659-2668.

A third experiment indicated that transfection of HBE1 cells with a PSD-deleted mutant MARCKS resulted in significant repression of mucin secretion induced by PKC/PKG activation. Deletion of the PSD would abolish the ability of MARCKS to bind to actin. As indicated in FIG. 2, by competing with native MARCKS for binding to granule membrane, the PSD-truncated MARCKS could thereby inhibit granule release as it is unable to interact with the actin filaments. Transfection of these cells with the wild-type MARCKS cDNA did not further enhance mucin secretion. Western blot assay showed that the expression level of endogenous MARCKS in HBE1 cells was quite high, comparable with that in NHBE cells, and transfection of wild-type MARCKS cDNA did not lead to notable increases in overall MARCKS protein level in these cells. This may explain why transfection with wild-type MARCKS did not further augment secretion and also why transfection with the PSD-deleted MARCKS only partially hindered mucin secretion.

Peptide Blocking Studies—NHBE cells were preincubated with either the MANS or the RNS peptide (1-100 µM) for 15 min, and then PMA (100 nM)+8-Br-cGMP (1 µM) or UTP (100 µM) was added, and cells were incubated for an additional 15 min or 2 h. respectively. Mucin secretion was measured by ELISA and experimental results are designated as Results-I-2B-1 and Results-I-2B-2, as follows.

Results-I-2B-1 indicate mucin secretion as % (percent) of control in the presence of PMA (100 nM)+8-Br-cGMP (1 µM) as follows:

I-2B-1-1: control mucin secretion was normalized as 100%;
I-2B-1-2: control in the presence of PMA (100 nM)+8-Br-cGMP (1 µM) provided mucin secretion was 210% of control (*);
I-2B-1-3: RNS peptide (1 µM) in the presence of PMA (100 nM)+8-Br-cGMP (1 µM) provided mucin secretion was 216% of control;
I-2B-1-4: RNS peptide (10 M) in the presence of PMA (100 nM)+8-Br-cGMP (1 µM) provided mucin secretion was 208% of control;
I-2B-1-5: RNS peptide (100 M) in the presence of PMA (100 nM)+8-Br-cGMP (1 µM) provided mucin secretion was 206% of control;
I-2B-1-6: MANS peptide (1 µM) in the presence of PMA (100 nM)+8-Br-cGMP (1 µM) provided mucin secretion was 188% of control;
I-2B-1-7: MANS peptide (10 µM) in the presence of PMA (100 nM)+8-Br-cGMP (1 µM) provided mucin secretion was 129% of control (†); and
I-2B-1-8: MANS peptide (100 µM) in the presence of PMA (100 nM)+8-Br-cGMP (1 µM) provided mucin secretion was 35% of control (†).

Results-I-2B-2, as follows, indicate mucin secretion as % of control in the presence of UTP (100 nM):

I-2B-2-1: control mucin secretion was normalized as 100%;
I-2B-2-2: control in the presence of UTP (100 µM) provided mucin secretion was 156% of control (*);

I-2B-2-3: RNS peptide (1 µM) in the presence of UTP (100 µM) provided mucin secretion was 154% of control;

I-2B-2-4: RNS peptide (10 µM) in the presence of UTP (100 µM) provided mucin secretion was 155% of control;

I-2B-2-5: RNS peptide (100 µM) in the presence of UTP (100 µM) provided mucin secretion was 158% of control;

I-2B-2-6: MANS peptide (1 µM) in the presence of UTP (100 µM) provided mucin secretion was 143% of control;

I-2B-2-7: MANS peptide (10 µM) in the presence of UTP (100 µM) provided mucin secretion was 125% of control (‡); and I-2B-2-8: MANS peptide (100 µM) in the presence of UTP (100 µM) provided mucin secretion was 46% of control (‡).

In Results-I-2B-2, incubation of NHBE cells with the MANS peptide resulted in a concentration-dependent suppression of mucin secretion in response to PKC/PKG activation or UTP stimulation, whereas the control peptide (RNS) may not have affected secretion at these same concentrations. In Results-I-2B-1 and Results-I-2B-2, the MANS peptide blocked mucin hypersecretion induced by PMA+8-Br-cGMP or UTP in a concentration-dependent manner. NHBE cells were preincubated with the indicated peptide for 15 min and then exposed to PMA (100 nM)+8-Br-cGMP (1 µM) for 15 min or UTP (100 µM) for 2 h. Mucin secretion was measured by ELISA. Data are presented as mean±S.E. (n=6 at each point), wherein * is significantly different from medium control $p<0.05$); t is significantly different from PMA+8-Br-cGMP stimulation ($p<0.05$); and f is significantly different from UTP stimulation (<0.05). Effects of the MANS peptide were likely not related to cytotoxicity or general repression of cellular metabolic activity, as neither the MANS nor the RNS peptide affected lactate dehydrogenase release or [$^3$H]deoxyglucose uptake by the cells.

Antisense Oligonucleotide Studies

To demonstrate further that MARCKS as a key signaling component of the mucin secretory pathway, the effect of an antisense oligonucleotide directed against MARCKS on mucin secretion was examined. As illustrated in Results-I-3A-2, Results-I-3B-2, and Results-I-3C, below, this antisense oligonucleotide down-regulated both mRNA and protein levels of MARCKS in NHBE cells and significantly attenuated mucin secretion induced by PMA+8-Br-cGMP, whereas a control oligonucleotide had no effect.

Results-I-3A-2 shows MARCKS mRNA as a percent of control as follows:

I-3A-1: medium, normalized as 100% (control);

I-3A-2: stimulation with PMA (100 nM)+8-Br-cGMP (1 µM) was observed as 95% of medium control;

I-3A-3: CTO (control oligonucleotide) with PMA (100 nM)+8-Br-cGMP (1 µM) was observed as 99% of medium control; and I-3A-4: ASO (an antisense oligonucleotide) with PMA (100 nM)+8-Br-cGMP (1 µM) was observed as 71% of medium control.

Results-I-3B-2 shows MARCKS protein as % of control as follows:

I-3B-2-1: medium was normalized as 100% (control);

I-3B-2-2: stimulation with PMA (100 nM)+8-Br-cGMP (1 µM) was observed as 103% of medium control;

I-3B-2-3: CTO with PMA (100 nM)+8-Br-cGMP (1 µM) was observed as 105% of medium control; and I-3B-2-4: ASO with PMA (100 nM)+8-Br-cGMP (1 µM) was observed as 42% of medium control.

A Western blot, (designated as Result-I-3B-1) associated with Results-I-3B-2 showed a decrease of about 30% in MARCKS protein.

Mucin hypersecretion was found to be attenuated significantly by the antisense oligonucleotide, whereas the control oligonucleotide had no effect.

Results-I-3C provide mucin secretion as a % of control as follows:

I-3C-1: medium, was normalized as 100% (control);

I-3C-2: stimulation with PMA (100 nM)+8-Br-cGMP (1 µM) was observed as 216% of medium control (*);

I-3C-3: CTP with PMA (100 nM)+8-Br-cGMP (1 µM) was observed as 227% of medium control (*); and I-3C-4: ASO with PMA (100 nM)+8-Br-cGMP (1 µM) was observed as 176% of medium control (†).

Data are presented as mean±S.E. (n=6 at each point) wherein the * is significantly different from medium control ($p<0.05$); and the † is significantly different from PMA+8-Br-cGMP stimulation ($p<0.05$).

The term CTO is the control oligonucleotide, while the term ASO is an antisense oligonucleotide.

Example 3

MARCKS Serves as a Convergent Signaling Molecule Mediating Cross-Talk of PKC and PKG Pathways Collectively, the above results demonstrated that MARCKS was involved integrally in the mucin secretory process. Next the present inventors addressed how MARCKS acts as a key regulatory molecule upon which PKC and PKG converge to regulate mucin secretion. PKG induces dephosphorylation of MARCKS by activating PP2A (see Results-I-5A, Results-I-5B, and Results-I-5C). MARCKS was phosphorylated by PKC and consequently translocated from the membrane to the cytoplasm. Here, PKG appeared to induce dephosphorylation of MARCKS. This dephosphorylation was reversed by the PKG inhibitor Rp-8-Br-PET-cGMP, indicating the dephosphorylation was specifically PKG-dependent.

NHBE cells were labeled with [$^{32}$P]orthophosphate and then exposed to the reagents: (a) Rp-8-Br-PET-cGMP (100 µM); (b) okadaic acid (500 nM); (c) 8-Br-cGMP (1 µM); and (d) PMA (100 nM). MARCKS phosphorylation in response to the treatments was evaluated by immunoprecipitation assay. It was found that 8-Br-cGMP reversed MARCKS phosphorylation induced by PMA, and this effect of 8-Br-cGMP could be blocked by Rp-8-Br-PET-cGMP (PKG inhibitor) or okadaic acid (PP1/2A inhibitor).

PMA-induced phosphorylation of MARCKS was reversed by subsequent exposure of cells to 8-Br-cGMP. Results of immunoprecipitation assay are designated Results-I-5A as follows:

I-5A-lane 1, medium alone as control gave no band at ~80 kDa;

I-5A-lane 2, 100 nM PMA gave a dark band at ~80 kDa;

I-5A-lane 3, 1 µM 8-Br-cGMP gave a faint band at ~80 kDa;

I-5A-lane 4, 100 nM PMA and 1 µM 8-Br-cGMP gave a faint band at ~80 kDa;

I-5B-lane 5, 100 nM PMA+1 µM 8-Br-cGMP+100 µM Rp-8-Br-PET-cGMP gave a dark band at ~80 kDa;

I-5A-lane 6, 100 nM PMA+1 µM 8-Br-cGMP+500 nM okadaic acid gave a dark band at ~80 kDa;

I-5A-lane 7, 100 nM PMA+okadaic acid at 500 nM gave a dark band at ~80 kDa;

I-5A-lane 8, 1 µM 8-Br-cGMP+500 nM okadaic acid gave a medium dark band at ~80 kDa; and I-5A-lane 8, 500 nM okadaic acid gave a faint band at ~80 kDa.

PMA-induced phosphorylation of MARCKS was reversed by subsequent exposure of cells to 8-Br-cGMP. Results of immunoprecipitation assay are designated Results-I-5B as follows:

I-5B-lane 1, medium alone for 8 min;
I-5B-lane 2, 100 nM PMA for 3 min;
I-5B-lane 3, 100 nM PMA for 3 min and then with 1 μM 8-Br-cGMP for 5 min:
I-5B-lane 4, 100 nM PMA for 8 min;
I-5B-lane 5, medium alone for 3 min and then 100 nM PMA+1 μM 8-Br-cGMP for 5 min.

8-Br-cGMP-induced MARCKS dephosphorylation was attenuated by fostriecin in a concentration-dependent manner. Results of immunoprecipitation assay are designated Results-I-5C (see below).

It is believed that PKG acts to dephosphorylate MARCKS via activation of a protein phosphatase. Okadaic acid at 500 nM, a concentration that could inhibit both PP1 and PP2A, blocked PKG-induced dephosphorylation of MARCKS, suggesting that PKG caused dephosphorylation by activating PP1 and/or PP2A. Further studies with fostriecin and direct assay of phosphatase activities indicated that only PP2A was activated by PKG and was responsible for removal of the phosphate groups from MARCKS. It is likely that either okadaic acid or fostriecin, at concentrations that inhibited PKG-induced dephosphorylation of MARCKS, attenuated mucin secretion induced by PMA+8-Br-cGMP or UTP.

PP2A is an essential component of the mucin secretory pathway. Mucin secretions as a percent of control were found in results designated as Results-I-6-1 directed to use of fostriecin in the presence of PMA (100 nM)+8-Br-cGMP (1 μM) and include the following:

I-6-1-1: control mucin secretion was normalized as 100%;
I-6-1-2: control in the presence of PMA (100 nM)+8-Br-cGMP (1 μM) provided mucin secretion as 211% of control (*);
I-6-1-3: fostriecin (1 nM) in the presence of PMA (100 nM)+8-Br-cGMP (1 μM) provided mucin secretion as 198% of control;
I-6-1-4: fostriecin (10 nM) in the presence of PMA (100 nM)+8-Br-cGMP (1 μM) provided mucin secretion as 182% of control;
I-6-1-5: fostriecin (100 nM) in the presence of PMA (100 nM)+8-Br-cGMP (1 μM) provided mucin secretion as 170% of control (†);
I-6-1-6: fostriecin (500 nM) in the presence of PMA (100 nM)+8-Br-cGMP (1 μM) provided mucin secretion as 134% of control (†); and
I-6-1-7: OA okadaic acid (500 nM) in the presence of PMA (100 nM)+8-Br-cGMP (1 μM) provided mucin secretion as 157% of control (t).

Mucin secretions as a percent of control were found in results designated as Results-I-6-2 directed to use of fostriecin in the presence of UTP (100 μM), and include the following:

I-6-2-1: control mucin secretion was normalized as 100%;
I-6-2-2: control in the presence of UTP (100 μM) normalized to provide mucin secretion as 161% (*);
I-6-2-3: fostriecin (10 nM) in the presence of UTP (100 μM) provided mucin secretion as 152% of control;
I-6-2-4: fostriecin (100 nM) in the presence of UTP (100 μM) provided mucin secretion as 134% of control (‡);
I-6-2-5: fostriecin (500 nM) in the presence of UTP (100 μM) provided mucin secretion as 124% of control (‡); and
I-6-2-6; OA in the presence of UTP (100 μM) provided mucin secretion as 112% of control (‡).

PP2A is an essential component of the mucin secretory pathway. NHBE cells were preincubated with the indicated concentration of fostriecin, okadaic acid (500 nM), or medium alone for 15 min and then stimulated with PMA (100 nM)+8-Br-cGMP (1 μM) for 15 min or with UTP (100 μM) for 2 h. Secreted mucin was measured by ELISA. Data are presented as mean±S.E. (n=6 at each point) wherein * stands for significantly different from medium control ($p<0.05$); † stands for significantly different from PMA+8-Br-cGMP stimulation ($p<0.05$); and ‡ stands for significantly different from UTP stimulation $p<0.05$). Thus, dephosphorylation of MARCKS by a PKG-activated PP2A appears to be an essential component of the signaling pathway leading to mucin granule exocytosis.

PKC-dependent phosphorylation releases MARCKS from the plasma membrane to the cytoplasm.

To reveal molecular events by which MARCKS links kinase activation to mucin secretion, phosphorylation of MARCKS in response to PKC/PKG activation was investigated in depth, and results are presented as Results-I-4A. PMA (100 nM) likely induced a significant increase (3-4-fold) in MARCKS phosphorylation in NHBE cells, and this phosphorylation was attenuated by the PKC inhibitor calphostin C (500 nM). Once phosphorylated, MARCKS was translocated from the plasma membrane to the cytoplasm. More specifically, the activation of PKC results in MARCKS phosphorylation in NHBE cells. Cells were labeled with [$^{32}$P]orthophosphate for 2 h and then exposed to the stimulatory and/or inhibitory reagents (see below). MARCKS phosphorylation in response to the treatments was evaluated by immunoprecipitation with the following specifics, designated Results-I-4A:

I-4A-lane 1, medium control, gave a dark band at ~90 kDa;
I-4A-lane 2, the vehicle, 0.1% Me$_2$SO (DMSO, dimethylsulfate) gave a dark band at ~90 kDa;
I-4A-lane 3, 100 nM 4.alpha.-PMA gave a dark band at ~90 kDa;
I-4A-lane 4, 100 nM PMA gave a very dark band at ~90 kDa;
I-4A-lane 5, 100 nM PMA+500 nM calphostin C gave a dark band at ~90 kDa; and
I-4A-lane 6, 500 nM calphostin C gave a dark band at ~90 kDa.

It was determined by immunoprecipitation assay that phosphorylated MARCKS is translocated from the plasma membrane to the cytoplasm. $^{32}$P-Labeled cells were exposed to PMA (100 nM) or medium alone for 5 min, and then the membrane and the cytosol fractions were isolated. Activation of PKG by 8-Br-cGMP (1 μM, another kinase activation event necessary for provoking mucin secretion), did not lead to MIARCKS phosphorylation, but, in fact, the opposite effect was observed: MARCKS phosphorylation induced by PMA was reversed by 8-Br-cGMP (see Results-I-5A).

Results 5A: immunoprecipitation asay demonstrating that phosphorylated MARCKS is translocated from the plasma membrane to the cytoplasm:

I-5A-Lane 1, medium control for 5 minute showed no band related to MARCKS phosphorylation;
I-5A-Lane 2, 100 nM PMA exposure showed a band related MARCKS phosphorylation (MARCKS phosphorylation was induced by PMA);
I-5A-Lane 3, 1 μM 8-Br-cGMP exposure showed no band related to MARCKS phosphorylation;

I-5A-Lane 4, 100 nM PMA+1 µM 8-Br-cGMP exposure showed no band related to MARCKS phosphorylation (MARCKS phosphorylation induced by PMA was reversed by 8-Br-cGMP);

I-5A-Lane 5, 100 nM PMA+1 µM 8-Br-cGMP+100 µM Rp-8-Br-PET-cGMP exposure showed a band related to MARCKS phosphorylation;

I-5A-Lane 6, 100 nM PMA+1 µM 8-Br-cGMP+500 nM Okadaic acid exposure showed a band related to MARCKS phosphorylation;

I-5A-Lane 7, 100 nM PMA+500 nM Okadaic acid exposure showed a band related to MARCKS phosphorylation;

I-5A-Lane 8, 1 µM 8-Br-cGMP+500 nM Okadaic acid exposure showed a faint band related to MARCKS phosphorylation; and I-5A-Lane 9, 500 nM Okadaic acid exposure showed a faint band related to MARCKS phosphorylation.

This effect of 8-Br-cGMP was not due to suppression of PKC activity, as the PMA-induced phosphorylation could be reversed by subsequent addition of 8-Br-cGMP to the cells. Therefore, PKG activation likely results in dephosphorylation of MARCKS.

Further investigation demonstrated that PKG-induced MARCKS dephosphorylation was blocked by 500 nM okadaic acid, a protein phosphatase (type 1 and/or 2A (PP1/2A)) inhibitor (see Results-I-5A, lane 6). Thus, it appeared that the dephosphorylation was mediated by PP1 and/or PP2A. To define the subtype of protein phosphatase involved, a novel and more specific inhibitor of PP2A, fostriecin ($IC_{50}$=3.2 nM), was utilized in additional phosphorylation studies.

Results-I-5C: Assay for inhibition of PKG-induced MARCKS dephosphorylation by fostriecin.

I-5C-Lane 1: exposure to medium control resulted in only a trace amount of a band related to MARCKS phosphorylation;

I-5C-Lane 2: exposure to PMA (100 nM) resulted in a strong band related to phosphorylated MARCKS;

I-5C-Lane 3: exposure to 8-Br-cGMP (1 µM) resulted in only a trace amount of a band related to MARCKS phosphorylation;

I-5C-Lane 4: exposure to PMA (100 nM)+8-Br-cGMP (1 µM) resulted in only a trace amount of a band related to MARCKS phosphorylation;

I-5C-Lanes 5 to 8: exposure to PMA (100 nM)+8-Br-cGMP (1 µM)+Fostriecin in amounts decreasing from 500 nM to 1 nM resulted in a strong band related to MARCKS phosphorylation at 500 nM concentration and bands of decreasing intensity as the amount of Fostriecin decreased;

I-5C-Lane 9: exposure to Fostriecin resulted in only a trace amount (apparently less intense than control) of a band related to MARCKS phosphorylation.

Fostriecin inhibited PKG-induced MARCKS dephosphorylation in a concentration-dependent manner (1-500 nM), suggesting that PKG induced the dephosphorylation via activation of PP2A. To confirm further activation of PP2A by PKG in NHBE cells, cytosolic PP1 and PP2A activities were determined after exposure of the cells to 8-Br-cGMP. PP2A activity was increased approximately 3-fold (from 0.1 to 0.3 nmol/mnin/mg proteins, $p<0.01$) at concentrations of 8-Br-cGMP as low as 0.1 µM, whereas PP1 activity remained unchanged. This data indicates that PP2A may be activated by PKG and is responsible for the dephosphorylation of MARCKS. Accordingly, this PP2A activity appeared critical for mucin secretion to occur; when PKG-induced MARCKS dephosphorylation was blocked by okadaic acid or fostriecin, the secretory response to PKC/PKG activation or UTP stimulation was ameliorated (see Results-I-6-1 and Results-I-6-2, above).

Example 4

MARCKS Associates with Actin and Myosin in the Cytoplasm

A radiolabeled immunoprecipitation assay revealed that MARCKS may associate with two other proteins of about 200 kDa (proximal to myosin heavy chain, non-muscle type A) and of about 40 kDa (proximal to actin) in the cytoplasm. Thus, NHBE cells were labeled with [$^3$H]leucine and [$^3$H]proline overnight, and the membrane and the cytosol fractions were prepared as described under "Experimental Procedures." Isolated fractions were precleared with the nonimmune control antibody (6F6). The cytosol was then divided equally into two fractions and used for immunoprecipitation carried out in the presence of 10 µM cytochalasin D (Biomol, Plymouth Meeting, Pa.) with the anti-MARCKS antibody 2F12 (with results designated as Results-I-7-lane 2) and the nonimmune control antibody 6F6 (with results designated as Results-I-7-lane 3), respectively. MARCKS protein in the membrane fraction was also assessed by immunoprecipitation using the antibody 2F12 (with results designated as Results-I-7-lane 1). The precipitated protein complex was resolved by 8% SDS-polyacrylamide gel electrophoresis and visualized by enhanced autoradiography. In radiolabeled immunoprecipitation assay designated as Results-I-7, MARCKS appeared to associate with two cytoplasmic proteins with molecular masses of about 200 and about 40 kDa, respectively. These two MARCKS-associated proteins were excised from the gel and analyzed by matrix-assisted laser desorption ionization/time of flight mass spectrometry/internal sequencing (the Protein/DNA Technology Center of Rockefeller University, N.Y.). The obtained peptide mass and sequence data were used to search protein databases via Internet programs ProFound and MS-Fit. Results indicate that they are myosin (heavy chain, non-muscle type A, ~200 kDa) and actin ~40 kDa, respectively. Matrix-assisted laser desorption ionization/time of flight mass spectrometry/internal sequence analysis indicated that these two MARCKS-associated proteins were myosin (heavy chain, non-muscle type A) and actin, respectively.

These studies suggest a new paradigm for the signaling mechanism controlling exocytotic secretion of airway mucin granules as well as providing what is believed to be the first direct evidence demonstrating a specific biological function of MARCKS in a physiological process. MARCKS serves as a key mediator molecule regulating mucin granule release in human airway epithelial cells. It is believed that elicitation of airway mucin secretion requires dual activation and synergistic actions of PKC and PKG. Activated PKC phosphorylates MARCKS, resulting in translocation of MARCKS from the inner face of the plasma membrane into the cytoplasm. Activation of PKG in turn activates PP2A, which dephosphorylates MARCKS in the cytoplasm. Because the membrane association ability of MARCKS is dependent on its phosphorylation state this dephosphorylation may allow MARCKS to regain its membrane-binding capability and may enable MARCKS to attach to membranes of cytoplasmic mucin granules. By also interacting with actin and myosin in the cytoplasm, MARCKS may then be able to tether granules to the cellular contractile apparatus, mediating granule movement to the cell periphery and subsequent exocytotic release. The wide distribution of MARCKS suggests the possibility that this or a similar mechanism may regulate secretion of membrane-bound granules in various cell types under normal or pathological conditions (see also FIGS. 1 and 2).

The invention also relates to a method for blocking any cellular secretory process, especially those releasing inflammatory mediators from inflammatory cells, whose stimulatory pathways involve the protein kinase C (PKC) substrate MARCKS protein and release of contents from membrane-bound vesicles. Specifically, the inventors have shown that stimulated release of the inflammatory mediator myloperoxidase from human (see Results-I-9, below) or canine (see Results-I-10, below) neutrophils can be blocked in a concentration-dependent manner by the MANS peptide.

Results-I-9 displays measures of Absorbance at 450 nm in human neutrophils, which were stimulated to secrete myloperoxidase (MPO) with 100 nM PMA and 10 μM 8-Br-cGMP in the presence of RNS peptide or MANS peptide to provide the following absorbances.

Results-I-9:

I-9-1: control, with 450 nm absorbance of 0.076;

I-9-2: control, in the presence of 100 nM PMA+10 μM 8-Br-cGMP had 450 nm absorbance of 0.100;

I-9-3: RNS peptide (1 μM), in the presence of 100 nM PMA+10 μM 8-Br-cGMP had 450 nm absorbance of 0.099;

I-9-4: RNS peptide (10 μM), in the presence of 100 nM PMA+10 μM 8-Br-cGMP had 450 nm absorbance of 0.100;

I-9-5: RNS peptide (100 μM), in the presence of 100 nM PMA+10 μM 8-Br-cGMP had 450 nm absorbance of 0.100;

I-9-6: MANS peptide (1 μM), in the presence of 100 nM PMA+10 μM 8-Br-cGMP had 450 nm absorbance of 0.102;

I-9-7: MANS peptide (10 μM), in the presence of 100 nM PMA+10 μM 8-Br-cGMP had 450 nm absorbance of 0.093, which is less than 0.102 seen in I-9-6, above; and I-9-8: MANS peptide (100 μM), in the presence of 100 nM PMA+10 μM 8-Br-cGMP had 450 nm absorbance of 0.068 (*) which is less than 0.102 seen in I-9-6, above and less than 0.093 seen in 7, above.

Results-I-10 displays measures of Absorbance at 450 nm in canine neutrophils that were stimulated to secrete myloperoxidase (MPO) with 100 nM PMA and μM 8-Br-cGMP in the presence of RNS peptide or MANS peptide, and provides the following absorbances.

Results-I-10:

I-10-1: control, with 450 nm absorbance of 0.10;

I-10-2: control, in the presence of 100 nM PMA+10 μM 8-Br-cGMP had 450 nm absorbance of 0.33;

I-10-3: RNS peptide (1 μM), in the presence of 100 nM PMA+10 μM 8-Br-cGMP had 450 nm absorbance of 0.32;

I-10-4: RNS peptide (10 μM), in the presence of 100 nM PMA+10 μM 8-Br-cGMP had 450 nm absorbance of 0.30;

I-10-5: MANS peptide (1 μM), in the presence of 100 nM PMA+10 μM 8-Br-cGMP had 450 nm absorbance of 0.25 (*), which is less than the absorbance seen in I-10-4, above; and I-10-6: MANS peptide (10 μM), in the presence of 100 nM PMA+10 μM 8-Br-cGMP had 450 nm absorbance of 0.09 (t), which is less than the absorbance seen in 1-10-5, above.

MANS peptide can block secretion of myloperoxidase from isolated canine neutrophils. Specifically, Results-I-9 shows isolated neutrophils that were stimulated to secrete myloperoxidase (MPO) with 100 nM PMA and 10 μM 8-Br-cGMP. 100 μM MANS peptide decreased secretion of MPO to control levels (*=p<0.05). 10 μM MANS causes a slight decrease in MPO secretion. 10 or 100 μM of a control peptide (RNS) has no effect on MPO secretion.

MANS peptide can block secretion of myloperoxidase from isolated human neutrophils. In Results-I-10, isolated neutrophils were stimulated to secrete myloperoxidase (MPO) with 100 nM PMA and 10 μM 8-Br-cGMP. 100 μM MANS peptide decreased secretion of MPO to control levels (*=p<0.05). 10 μM MANS causes a slight decrease in MPO secretion. 10 or 100 μM of a control peptide (RNS) has no effect on MPO secretion. Thus, in view of these results and the proposed mechanism of release of inflammatory mediators from vesicles or granules residing within inflammatory cells as represented for MPO and proposed to be common to all release of contents from granules (including release of mucin from mucin-containing granules), the MANS peptide and fragments thereof which exhibit analogous granule-release-inhibiting properties, which properties may be found using techniques described herein for MANS peptide, may be used therapeutically to block the release of granule-contained mediators of inflammation which are otherwise secreted from infiltrating inflammatory cells in any tissues. Many of these released mediators are responsible for the extensive tissue damage observed in a variety of chronic inflammatory diseases (i.e., respiratory diseases such as asthma, chronic bronchitis and COPD, inflammatory bowel diseases including ulcerative colitis and Crohn's disease, autoimmune diseases, skin diseases such as rosacea, eczema; and severe acne, arthritic and pain syndromes such as rheumatoid arthritis and fibromyalgia). Thus, administration of a peptide of this invention to a diseased tissue in a patient suffering from one or more of these diseases may be useful in treating symptoms of such diseases or preventing or reducing the severity of inflammation and subsequent tissue damage that would otherwise obtain in these inflammatory diseases in the absence of such treatment.

This invention may be useful for treating diseases such as arthritis, asthma, chronic bronchitis, COPD and cystic fibrosis.

This invention is accordingly useful for the treatment in both human and animal diseases, especially those affecting equines, canines, felines, and other household pets.

Results-I-11 and Results-I-12 show MPO secretion from LPS-primed human neutrophils as a model for humans, and Results-I-13, Results-I-14, and Results-I-15 show MPO secretion from LPS-primed canine neutrophils as a model for canines. In all of these experiments, isolated neutrophils were stimulated with LPS at a concentration of $1 \times 10^{-6}$ M for 10 minutes at 37° C. prior to adding the stimuli. The LPS primes the cells so they can respond to a secretagogue.

In this regard, it has been determined that phorbol 12-myristate 13-acetate (PMA) stimulates a small increase in MPO secretion from lipopolysaccharide (=LPS)-stimulated human neutrophils, which is enhanced in a concentration-dependent manner by co-stimulation with 8-Br-cGMP, a non-hydrolyzable cGMP analogue.

Thus, in one comparative experiment, when absorbance was monitored at 450 nm while observing MPO secretion from LPS-primed human neutrophils, Results-I-11 were obtained as follows.

Results-I-11:

I-11-1: in medium, a control absorbance reading of 0.15 was observed;

I-11-2: in the presence of 10 nM PMA, an absorbance reading of 0.19 was observed;

I-11-3; in the presence of 10 nM PMA+0.1 micromolar 8-Br-cGMP an absorbance of reading of 0.255 was observed;

I-11-4: in the presence of 10 nM PMA+1 micromolar 8-Br-cGMP an absorbance of reading of 0.265 was observed; and I-11-5: in the presence of 10 nM PMA plus 10 micromolar 8-Br-cGMP an absorbance of reading of 0.295 was observed.

Thus, PMA stimulates a small increase in MPO secretion from LPS-stimulated human neutrophils which is enhanced in a concentration-dependent manner by co-stimulation with 8-Br-cGMP.

In another comparative experiment, when absorbance was monitored at 450 nm while observing MPO secretion from LPS-primed human neutrophils, Results-I-12 were obtained as follows.

Results-I-12:

I-12-1: in medium, a control absorbance reading of 0.15 was observed;

I-12-2: in the presence of cGMP, an absorbance reading of 0.155 was observed;

I-12-3: in the presence of 10 micromolar 8-Br-cGMP and 1 nM PMA, an absorbance of reading of 0.27 was observed; and I-12-4: in the presence of 10 micromolar 8-Br-cGMP and 10 nM PMA, an absorbance of reading of 0.32 was observed.

Thus, 8-Br-cGMP simulation has little effect on MPO secretion from LPS-stimulated human neutrophils until a co-stimulation with PMA occurs in a concentration-dependent manner.

In another comparative experiment, when absorbance was monitored at 450 nm while observing MPO secretion from LPS-primed canine neutrophils, Results-I-13 were obtained as follows.

Results-I-13:

I-13-1: in medium, a control absorbance reading of 0.064 was observed;

I-13-2: in the presence of 100 nM PMA, an absorbance reading of 0.078 was observed;

I-13-3: in the presence of 100 nM PMA plus 0.1 micromolar 8-Br-cGMP an absorbance of reading of 0.079 was observed;

I-13-4: in the presence of 100 nM PMA plus 1 micromolar 8-Br-cGMP an absorbance of reading of 0.096 was observed; and I-13-5: in the presence of 100 nM PMA plus 10 micromolar 8-Br-cGMP an absorbance of reading of 0.123 was observed.

Thus, PMA stimulates a small increase in MPO secretion from LPS-stimulated canine neutrophils which is enhanced in a concentration-dependent manner by co-stimulation with 8-Br-cGMP.

In another comparative experiment, when absorbance was monitored at 450 nm while observing MPO secretion from LPS-primed canine neutrophils, Results-I-14 were obtained as follows.

Results-I-14:

I-14-1: in medium, a control absorbance reading of approximately 0.078 was observed;

I-14-2: in the presence of 8-Br-cGMP (1 micromolar), an absorbance reading of approximately 0.078 was observed;

I-14-3: in the presence of 1 micromolar 8-Br-cGMP and 1 nM PMA, an absorbance reading of approximately 0.078 was observed;

I-14-4: in the presence of 1 micromolar 8-Br-cGMP and 10 nM PMA, an absorbance reading of approximately 0.0795 was observed;

I-14-5: in the presence of 1 micromolar 8-Br-cGMP and 100 nM PMA, an absorbance reading of approximately 0.098 was observed; and I-14-6: in the presence of 1 micromolar 8-Br-cGMP and 1000 nM PMA, an absorbance reading of approximately 0.113 was observed.

Thus, 8-Br-cGMP simulation has little effect on MPO secretion from LPS-stimulated canine neutrophils until a co-stimulation with PMA occurs in a concentration-dependent manner.

In another comparative experiment, when absorbance was monitored at 450 nm while observing MPO secretion from LPS-primed canine neutrophils, Results-I-15 were obtained as follows.

Results-I-15:

I-15-1: in medium, a control absorbance reading of approximately 0.0825 was observed;

I-15-2: in the presence of 100 nM PMA, an absorbance reading of 0.0825 was observed;

I-15-3: in the presence of 10 micromolar 8-Br-cGMP, an absorbance reading of approximately 0.0835 was observed; and I-15-4: in the presence of both PMA and 8-Br-cGMP, an absorbance reading of approximately 0.129 was observed.

Thus, co-stimulation with PMA+8-Br-cGMP is required for maximal MPO secretion from LPS-stimulated canine neutrophils.

Methods and Materials Relevant at Least to Examples 1 to 4

NHBE Cell Culture—Expansion, cryopreservation, and culture of NHBE cells in the air/liquid interface were performed as described previously. See, Krunkosky et al. Briefly, NHBE cells (Clonetics, San Diego, Calif.) were seeded in vented T75 tissue culture flasks (500 cells/cm.sup.2) and cultured until cells reached 75-80% confluence. Cells were then dissociated by trypsin/EDTA and frozen as passage-2. Air/liquid interface culture was initiated by seeding passage-2 cells ($2 \times 10^4$ cells/cm$^2$) in TRANSWELL® clear culture inserts (Costar, Cambridge, Mass.) that were thinly coated with rat tail collagen, type 1 (Collaborative Biomedical, Bedford, Mass.). Cells were cultured submerged in medium in a humidified 95% air, 5% $CO_2$ environment for 5-7 days until nearly confluent. At that time, the air/liquid interface was created by removing the apical medium and feeding cells basalaterally. Medium was renewed daily thereafter. Cells were cultured for an additional 14 days to allow for full differentiation.

Measurement of Mucin Secretion by ELISA—Before collection of "base line" and "test" mucin samples, the accumulated mucus at the apical surface of the cells was removed by washing with phosphate-buffered saline, pH 7.2. To collect the base-line secretion, cells were incubated with medium alone, and secreted mucin in the apical medium was collected and reserved. Cells were rested for 24 h and then exposed to medium containing the selected stimulatory and/or inhibitory reagents (or appropriate controls), after which secreted mucin was collected and reserved as the test sample. Incubation times for the base line and the test were the same but varied depending on the test reagent utilized. Both base line and test secretions were analyzed by ELISA using an antibody capture method as known in the art. See, e.g., Harlow et al., Antibodies: A Laboratory Manual, pp. 570-573, Cold Spring Harbor Laboratory, Cold Spring Harbor, N.Y. (1988). The primary antibody for this assay was 17Q2 (Babco, Richmond, Calif.), a monoclonal antibody that reacts specifically with a carbohydrate epitope on human airway mucins. The ratio of test/base-line mucin, which is similar to a "secretory index", was used to quantify mucin secretion, allowing each culture dish to serve as its own control and thus, minimizing deviation caused by variability among culture wells. Wright et al., Am. J. Physiol. 271, L854-L861 (1996). Levels of mucin secretion were reported as percentage of the medium control.

Radiolabeled Immunoprecipitation Assay—when Labeling with [$^{32}$P]phosphate, cells were preincubated for 2 h in phosphate-free Dulbecco's modified Eagle's medium containing 0.2% bovine serum albumin and then labeled with 0.1 mCi/ml [$^{32}$P]orthophosphate (9000 Ci/mmol, PerkinElmer Life Sciences) for 2 h. For labeling with [$^3$H]myristic acid or $^3$H-amino acids, cells were incubated overnight in medium containing 50 µCi/ml [$^3$H]myristic acid (49 Ci/mmol, PerkinElmer Life Sciences) or 0.2 mCi/ml [$^3$H]leucine (159 Ci/mmol, PerkinElmer Life Sciences) plus 0.4 mCi/ml [$^3$H]proline (100 Ci/mmol, PerkinElmer Life Sciences). Following labeling, cells were exposed to stimulatory reagents for 5 min. When an inhibitor was used, cells were preincubated with the inhibitor for 15 min prior to stimulation. At the end of the treatments, cells were lysed in a buffer containing 50 mM Tris-HCl (pH 7.5), 150 mM NaCl, 1 mM EDTA, 10% glycerol, 1% Nonidet P-40, 1 mM phenylmethylsulfonyl fluoride, 1 mM benzamidine, 10 µg/ml pepstatin A, and 10 µg/ml leupeptin. Trichloroacetic acid precipitation and scintillation counting may determine the radiolabeling efficiency in each culture. Immunoprecipitation of MARCKS protein was carried out according to the method of Spizz and Blackshear using cell lysates containing equal counts/min. Spizz et al., J. Biol. Chem. 271, 553-562 (1996). Precipitated proteins were resolved by 8% SDS-polyacrylamide gel electrophoresis and visualized by autoradiography. Anti-human MARCKS antibody (2F12) and nonimmune control antibody (6F6) were used in this assay.

To assess MARCKS or MARCKS-associated protein complexes in different subcellular fractions, radiolabeled and treated cells were scraped into a homogenization buffer (50 mM Tris-HCl (pH 7.5), 10 mM NaCl, 1 mM EDTA, 1 mM phenylmethylsulfonyl fluoride, 1 mM benzamidine, 10 µg/ml pepstatin A, 10 µg/ml leupeptin) and then disrupted by nitrogen cavitation (800 pounds/square inch for 20 min at 4° C.). Cell lysates were centrifuged at 600×g for 10 min at 4° C. to remove nuclei and unbroken cells. Post-nuclear supernatants were separated into membrane and cytosol fractions by ultracentrifugation at 400,000×g for 30 min at 4° C. The membrane pellet was solubilized in the lysis buffer by sonication. Immunoprecipitation was then carried out as described above.

MARCKS-related Peptides—Both the myristoylated N-terminal sequence (MANS) and the random N-terminal sequence (RNS) peptides were synthesized at Genemed Synthesis, Inc. (San Francisco, Calif.), then purified by high pressure liquid chromatography (>95% pure), and confirmed by mass spectroscopy with each showing one single peak with an appropriate molecular mass. The MANS peptide consisted of sequence identical to the first 24 amino acids of MARCKS, i.e. the myristoylated N-terminal region that mediates MARCKS insertion into membranes, MA-GAQF-SKTAAKGEAAAERPGEAAVA (SEQ ID NO: 1) (where MA=N-terminal myristate chain). The corresponding control peptide (RNS) contained the same amino acid composition as the MANS but arranged in random order, MA-GTAPAAE-GAGAEVKRASAEAKQAF (SEQ ID NO: 26). The presence of the hydrophobic myristate moiety in these synthetic peptides enhances their permeability to the plasma membranes, enabling the peptides to be taken up readily by cells. To determine the effects of these peptides on mucin secretion, cells were preincubated with the peptides for 15 min prior to addition of secretagogues, and mucin secretion was then measured by ELISA.

Antisense Oligonucleotides—MARCKS antisense oligonucleotide and its corresponding control oligonucleotide were synthesized at Biognostik GmbH (Gottingen, Germany). NHBE cells were treated with 5 µM antisense or control oligonucleotide apically for 3 days (in the presence of 2 µg/ml lipofectin for the first 24 h). Cells were then incubated with secretagogues, and mucin secretion was measured by ELISA. Total RNA and protein were isolated from treated cells. MARCKS mRNA was assessed by Northern hybridization according to conventional procedures using human MARCKS cDNA as a probe. MARCKS protein level was determined by Western blot using purified anti-MARCKS IgG1 (clone 2F12) as the primary detection antibody.

Transient Transfection—The phosphorylation site domain (PSD) of MARCKS contains the PKC-dependent phosphorylation sites and the actin filament-binding site. To construct a PSD-deleted MARCKS cDNA, two fragments flanking the PSD sequence (coding for 25 amino acids) were generated by polymerase chain reaction and then ligated through the XhoI site that was attached to the 5'-ends of oligonucleotide primers designed for the polymerase chain reaction. The resultant mutant cDNA and the wild-type MARCKS cDNA were each inserted into a mammalian expression vector pcDNA4/TO (Invitrogen. Carlsbad, Calif.). Isolated recombinant constructs were confirmed by restriction digests and DNA sequencing.

HBE1 is a papilloma virus-transformed human bronchial epithelial cell line capable of mucin secretion when cultured in air/liquid interface. Transfection of HBE1 cells was carried out using the Effectene transfection reagent (Qiagen, Valencia, Calif.) according to the manufacturer's instructions. Briefly, differentiated HBE1 cells grown in air/liquid interface were dissociated by trypsin/EDTA and re-seeded in 12-well culture plates at $1\times10^5$ cells/cm$^2$. After overnight incubation, cells were transfected with the wild-type MARCKS cDNA, the PSD-truncated MARCKS cDNA, or vector DNA. Cells were cultured for 48 h to allow gene expression and then exposed to secretagogues and mucin secretion measured by ELISA. All transfections were carried out in the presence of pcDNA4/TO/lacZ plasmid (Invitrogen) (DNA ratio 6:1, total 1 µg DNA, ratio of DNA to Effectene reagent=1:25) to monitor variations in transfection efficiency. Results showed no significant difference in beta-galactosidase activities in cell lysates isolated from the transfected cells, indicating similar transfection efficiency among different DNA constructs (data not shown).

Protein Phosphatase Activity Assay—PP1 and PP2A activities were measured using a protein phosphatase assay system (Life Technologies, Inc.) as known in the art with slight modification. Huang et al., Adv. Exp. Med. Biol. 396, 209-215 (1996). Briefly, NHBE cells were treated with 8-Br-cGMP or medium alone for 5 min. Cells were then scraped into a lysis buffer (50 mM Tris-HCl (pH 7.4), 0.1% beta-mecaptoethanol, 0.1 mM EDTA, 1 mM benaamidine, 10 µg/ml pepstatin A, 10 µg/ml leupeptin) and disrupted by sonication for 20 s at 4° C. Cell lysates were centrifuged and the supernatants saved for phosphatase activity assay. The assay was performed using $^{32}$P-labeled phosphorylase A as a substrate. Released $^{32}$P$_i$ was counted by scintillation. The protein concentration of each sample was determined by the Bradford assay. PP2A activity was expressed as the sample total phosphatase activity minus the activity remaining in the presence of 1 nM okadaic acid. PP1 activity was expressed as the difference between the activities remaining in the presence of 1 nM and 1 µM okadaic acid, respectively. Protein phosphatase activities were reported as nmol of P$_i$ released per min/mg total protein.

Cytotoxicity Assay—All reagents used in treating NHBE cells were examined for cytotoxicity by measuring the total release of lactate dehydrogenase from the cells. The assay was carried out using the Promega Cytotox 96 Kit according to the manufacturer's instructions. All experiments were performed with reagents at non-cytotoxic concentrations.

Statistical Analysis—Data were analyzed for significance using one-way analysis of variance with Bonferroni post-test corrections. Differences between treatments were considered significant at p<0.05.

Isolation of PMNs from canine blood—The steps involved in isolating PMN include collecting 10 ml ACD anticoagulated blood; then layering 5 ml on 3.5 ml PMN isolation media while ensuring that the PMN isolation media (IM) was at room temperature (RI). Next, the blood was centrifuged at room temperature for 30', 550×g at 1700 RPMs. The low lower white band was transferred into a 15 ml conical centrifuge tube (CCFT). Next, 2V HESS with 10% fetal bovine serum (PBS) was added and centrifuged at room temperature for 10', 400×g at 1400 RPMs. The pellet was then resuspended in 5 ml 1-1ESS with PBS. The cell suspension was added to 50 ml CCFT containing 20 ml of ice cold 0.88% $NH_4$Cl and inverted two to three times. The resulting product was centrifuged for 10', 800×g at 2000 RPMs, then aspirated and resuspended in ml HBSS with FBS. The prep was examined by counting and cytospin and preferably for whole blood, the cell number should be between $10^9$-$10^{11}$ cells and for PMNs, cell number should be between 2-4×$10^7$ cells. See generally, Wang et al., J. Immunol., "Neutrophil-induced changes in the biomechanical properties of endothelial cells: roles of ICAM-1 and reactive oxygen species," 6487-94 (2000).

MPO Colorimetric Enzyme Assay—Samples were assayed for MPO activity in 96 well round bottom microtiter plates using a sandwich ELISA kit (R & D Systems, Minneapolis, Minn.). Briefly, 20 microliters of sample is mixed with 180 microliters of substrate mixture containing 33 mM potassium phosphate, pH 6.0, 0.56% Triton X-100, 0.11 mM hydrogen peroxide, and 0.36 mM O-Diannisidine Dihydrochloride in an individual microtiter well. The final concentrations in the assay mixture are: 30 mM potassium phosphate, pH 6.0, 0.05% Triton X-100, 0.1 mM hydrogen peroxide, and 0.32 mM O-Diannisidine Dihydrochloride. After mixing, the assay mixture was incubated at room temperature for 5 minutes, and MPO enzyme activity determined spectrophotometrically at 550 nanometers. Samples were assayed in duplicate.

Example 5

In Vitro Assessment of Mucus Secretion

Cell Culture System: Expansion and Cryopreservation

Primary normal human bronchial epithelial (NHBE) cells (Clonetics, San Diego, Calif.) were seeded into vented T75 tissue culture flasks (500 cells/$cm^2$) in bronchial epithelial basal medium (BEBM; Clonetics, San Diego, Calif.) containing 25 ng/ml human recombinant epidermal growth factor (EGF; Intergen, Purchase, N.Y.), 65 ng/ml bovine pituitary extract (prepared by the methods of Bertolero et al. *Exp Cell Res* 155:64, 1984), 5×$10^{-8}$ M all-trans retinoic acid, 1.5 µg/ml bovine serum albumin (Intergen, Purchase, N.Y.), 20 IU/ml nystatin (Gibco, Grand Island, N.Y.), 0.5 µg/ml hydrocortisone, 5 µg/ml insulin, g/ml transferrin, 0.5 µg/ml epinephrine, 6.5 ng/ml triiodothyronine, 50 µg/ml gentamicin, and 50 µg/ml amphotericin-B (Clonetics; San Diego, Calif.). Once confluent, cultures were dissociated with trypsin/EDTA and frozen as passage-2 according to the methods of Clonetics Corporation.

Air-Liquid Interface Culture of NHBE Cells

Following the expansion, NHBE cells were cultured in air/liquid interface according to the methods of Gray and co-workers with minor modifications (Gray et al. *Am J Respir Cell Mol Biol* 14:104, 1996). The air-liquid interface culture was initiated by seeding NHBE cells (passage-2, 2×$10^4$ cells/$cm^2$) on Transwell-clear culture inserts (24.5 mm, 0.45 µm pore size; Costar, Cambridge, Mass.) that were thin coated with rat tail collagen, type I (Collaborative Research, Bedford, Mass.). Cells were cultured submerged to 70% confluency (5-7 days) in a 1:1 mixture of bronchial epithelial cell growth medium (Clonetics, San Diego, Calif.):Dulbecco's modified Eagles medium with high glucose (BEGM:DMEM-H), containing the same supplements as described above with the exception of EGF (0.5 ng/ml). When cultures were 70% confluent, the air-liquid interface was created by removing the apical medium, and the basal medium (BEGM:DMEM-H) was changed daily thereafter. Cells were then cultured for an additional 14 days in air-liquid interface, a total of 21 days in culture.

Mucus ELISA

Mucus secreted from the airway epithelial cells in vitro after stimulation by activators was assessed using an ELISA (antibody capture method) (E. Harlow, D. Lane. "Antibodies: A Laboratory Manual." New York: Cold Spring Harbor Laboratory Press, 1988), wherein the collected mucus is bound directly to the ELISA plate. Mucus was detected using an antibody raised against monkey airway mucus (Lin et al. *Am J Respir Cell Mol Biol* 1:41, 1989).

Example 6

MARCKS mRNA in Human Bronchial Epithelial Cells

MARCKS messenger RNA was detected in human bronchial epithelial cells grown in air/liquid interface culture by Northern analysis (Ausubel et al., eds. "Current Protocols in Molecular Biology." New York: John Wiley & Sons, 1992) using a human MARCKS cDNA (approximate length 1 kb) as a radiolabelled probe. MARCKS message increases as these cells become more differentiated when maintained in an air/liquid interface culture.

To detect MARCKS protein in these cells, cells were labeled with $^3$H-myristic acid (as MARCKS is myristoylated) for 16 hours in media. Cells were lysed, and MARCKS protein was immunoprecipitated according to the method of Spizz & Blackshear (*J Biol Chem* 271:553, 1996) using monoclonal antibody 2F12 (a gift from the Blackshear laboratory).

MARCKS within the airway epithelial cells was found to be phosphorylated by the PKC activator, PMA (100 nM), while 4α-PMA (a phorbol ester control which does not activate PKC), did not phosphorylate MARCKS. Phosphorylation of MARCKS by PMA was attenuated by Calphostin C (500 nM). NHBE cells also contained substantial amounts of cGMP-dependent protein kinase type 1α (PKG-1α) activity, which was localized to the cytosolic fraction. The cells exhibited constitutive PKG activity which was increased by incubation with 100 µM dibutryl cGMP. In addition, the phosphorylation of MARCKS induced by PMA was reversed by incubation with 8-Br-cGMP (10 µM). Okadaic acid (500 nM) inhibited this effect. These results indicate that 8-Br-cGMP activates a phosphatase (type 1 or 2A), which dephosphorylates MARCKS.

Example 7

Blocking of Mucin Secretion by Peptide MANS

The effect on mucus secretion of a myristoylated peptide containing the first 24 amino acids of the human MARCKS protein (MANS; myristoylated N-terminal sequence; SEQ ID NO: ) was tested. Cultured normal human bronchial epithelial cells as described above were used. Test cells were co-incubated for 15 minutes in apical and basolateral media containing 1, 10 or 100 µM of MANS peptide, and then co-incubated for minutes with the peptide and 100 nM PMA plus 1 µM 8-Br-cGMP. Experimental results, designated as Results M-1A below, present data found for stimulated mucin secretion from human bronchial epithelial cells in vitro in response to varying amounts of the MANS peptide (SEQ ID NO: 1):

M-1A-1: media/control (no peptide, no stimulation) provided a normalized mucin secretion level as 100% of control;

M-1A-2: 100 nM PMA+1 µM 8-Br-cGMP (stimulated secretion) provided a mucin secretion level measured as 191% of control (*);

M-1A-3: 1 µM MANS peptide, in the presence of 100 nM PMA and 1 µM 8-Br-cGMP, provided a mucin secretion level measured as 171% of control;

M-1A-4: 10 µM MANS peptide, in the presence of 100 nM PMA and 1 µM 8-Br-cGMP, provided a mucin secretion level measured as 117% of control (); and M-1A-5: 100 µM MANS peptide, in the presence of 100 nM PMA and 1 µM 8-Br-cGMP provided a mucin secretion level measured as 29% of control ().

Single asterisks (*) indicate that the measured response was statistically different than the media control (M-1A-1), and double asterisks (**) indicate that the response was statistically different than that of stimulated cells that were not exposed to the MANS peptide (M-1A-2).

In this regard, control cells were not exposed to MANS peptide but were preincubated in media only (M-1A-1) or media containing PMA and 8-Br-cGMP (M-1A-2).

Stimulation by PMA and 8-Br-cGMP caused an increase in mucus secretion over control levels (to 191% in M-1A-2 over M-1A-1). This increase, however, was blocked by pre- and co-incubation with the MANS peptide. Levels of secreted mucus fell to control values (117% of control found in M-1A-4) when 10 µM peptide was used, and levels of secreted mucus were well below control values following incubation with 100 µM MANS peptide (29% of control levels found in M-1A-5).

The MANS peptide (100 µM) was also found to decrease constitutive (basal) mucus secretion by one hour incubation. Cells were treated as described above except that no PMA or 8-Br-cGMP was used. In addition, a negative control peptide of the same amino acid composition as the MANS peptide in random order (RNS; random N-terminal sequence) did not affect constitutive mucus secretion. Results, designated as Results-M-1B, are presented as follows and show the inhibition of basal mucin secretion by human bronchial epithelial cells exposed to the MANS peptide (SEQ ID NO: 1) or a negative control peptide consisting of the same amino acids as the MANS peptide, but in random order (RNS peptide; random N-terminal sequence (SEQ ID NO: 26):

M-1B-1: media control normalized to a level of mucin secretion as 100%;

M-1B-2: one hour incubation with 100 µM of RNS negative control peptide provided mucin secretion levels relative to control of 90%; and M-1B-3: one hour incubation with 100 µM of MANS peptide provided mucin secretion levels relative to control of 28% (*).

Single asterisk (*) in M-1B-3 indicates that the response was statistically different than the media control (M–1B-1).

Example 8

UTP-Induced Mucin Secretion is Blocked by Peptide MANS

These experiments were carried out similarly to those described in Example 7. To test for stimulated secretion, the cells were exposed apically and basolaterally to uridine 5'-triphosphate (UTP) at a concentration of 0.1 mM in media. Cells were pre-incubated for 15 minutes with the MANS peptide and test cultures were then co-incubated with the MANS peptide and UTP for 45 minutes.

The effects of varying (increasing) amounts of the MANS peptide (SEQ ID NO: ) on UTP-induced mucin secretion by human bronchial epithelial cells in vitro were evaluated with results presented with designation Results-M-2 (below) in which mucin secretion is normalized to media control as 100% and data expressed as % of control:

M-2-1: mucin secretion in the media/control is 100%;

M-2-2: mucin secretion in media containing 0.1 mM UTP (*) was found to be 159% of control levels;

M-2-3: mucin secretion in media containing 0.1 mM UTP and 1 µM MANS peptide was found to be 146% of control levels;

M-2-4: mucin secretion in media containing 0.1 mM UTP and 10 µM MANS peptide was found to be 128% of control levels (); and M-2-5: mucin secretion in media containing 0.1 mM UTP and 100 µM MANS peptide was found to be 46% of control levels ().

Single asterisks (*) indicate that the measured response was statistically different from the media control (M–2-1), and double asterisks (**) indicate that the response was statistically different from that of UTP-stimulated cells that were not exposed to the MANS peptide (M–2-2).

The MANS peptide at a range of 10 µM to 100 µM significantly reduced UTP-stimulated mucus secretion by human bronchial epithelial cells. For example, relative to mucin secretion levels stimulated by the presence of 0.1 mM UTP in the absence of MANS peptide (i.e., relative to M-2-2):

M-2-3 shows the presence of MANS peptide at 1 µM reduced mucin secretion to about 90% of the level observed absent MANS peptide;

M-2-4 shows the presence of MANS peptide at 10 µM reduced mucin secretion to about 80% of the level observed absent MANS peptide; and M-2-5 shows the presence of MANS peptide at 100 µM reduced mucin secretion to about 29% of the level observed absent MANS peptide.

Example 9

Effect of MA-PSD Peptide on Mucin Secretion

These experiments were carried out using normal human bronchial epithelial cells in vitro as described above. A myristoylated peptide composed of the 25 amino acid phosphorylation site domain of MARCKS (MA-PSD peptide; SEQ ID NO: ) was prepared. Test cells were preincubated for 15 minutes in apical and basolateral media containing the MA-PSD peptide (1, 10 or 100 µM), and then co-incubated for 15 minutes with the peptide and stimulus (100 nM PMA plus 1 µM 8-Br-cGMP). Control cells were preincubated in media only (designated M-3A-1, below); or with 100 nM PMA only (designated M-3A-2, below); or with 100 nM PMA and 1 µM 8-Br-cGMP (designated M-3A-3, below). Data are presented as Results-M-3A (i.e., the effects of the MANS peptide (SEQ ID NO: 1) and the MA-PSD peptide (SEQ ID NO: 25) on stimulated mucin secretion by human bronchial epithelial cells in vitro) as mucin secretion levels observed as a percentage of the level observed in media used as control:

M-3A-1: media/control normalized to 100% as a reference level of mucin secretion:

M-3A-2: 100 nM PMA provided a mucin secretion level relative to media control of 122% (*);

M-3A-3: 100 nM PMA+1 µM 8-Br-cGMP provided a mucin secretion level relative to media control of 191% (*);

M-3A-4: 1 µM MA-PSD peptide in the presence of 100 nM PMA+1 µM 8-Br-cGMP provided a mucin secretion level relative to media control of 226% (**);

M-3A-5: 10 µM MA-PSD peptide in the presence of 100 nM PMA+1 µM 8-Br-cGMP provided a mucin secretion level relative to media control of 316% (**);

M-3A-6: 100 µM MA-PSD peptide in the presence of 100 nM PMA+1 µM 8-Br-cGMP provided a mucin secretion level relative to media control of 191%;

M-3A-7: 1 µM MANS peptide in the presence of 100 nM PMA+1 µM 8-Br-cGMP provided a mucin secretion level relative to media control of 171%;

M-3A-8: 10 µM MANS peptide in the presence of 100 nM PMA+1 µM 8-Br-cGMP provided a mucin secretion level relative to media control of 117% (); and M-3A-9: 100 µM MANS peptide in the presence of 100 nM PMA+1 µM 8-Br-cGMP provided a mucin secretion level relative to media control of 30% ().

When referenced to the level seen in M-3A-3 as 100% (i.e., in the presence of 100 nM PMA+1 µM 8-Br-cGMP absent any MANS peptide) as a baseline for mucin secretion in the absence of MANS peptide, then relative mucin secretion levels observed in M-3A-3, M-3A-7, M-3A-8, and M-3A-9 above become 100%, 90%, 61%, and 16%, respectively. Thus, increasing MANS peptide concentrations from zero up to 100 nM in these experiments reduced mucin secretion levels from control levels (i.e., 100%) to about 16% of control levels.

Single asterisks (*) indicate that the response was statistically different than the media control (see M-3A-1 in this example), and double asterisks (**) indicate that the response was statistically different than that in stimulated cells that were not exposed to the MANS peptide (see M-3A-3).

Stimulation by PMA and 8-Br-cGMP caused about a 100% increase in mucus secretion over control levels. This increase was augmented in a dose-dependent manner by pre- and co-incubation with the MA-PSD peptide, 1 or 10 µM. Interestingly, stimulated levels of mucus secretion were unaffected by the presence of 100 µM peptide.

The effect of MA-PSD peptide (1, 10 and 100 µM) on basal mucin secretion was also measured. Cells as described above were incubated for one hour with the MA-PSD peptide (no PMA or 8-Br-cGMP).

The effect of one hour of incubation with the MA-PSD peptide (SEQ ID NO: ) (1, 10 and 100 µM) on basal mucin secretion by human bronchial epithelial cells in vitro provide results designated as Results-M-3B as follows:

M-3B-1: media/control, here normalized to 100% as a reference level of mucin secretion;

M-3B-2: 100 µM MA-PSD provided a mucin secretion level relative to media control of 285% (*);

M-3B-3: 10 µM MA-PSD provided a mucin secretion level relative to media control of 91%; and M-3B-4: 1 µM MA-PSD provided a mucin secretion level relative to media control of 102%.

The single asterisk (*) indicates that the response was statistically different than the media control (M-3B-1).

The single asterisk (*) in M-3B-2 indicates that the response to 100 µM of MA-PSD peptide was statistically different than the media control (M-3B-1), whereas no statistically significant difference was seen when 1 or 10 µM of peptide was used (M-3B-3 and M-3B-4).

Example 10

Inhibition of Mucus Secretion by Antisense Oligonucleotides

Using an antisense oligonucleotide directed to the endogenous human MARCKS gene, mucus secretion was inhibited in vitro in human airway epithelial cells. The in vitro assay system as described in Example 5 was utilized to test the effects of antisense oligonucleotides to MARCKS mRNA.

An antisense oligonucleotide was constructed by a commercial supplier (Chemicon International, Temecula, Calif.; in conjunction with Biognostik GmbH, Gottingen, Germany) based on the human MARCKS gene sequence of Sakai et al. (*Genomics* 14:175 (1992); GenBank accession number D10522, D90498). A control oligonucleotide was also constructed.

The oligonucleotides were administered to the differentiated airway epithelial cultures by incubation in media containing the oligonucleotides (5 µM) for three days. The oligonucleotide was supplied to the apical surface of the cells in 0.4 ml of media containing lipofectin reagent (2 µg/ml; Gibco BRL). Cells were incubated with the oligonucleotide in the presence of lipofectin for 24 hours. Following a media change, cells were incubated with the oligonucleotide alone for an additional 48 hours. To test the ability of the oligonucleotides to affect stimulated mucus secretion, test cells were stimulated for minutes with 100 nM PMA and 1 µM 8-Br-cGMP (activators of PKC and PKG, respectively).

The effects of a MARCKS antisense oligonucleotide on stimulated mucin secretion by human bronchial epithelial cells in vitro are presented as Results-M-5, as follows:

M-5-1: media/control, provided a mucin secretion level normalized to 100%;

M-5-2: cells stimulated with 100 nM PMA and 1 µM 8-Br-cGMP provided a mucin secretion level of 157% of the control level (*);

M-5-3: cells stimulated with 100 nM PMA and 1 µM 8-Br-cGMP in the presence of 5 µM of control oligonucleotide provided a mucin secretion level of 164% of the control level (*); and M-5-4: cells stimulated with 100 nM PMA and 1 µM 8-Br-cGMP in the presence of 5 µM antisense oligonucleotide provided a mucin secretion level of 141% of the control level (**).

Single asterisks (*) indicate that the measured response was statistically different from the media control (M-5-1), and double asterisks (**) indicate that the response was statistically different from that observed in stimulated cells that were not exposed to the any oligonucleotide (M-5-2).

Mucus secreted from the airway epithelial cells after stimulation by PKC and PKG activators was assessed using an ELISA (antibody capture method). The control oligonucleotide (see M-5-3) had no effect on stimulated mucus secretion. In contrast, the antisense oligonucleotide (see M-5-

4) caused a statistically significant decrease in mucus secretion compared to stimulated levels.

These results indicate that MARCKS antisense oligonucleotides inhibit stimulated mucus secretion, although a basal level of mucus secretion can be maintained by selection of appropriate dosages. In contrast, control oligonucleotides had no effect on stimulated secretion.

Example 11

TNF-α Up-Regulates MARCKS Expression and Augments

Mucin Hypersecretion

NHBE cells were incubated with 10 ng/ml human recombinant TNF-α or medium alone for 4 hrs, then stimulated with PMA (100 nM)+8-Br-cGMP (1 μM) for 15 min, or UTP (0.1 mM) for 2 hrs. Secreted mucin was collected and measured by ELISA. Total RNA and protein were isolated from treated cells. MARCKS mRNA was assessed by Northern hybridization, and protein by the Western Blot technique. The results are presented as Results-M-6A, Results-M-6B, and Results-M-6C which together illustrate that TNF-α up-regulates MARCKS expression and augments mucin hypersecretion.

Results-M-6A provide the following and indicate an increase in MARCKS mRNA in cells incubated with TNF-α (see M-6A-2, below) compared to cells incubated in medium alone (see M-6A-1, below):

M-6A-1: NHBE cells incubated with media/control for 4 hours then stimulated with PMA (100 nM)+8-Br-cGMP (1 μM) for 15 min provided a control MARCKS mRNA level normalized to 100%;

M-6A-2: NHBE cells incubated with 10 ng/ml human recombinant TNF-α for 4 hours then stimulated with PMA (100 nM)+8-Br-cGMP (1 μM) for 15 min provided a MARCKS mRNA level of 115% relative to the control level as 100%.

Results M-6B provide the following and indicate a three- to four-fold increase in MARCKS protein in cells incubated with TNF-α (see M-2, below) as compared with cells incubated with medium only (see M-1, below):

M-6B-1: NHBE cells incubated with media/control for 4 hours then stimulated with PMA (100 nM)+8-Br-cGMP (1 μM) for 15 min provided a MARCKS protein level normalized to 100%;

M-6B-2: NHBE cells incubated with 10 ng/ml human recombinant TNF-α for 4 hours then stimulated with PMA (100 nM)+8-Br-cGMP (1 μM) for 15 min provided a MARCKS protein level of 352% relative to the control level as 100%.

Results M-6C provide the following and indicate that in cells incubated with TNF-α, mucin hypersecretion was significantly augmented in response to subsequent stimulation by PMA+8-Br-cGMP or UTP when compared to mucin secretion of cells incubated in medium only. Data are presented as mean±SEM (n=6 at each point).

M-6C-1: media/control provided a mucin secretion level normalized to 100%;

M-6C-2: cells incubated with TNF-α provided a mucin secretion level of 109% that of control levels;

M-6C-3: cells incubated with PMA (100 nM)+8-Br-cGMP (1 μM) absent TNF-α provided a mucin secretion level of 191% that of control levels (*);

M-6C-4: cells incubated with PMA (100 nM)+8-Br-cGMP (1 μM) plus TNF-α provided a mucin secretion level of 255% that of control levels (*)(†);

M-6C-5: cells incubated with UTP (0.1 mM) absent TNF-α provided a mucin secretion level of 152% that of control levels (*); and M-6C-6: cells incubated with UTP (0.1 mM) and TNF-α provided a mucin secretion level of 191% that of control levels (*)(†).

Single asterisks (*) indicate a statistically significant difference from control (medium-only) samples (p<0.05). Single cross marks (†) indicate a statistically significant difference from stimulus (p<0.05).

Northern Blot and results M-6A data show an increase in MARCKS mRNA in cells incubated with TNF-α (M-6A-2) compared to cells incubated in medium alone (M-6A-1).

Western-blot and results M-6B data show a three- to four-fold increase in MARCKS protein in cells incubated with TNF-α (M-6B-2) as compared with cells incubated with medium only (M-6B-1).

Results M-6C show that in cells incubated with TNF-α (M6C-4 and M-6C-6), mucin hypersecretion was significantly augmented in response to subsequent stimulation by PMA+8-Br-cGMP or UTP when compared to mucin secretion of cells incubated in medium only. Data are presented as mean±SEM (n=6 at each point). Single asterisks (*) indicate a statistically significant difference from control (medium-only) samples (p<0.05). Single cross marks (†) indicate a statistically significant difference from stimulus (p<0.05).

Example 12

Okadaic Acid Blocks Stimulated Mucin Hypersecretion

NHBE cells were pre-incubated with okadaic acid (500 nM) for 15 min at 37° C./5% $CO_2$, then stimulated with PMA (100 nM)+8-Br-cGMP (1 μM) for 15 min, or with UTP (0.1 mM) for 2 hours. Secreted mucin in the apical medium was collected and assayed by ELISA. The results are presented as Results-M-7 as follows and show that okadaic acid, a phosphatase inhibitor, blocks mucin hypersecretion induced by PMA+8-Br-cGMP or UTP:

M-7-1: incubation with medium alone for 30 min produces mucin levels which are normalized to 100%;

M-7-2: pre-incubation with medium alone for 15 min, then incubation with PMA (100 nM)+8-Br-cGMP (1 μM) for an additional 15 min produces mucin levels which are 212% of control (*);

M-7-3: pre-incubation with okadaic acid for 15 min, then co-incubation with PMA (100 nM)+8-Br-cGMP (1 μM) for an additional 15 min produces mucin levels which are 155% of control (†), representing a 27% reduction in mucin secretion level from levels observed in M-7-2;

M-7-4: incubation with medium alone for 2 hrs produces mucin levels which are 100% of control;

M-7-5: pre-incubation with medium alone for 15 min, then incubation with UTP for an additional 2 hrs produces mucin levels which are 159% of control (*);

M-7-6: pre-incubation with okadaic acid for 15 min, then co-incubation with UTP for an additional 2 hrs produces mucin levels which are 110% of control (†), representing a 31% reduction in mucin secretion level from levels observed in M-7-5.

Data are presented as mean±SEM (n=6 at each point). Single asterisks (*) indicate a statistically significant difference from control (p<0.05). Single cross marks (t) indicate statistically significant difference from stimulus (p<0.05).

These results indicate that okadaic acid, a phosphatase inhibitor, blocks (inhibits or attenuates) mucin hypersecretion induced by PMA+8-Br-cGMP or UTP.

Example 13

Mucin Hypersecretion Induced by UTP is Inhibited by Inhibitors of the Mucus Secretion Signaling Pathway NHBE cells were pre-incubated with the indicated inhibitor (described below) for 15 min, then stimulated with UTP (0.1 mM) for 2 hours. Secreted mucin in the apical medium was collected and assayed by ELISA. The results are designated as Results-M-8 and show that mucin hypersecretion induced by UTP involves activation of PKC and PKG.

M-8-1: incubation with medium alone provided a mucin secretion level normalized to 100%;

M-8-2: incubation with 0.1 mM UTP provided a mucin secretion level which was 161% of control level (*);

M-8-3: incubation with 0.1 mM UTP+500 nM calphostin C (an inhibitor of PKC) provided a mucin secretion level which was 121% of control level (†);

M-8-4: incubation with 0.1 mM UTP+10 μM $R_p$-8-Br-PET-cGMP (an inhibitor of PKG) provided a mucin secretion level which was 130% of control level (t);

M-8-5: incubation with 0.1 mM UTP+50 μM LY83583 (an inhibitor of soluble guanylyl cyclase) provided a mucin secretion level which was 112% of control level (†); and M-8-6: incubation with 0.1 mM UTP+500 nM KT5720 (an inhibitor of PKA) provided a mucin secretion level which was 160% of control level (*).

Data are presented as mean±SEM (n=6 at each point). Single asterisks (*) indicate a statistically significant difference from control ($p<0.05$). Single cross marks (t) indicate a statistically significant difference from UTP stimulation ($p<0.05$).

Example 14

Inhibition of Release of Proinflammatory factors by MANS and MANS-Related Peptides Four different leukocyte types or models that secrete specific granule contents in response to phrobol ester induced activation of PKC were used in these experiments. In addition to neutrophils, three types of human leukocyte cell lines, specifically the promyelocytic cell line HL-60 clone 15, the monocytic cell line U937, and the lymphocyte natural killer cell line NK-92 were purchased from American Type Culture Collection (ATCC; Rockville, Md.), and used in the present experiments. In all cases, the cells were pre-incubated with a range of concentrations of a synthetic peptide identical to (or an analog thereof) the 24 amino acid MANS (myristoylated N-terminal sequence) peptide with the amino acid sequence of MA-GAQFSKTAAKGEAAAERPGEAAVA (SEQ ID NO: 1), wherein MA represents myristoyl moiety; or a missense control peptide designated as RNS (random N-terminal sequence) peptide which has an amino acid sequence of MA-GTAPAAEGAGAEVKRASAEAKQAF (SEQ ID NO: 26) in which the same 24 amino acids as in MANS are arranged in a random sequence, which possesses less than 13% sequence homology to MANS peptide sequence.

1. Inhibition of Release of Myeloperoxidase (MPO) from Human Neutrophils:

Human neutrophil isolation: Human neutrophils were isolated according to a slightly modified method previously described by Akasaki T, Koga H, and Sumimoto H., Phosphoinositide 3-kinase-dependent and -independent activation of the small GTPase Rac2 in human neutrophils, J. Biol. Chem. 274:18055-18059, 1999. Alternatively, human neutrophils were isolated as previously described (see Takashi S, Okubo Y, Horie S. Contribution of CD54 to human eosinophil and neutrophil superoxide production. J. Appl. Physiol. 91:613-622, 2001) with slight modifications. Briefly, heparinized venous blood was obtained from normal healthy human volunteers, diluted with RPMI-1640 (Cellgro; Mediatech, Inc., Herndon, Va.) at a ratio of 1:1, layered onto a Histopaque (density, 1.077 g/ml; Sigma-Aldrich Co., St. Louis, Mo.), and centrifuged at 400 g for 20 min at 4° C. The supernatant and mononuclear cells at the interface were carefully removed, and erythrocytes in the sediment were lysed in chilled distilled water. Isolated granulocytes were washed twice with Hanks' balanced salts solution (HBSS) and resuspended in HBSS on ice. The neutrophils used for the experiments were of >98% purity with <2% contamination by eosinophils, and the viability was >99% as determined by Trypan blue dye exclusion.

Measurement of released MPO activity: Purified human neutrophils suspended in HBSS were aliquoted at $4\times10^6$ cells/ml in 15 ml tubes and preincubated with either 50 or 100 μM of test peptide (dissolved in PBS, pH 7.0) for 10 min at 37° C. The cells were then stimulated with 100 nM phorbol 12-myristate 13-acetate (PMA) for up to 3 hrs. The reaction was terminated by placing the tubes on ice and centrifugation at 400 g for 5 min at 4° C. Secretions were quantified by using as a standard, human MPO.

MPO activity in the cell supernatant was assayed using tetramethylbenzidine (TMB) based on a previously established technique (Paige L, Mahmudi-Azer S, Bablitz B, Hage S C, Velazquez J R, Man S F P, and Moqbel R. Rapid Mobilization of intracellularly stored RANTES in response to Interferon-γ in human eosinophils. Blood, 94:23-32, 1999). Briefly, 100 μl of TMB substrate solution was added to 50 μl of cell supernatants or standard human MPO (EMD Biosciences, Inc., San Diego, Calif.) in a 96-well microtiterplate followed by incubation at room temperature for 15 min. The reaction was terminated by addition of 50 μl of 1M H2SO4 and absorbance was read at 450 nm in a spectrophotometric microplate reader (Molecular Devices, Sunnyvale, Calif.).

2. Inhibition of Eosinophil peroxidase (EPO) Release from HL-60 Cells:

The human promyelocytic cell line (Fischkoff S A, Graded increase in probability of eosinophilic differentiation of HL-60 promyelocytic leukemia cells induced by culture under alkaline conditions. Leuk. Res., 12:679-686, 1988; Rosenberg H F, Ackerman S J, Tenen D G. Human eosinophil cationic protein: molecular cloning of a cytotoxin and helminthotoxin with ribonuclease activity. J. Exp. Med., 170:163-176, 1989), HL-60 clone 15, is eosinophil-like promyelocytic human cell line which was purchased from American Type Culture Collection (ATCC) Rockville, Md. (catalog #CRL-1964). The cells were maintained in medium consisting of RPMI 1640 with glutamine supplemented with 10% heat inactivated fetal bovine serum (Gibco, Carlsbad, Calif.), 50 IU/mL penicillin, 50 μg/mL streptomycin, and 25 mM HEPES buffer, pH 7.8 at 37° C. in an atmosphere containing 5% CO2. Final differentiation of an eosinophil-like phenotype was initiated by culturing the cells at $5\times10^5$ cells/mL in the above medium containing 0.5 mM butyric acid (Sigma-Aldrich) for 5 days as previously described by Tiffany H L, Li F, and Rosenberg H F, Hyperglycosylation of eosinophil ribonuclease in a promyelocytic leukemia cell line and in differentiated peripheral blood progenitor cells J. Leukoc. Biol. 58:

49-54, 1995; and by Tiffany H L, Alkhatib G, Combadiere C, Berger E A, and Murphy P M., CC Chemokine receptors are differentially regulated by IL-5 during maturation of eosinophilic HL-60 cells. J. Immunol. 160:1385-1392, 1998. The cells were washed and resuspended at $2.5 \times 10^6$ per mL in phenol free RPMI-1640 (Cellgro; Mediatech Inc.). Aliquots of cells in 15 mL plastic tubes were preincubated with indicated concentration of test peptide (dissolved in PBS, pH 7.0) for 10 minutes followed by treatment of the cells with 100 nM PMA for 2 hours. The reaction was terminated by placing the tubes on ice and centrifugation of cells at 400 g for 5 min at 4° C. The eosinophil peroxidase (EPO) activity released by HL-60 clone 15 cells was assayed using TMB according to a previously established technique Paige et al (see above) and by Lacy P, Mahmudi-Azer S, Bablitz B, Hagen S C, Velazquez J R, Man S F, Moqbel R. Rapid mobilization of intracellularly stored RANTES in response to interferon-gamma in human eosinophils. Blood 94:23-32, 1999. Briefly, add 50 µL aliquots of the supernatant to 96-well microtiter plate followed by addition of 100 µL of the tetramethylbenzidine (TMB) substrate solution and incubate at room temperature for 15 minutes. The reaction was terminated by addition of 50 µL of 1.0 M sulfuric acid and absorbance was read at 450 nm in a spectrophotometric microplate reader (Molecular Devices, Sunnyvale, Calif.). The amount of secreted EPO was expressed as percentage of total content using the amount obtained in the same number of triton X-100-lysed cells.

Because standard EPO from HL-60 clone 15 cells was not available to use for quantification, we measured both released and intracellular (from lysed cells) levels of EPO, and expressed the released EPO as a percentage of total (intracellular and released) for each. To measure intracellular EPO in HL-60 clone 15 cells, appropriate aliquots of 0.1% triton X-100-lysed cells were taken for quantification of intracellular EPO as described above. All data are expressed as percentage of control to minimize variability between cultures.

3. Inhibition of Lysozyme Release from U937 Cells:

Because standard EPO from HL-60 clone 15 cells was not available to use for quantification, we measured The monocytic leukemia cell line U937 was used to assess secretion of lysozyme (Hoff T, Spencker T, Emmendoerffer A., Goppelt-Struebe M. Effects of glucocorticoids on the TPA-induced monocytic differentiation. J. Leukoc. Biol. 52:173-182, 1992; Balboa M A, Saez Y, Balsinde J. Calcium-independent phospholipase A2 is required for lysozyme secretion in U937 promonocytes. J. Immunol. 170:5276-5280, 2003; Sundstrom C, Nilsson K. Establishment and characterization of a human histiocytic lymphoma cell line (U-937). Int. J. Cancer 17:565-577, 1976).

U937 is a monocyte-like human cell line which was purchased from American Type Culture Collection (ATCC) Rockville, Md. (catalog #CRL-15932). The cells were maintained in medium consisting of RPMI 1640 with glutamine supplemented with 10% heat inactivated fetal bovine serum (Gibco, Carlsbad, Calif.), 50 IU/mL, penicillin, 50 µg/mL streptomycin at 37° C. in an atmosphere containing 5% $CO_2$. U937 cells were washed and resuspended at $2.5 \times 10^6$ cells/mL in phenol red free RPMI-1640 medium (Cellgro, Mediatech Inc.). Aliquots of cells in 15 mL plastic tubes were preincubated with indicated concentrations of test peptides (dissolved in PBS, pH 7.0) for 10 min at 37° C. The cells were then stimulated with 100 nM PMA for 1 hour. The cells were then centrifuged at 400×g for 5 min at 4° C. Lysozyme released from U937 cells was measured using spectrophotometric assay as described previously by Ralph et al., 1976. (Ralph P, Moore M A S, and Nilsson K. Lysozyme synthesis by established human and murine histocytic lymphoma cell lines. J. Exp. Med. 143:1528-33, 1976). Briefly. 100 µL of supernatants were placed in a 96-well microtiter plate and mixed with 100 µL of a *Micrococcus lysodeikticus* (Sigma-Aldrich) suspension (0.3 mg/mL in 0.1 M sodium phosphate buffer, pH 7.0), incubated for 10 hours at room temperature and decrease in absorbance at 450 nm was measured. Chicken egg white lysozyme (EMD Biosciences) was used as a standard.

Lysozyme secretion by U937 cells was increased by PMA stimulation after 1-hour incubation, and increased even more at 2 hours. The PMA stimulated lysozyme secretion was significantly attenuated by pre-incubation of the cells with 50 to 100 µM of MANS or its truncated analogs. However, the RNS peptide did not affect PMA-enhanced lysozyme secretion at any of the time points or concentrations tested.

4. Inhibition of Release of Granzyme from NK-92 Cells.

The lymphocyte natural killer cell line NK-92 was used to assess release of granzyme (Gong J H, Maki G, Klingemann H G. Characterization of a human cell line (NK-92) with phenotypical and functional characteristics of activated natural killer cells. Leukemia 8:652-658, 1994; Maki G, Klingemann H G, Martinson J A, Tam Y K. Factors regulating the cytotoxic activity of the human natural killer cell line, NK-92. J. Hematother. Stem Cell Res., 10:369-383, 2001; Takayama H, Trenn G, Sitkovsky M V. A novel cytotoxic T lymphocyte activation assay. J. Immunol. Methods 104:183-190, 1987).

Measurement of NK cell granzyme secretion: Granzyme secreted from NK-92 cells was assayed by measuring hydrolysis of Nα-benzyloxycarbonyl-L-lysine thiobenzyl ester (BLT, EMD Bioscience, Inc.) essentially as described previously (Takayama H. Trenn G, Sitkovsky M V. A novel cytotoxic T lymphocyte activation assay. J. Immunol. Methods 104:183-190, 1987). An aliquot of 50 µl of supernatant was transferred to a 96-well plate, and 150 µl of 0.2 mM solution of BLT and 0.22 mM DTNB (Sigma-Aldrich Co.) in phosphate-buffered saline (PBS, pH 7.2) was added to the supernatant. Absorbance at 410 nm was measured after incubation for 30 min at room temperature. Results were expressed as percentage of total cellular enzyme content, using the amount obtained in the same number of triton X-100-lysed cells.

Because standard granzyme from NK-92 cells was not available to use for quantification, we measured both released and intracellular (from lysed cells) levels of granzyme, and expressed the released granzyme as a percentage of total (intracellular and released) for each. To measure intracellular granzyme from NK-92 cells, appropriate aliquots of 0.1% triton X-100-lysed cells were taken for quantification of the enzyme as described above. All data are expressed as percentage of control to minimize variability between cultures.

At 2 hour incubation with 100 nM PMA, relative to granzyme secretion by NK-92 cells of the control as 100%, the PMA control reference measured at about 220%; the sample containing 100 µM MANS give about 60% reduction in granzyme secretion by NK-92 cells relative to the PMA control reference. Thus, granzyme secretion by NK-92 cells was increased over two-fold at 2 hours. MANS (100 µM) attenuated granzyme secretion at 2 hrs after incubation. The RNS peptide did not affect PMA-enhanced granzyme secretion at any of the time points or concentrations tested.

Cytotoxicity: None of the treatments generated a toxic response in the cells, as assessed by LDH retention/release (data not shown) (see also Park J-A, He F, Martin L D, Li Y, and Adler K B. Human neutrophil elastase induces hypersecretion of mucin from human bronchial epithelial cells in vitro via a PKCδ-mediated mechanism. Am. J. Pathol., 167: 651-661, 2005).

The following table (Table 1) presents data relevant to activity in inhibition of MARCKS-related release of mucin of representative peptides of the invention (data relevant to the non-representative and relatively inactive RNS peptide are presented for comparative purposes only); solubility data of these peptides in 0.5 N saline which is considered to be representative of a pharmaceutical composition sterilized, for example, by filtration through a 0.2 micron filter, and made isotonic, and which is then suitable for inhalation administration in a subject as an aerosol or spray; and activity relevant to mucus or mucin % inhibition, MPO % inhibition, EPO % inhibition, lysozyme % inhibition, and granzyme % inhibition, which data are relevant to inhibition of MARCKS-related mucus secretion and MARCKS-related release of mediators of inflammation.

TABLE 1

Inhibition of MARCKS-related mucus secretion and MARCKS-related release of mediators of inflammation by myristoylated peptides and their solubilities in 0.5N saline

| SEQ ID NO: | N-[1] | Amino Acid Sequence | % Inhibition Mucin[2] | MPO[2] | EPO[3] | Lysozyme[3] | Granzyme[3] | Solubility[4] |
|---|---|---|---|---|---|---|---|---|
| 1 | MA | GAQFSKTAAKGEAAAERPGEAAVA | 81.5 | 31.2 | 46.1 | 40.8 | 76.0 | <5.0 |
| 5 | MA | GAQFSKTAAKGEAAAERPGE | 77 | | 33.6 | 99 | | <5.0 |
| 9 | MA | GAQFSKTAAKGEAAAE | 68 | | 30.3 | 99 | | >2.0 |
| 13 | MA | GAQFSKTAAKGE | 77 | 43.2 | 25.2 | 85.2 | | >2.0 |
| 15 | MA | GAQFSKTAAK | 67.5 | | 37.4 | 56.6 | | >10 |
| 26 | MA | GTAPAAEGAGAEVKRASAEAKQAF | 0 | 0 | 0 | 0 | 29.5 | >15 |

[1]= Chemical moiety at N-terminal amino acid; MA = myristoylation of the peptide
[2]= at 100 μM of test peptide
[3]= at 50 μM of test peptide
[4]= in mg/mL in 0.5 N Saline at pH 6.5

In all cases, the cells were preincubated for 10 minutes with a range of concentrations of a synthetic peptide identical to the 24 amino acid MARCKS N-terminus, MANS (myristoylated N-terminal sequence) peptide, MA-GAQFSKTAAKGEAAAERPGEAAVA (SEQ ID NO:1) wherein MA is myristoyl moiety attached to the N-terminal amine of MANS peptide by an amide bond), or a missense control peptide, RNS (Random N-terminal sequence) peptide with amino acid sequence of (MA-GTAPAAEGAGAEVKRASAEAKQAF-(SEQ ID NO: 26) which consists of the same 24 amino acids but arranged in random order sequence which possesses less than 13% sequence identity to the MANS peptide sequence.

In each of the cell types, MANS or its truncated peptides, but not RNS, attenuates release of inflammatory mediators in a concentration-dependent manner. A useful time course of observation is 0.5-3.0 hrs. The results are consistent with the N-terminal region of the MARCKS protein being involved in intracellular pathways leading to leukocyte degranulation.

Example 15

Human Neutrophil Chemotactic Migration Assay

In one aspect, inflammation causes certain white cells, specifically neutrophils to migrate towards the inflamed tissue site. An infection caused by environmental pathogen often results in an inflammatory response. Inflammation causes release of certain “attractant” or “chemotactic factors”, which are responsible for infiltration of white cells towards the inflamed tissue. This phenomenon is called chemotaxis. Therefore, if one measures the number of migrated white cells as a marker of inflammation, one could indirectly measure the extent of inflammation.

In a series of three experiments, the data show that certain peptides consistently and specifically inhibited the chemo-attractant driven migration of human neutrophils. The three chemo-attractant tested were (i) formylated Methionine-Leucine-Phenylalanine (fMLP), a bacterial derived chemotactic agent, (ii) leukotriene B4 (LTB4), and (iii) Platelet Activating Factor (PAF).

Human neutrophils were isolated from heparinized whole blood collected from healthy adult donors via cephalic venipuncture by a slightly modified method as described by Akasaki et al., 1999 (Akasaki T, Koga H, and Sumimoto H., Phosphoinositide 3-kinase-dependent and -independent activation of the small GTPase Rac2 in human neutrophils, J. Biol. Chem. 274:18055-18059, 1999). The blood was mixed with dextran (final concentration 1.4% dextran) and then allowed to settle for 60 minutes, after which time the leukocyte rich plasma was collected and layered onto 5 mL of Ficoll-Paque PLUS in 15 ml, conical tubes. The plasma was centrifuged at 1800 rpm for 20 minutes at room temperature. The residual erythrocytes were lysed utilizing a hypotonic saline and the remaining neutrophils were re-suspended in Hank’s balanced salt solution containing 20 mM HEPES and 8.9 mM sodium bicarbonate without calcium or magnesium (HBSS), yielding neutrophils that were greater than 98% pure and greater than 99% viable.

Neutrophil migration assay was performed according to the method described by Frevert C W, Wong V A, Goodman R B, Goodwin R, and Martin T R., Rapid fluorescence-based measurement of neutrophil migration in vitro, J. Immunol. Methods, 213:41-52, 1998. Human neutrophils were labeled with the fluorescent dye calcein for 30 minutes at room temperature. Cells were then washed and resuspended in a migration buffer containing HBSS with 2% FCS. Cells were treated with buffer alone or with the indicated test peptide (50 μM) for 30 minutes at 37° C. Treated cells ($1\times10^4$ cells) were then placed on the upper side of a ChemoTx® chemotaxis plate (Neuroprobe, Gaithersburg, Md.) membrane (2 μm pore size). Lower wells of the plate were filled with migration buffer alone or with buffer containing fMLP (100 nM), LTB4 (100 nM), or PAF (100 nM). Wells containing $1\times10^4$ labeled cells were used as standards to calculate migration percentage. Cells were allowed to migrate for 1 hour at 37° C. After incubation, cells on the top of the filter were washed away with PBS. Followed by this, 0.5 mM EDTA was added to the top of the filter for 5 min to detach adherent cells and the membrane was again washed. The plate was then centrifuged at 1000 rpm for 1 min. The filter was removed and the fluorescence was measured in the lower wells (485 nm excitation, 530 nm emission wavelength) using an fMax fluorescence plate reader (Molecular Devices, Sunnyvale, Calif.). Percent migration was determined by dividing the fluorescence of each well by the fluorescence of the standard wells containing $1\times10^4$ labeled cells. A lesser number of migrated neutrophils in the bottom compartment is indicative of the test peptide being an inhibitor of inflammation.

TABLE 2

Inhibition of Human Neutrophil Chemotaxis by Myristoylated Peptides

| Peptide Sequence[1] | SEQ ID NO: | Neutrophil Migration (% Inhibition)[2] | | |
|---|---|---|---|---|
| | | fMLP | LTB4 | PAF |
| MANS | 1 | 90.0 | 91.8 | 86.4 |
| RNS peptide | 26 | 0.7 | 0 | 62.1 |
| MA-GAQFSKTAAKGEAAAERPGE | 5 | 69.1 | 76.8 | 88.4 |
| MA-GAQFSKTAAKGEAAAE | 9 | 84.8 | 90.3 | 72.7 |
| MA-GAQFSKTAAKGE | 13 | 81.8 | 82.7 | 85.7 |
| MA-GAQFSKTAAK | 15 | 88.6 | 85.5 | 87.2 |
| MA-GAQFSKTA | 17 | 92.2 | N/A | N/A |

[1]= MA- designates N-terminal myristoylation of the peptide
[2]= 0 = inactive; N/A—Not available Example 16

In Vivo Inhibition of Lipopolysaccharide (LPS)-Induced Lung in Inflammation by MANS and Related Peptides This example was performed essentially according to methods described by Cox, G, Crossley, J., and Xing, Z.; Macrophage engulfment of apoptotic neutrophils contributes to the resolution of acute pulmonary inflammation in vivo; Am. J. Respir. Cell Mol. Biol. 12:232-237, 1995; Hirano S., Quantitative time-course profiles of bronchoalveolar lavage cells following intratracheal instillation of lipopolysaccharide in mice. Ind. Health 35:353-358, 1997; and Ulich T R, Watson L R, Yin S M, Guo K Z, Wang P, Thang H, and del Castillo, J. Am. J. Pathol. 138:1485-1496, 1991.

Thus, six to seven week old CD1 female mice weighing 15-20 grams were obtained from Charles River laboratories and housed in groups of 5 mice per cage. The animals received standard rodent diet and filtered water ad libitum. The animals were housed under NIH prescribed guidelines at standard temperature (64° to 79° F.) and relative humidity of 30 to 70%.

Four treatment groups of mice, with 5 animals in each group, were treated either with PBS followed by PBS, with PBS followed by LPS, with (myristoylated) MANS peptide followed by LPS, or with peptide of SEQ ID NO: 15 (MA-GAQFSKTAAK) followed by LPS.

Intranasal peptide instillation pre-treatment: A peptide of the invention to be evaluated in vivo for its ability to inhibit or reduce LPS-induced lung inflammation was dissolved in PBS at a concentration of 1 mM. Animals, anesthetized with 0.8% isofluorane by inhalation, were pretreated with 2×10 µl intranasal bolus of the peptide solution into one nostril 30 minutes prior to subsequent instillation with LPS.

Intranasal LPS instillation: Lipopolysaccharide (LPS) Endotoxin (*Escherichia coli* Serotype 011:B4 derived endotoxin; Sigma, St Louis, Mo.; see Sigma product information sheet L4130 titled Lipopolysaccharides from *Escherichia coli* 011:B4) was dissolved into phosphate buffered saline (PBS) at 2,500 µg/mL. To expose animals to endotoxin, a 10 µL intranasal bolus of 2,500 µg/ml endotoxin solution was administered to animals which had been anesthetized with 0.8% isofluorane by inhalation. The 10 µL bolus was applied into one nostril. Animals were monitored for labored breathing, lethargy, and decreased water/food intake following the endotoxin instillations.

Bronchoalveolar Lavage (BAL): Six hours after the last instillation, the animals were anesthetized (90 mg/kg Nembutal) and sacrificed by exsanguination. The lung was serially lavaged 2 times with 1.0 mL aliquots of PBS. The collected BAL fluid was centrifuged to remove the cells for subsequent counting and differential analysis. Recovered lavage fluid was used for analysis of total protein, myeloperoxidase (MPO), LDH, and hemoglobin.

Analysis: Aliquots of the BAL fluid were used immediately to assay for the levels of LDH, total protein, or hemoglobin (Hb) using the COBAS Fara analyzer (COBAS FARA II automated analyzer; Roche Diagnostic Systems Inc., Montclair, N.J.). An aliquot of BAL fluid was frozen at –80° C. for subsequent quantitation of myeloperoxidase (MPO) with a mouse-specific ELISA assay (Cell Sciences, Inc., Canton, Mass.). BAL data were analyzed by standard techniques to examine differences between the control and treatment groups.

Results demonstrating inhibition or reduction of inflammation by MANS peptide are presented in Table 3.

TABLE 3

In Vivo Inhibition of LPS-induced Pulmonary Inflammation by MANS Peptide
Average values of markers of inflammation in the presence of MANS Peptide

| Treatment Regime | Total cells counted | Total neutrophils counted | % Neutrophils of total cells | MPO (ng/mL) | Total Protein (ug/ml) | LDH (units/L) | Hb (g/dl) |
|---|---|---|---|---|---|---|---|
| PBS/PBS n = 5 | 157,020 | 29,317 | 18.7 | 3.28 | 125.60 | 68.20 | 0.00 |
| PBS/LPS n = 5 | 264,200 | 110,061 | 41.7 | 28.98 | 272.40 | 60.40 | 0.19 |
| MANS[1]/LPS n = 7 | 208,457 | 64,481 | 30.9 | 9.49 | 175.00 | 68.57 | 0.05 |

[1]= MANS peptide = SEQ ID NO: 1

Results demonstrating inhibition or reduction of inflammation and average values of markers of inflammation in the presence of the peptide (SEQ ID NO: 15) are provided in Table 4.

TABLE 4

In Vivo Inhibition of LPS-induced Pulmonary Inflammation by Myristoylated Peptide MA-GAQFSKTAAK (SEQ ID NO: 15)

| Treatment Regime | Total Cell Counts | Total Neutrophil counts | % Neutrophils of total counts | MPO (ng/mL) | Total Protein (µg/mL) | LDH (units/L) | Hb (g/dL) |
|---|---|---|---|---|---|---|---|
| PBS/PBS N = 5 | 303,060 | 48,057 | 15.9 | 5.57 | 126.00 | 88.20 | 0.00 |
| PBS/LPS n = 5 | 422,300 | 119,114 | 28.2 | 17.33 | 157.40 | 107.80 | 0.01 |
| SEQ ID NO: 15[1]/LPS n = 5 | 628,075 | 38,548 | 6.1 | 0.79 | 120.25 | 110.75 | 0.01 |

[1] = MA-GAQFSKTAAK = SEQ ID NO: 15

Data on inhibition of markers of inflammation by MANS peptide and myristoylated peptide (SEQ ID NO: 15) relative to PBS/LPS treatment are provided in Table 5.

TABLE 5

In Vivo Inhibition of LPS-induced Pulmonary Inflammation

| Treatment Regime | % Inhibition of neutrophil migration | % Inhibition of MPO |
|---|---|---|
| MANS[1]/LPS | 41.4 | 67.2 |
| SEQ ID NO: 15[2]/LPS | 67.6 | 95.4 |

[1] = MANS peptide = SEQ ID NO: 1
[2] = MA-GAQFSKTAAK = SEQ ID NO: 15

PBS/PBS indicates only PBS control was administered, and no LPS endotoxin was added to stimulate chemotactic neutrophil migration; PBS/LPS indicates LPS (endotoxin) was added to stimulate chemotactic neutrophil migration; MANS/LPS indicates pretreatment with MANS peptide in PBS followed by LPS stimulation to induce neutrophil migration. The percent of neutrophils in the total cell count in the LPS treatment groups was reduced from 41.7% to 30.9% by treatment with MANS peptide, and the measured MPO levels in the LPS treatment groups was reduced from 28.98 ng/mL to 9.49 ng/ml, by treatment with MANS peptide.

Example 17

Mouse Model of Ozone-Induced COPD

Oxidative stress by chemical irritants such as ozone is a widely recognized feature of chronic obstructive respiratory disease (COPD). See: Repine J E, Bast A, Lankhorst I, and the Oxidative Stress Study Group, Am. J. Respir. Crit. Care Med. 156:341-357, 1997; and also Harkema J R and Hotchkiss J A, Toxicology Letters, 68:251-263, 1993.

Ten-week-old Balb/C female mice were obtained from Charles River laboratories and housed under NIH guidelines in groups of 5 per cage. The animals received standard rodent diet and filtered water ad libitum. Three treatment groups of mice, 5 animals in each group, were each anesthetized by intraperitoneal injection of Ketamine (100 mg/kg) and Xylazine (20 mg/kg) and then pretreated by intratracheal administration with 25 L of either PBS alone, or a solution of 1.0 mM MANS peptide in PBS, or a solution of a 1.0 mM of a MANS-fragment-peptide designated as SEQ ID NO: 15 (MA-GAQFSKTAAK) in PBS. After 30 minutes, the animals were then placed in the appropriate custom-made chamber for ozone or forced air exposures. The animals were exposed to ozone for 2 hours (at ozone concentrations of 1-10 ppm by a slightly modified method described by Haddad et al, 1995. (Haddad E-B, Salmon M, Sun J, Liu S, Das A, Adcock I, Barnes P J, and Chung K F, FEBS Letters, 363:285-288, 1995). The ozone was generated using an ozone generator apparatus model OL80F/B from OzoneLab, Burton, British Columbia, Canada. Ozone concentration was continuously monitored using a Teledyne Photometric O3 Analyzer (model 400E, Teledyne Instruments, City of Industry, Calif.). Two additional groups of mice, each without any pretreatment, were either exposed to ozone under the same conditions or exposed to forced air under conditions similar to the ozone treatment group but absent ozone. After exposure, the animals were sacrificed by exsanguination and the lungs were serially lavaged 2 times with 1.0 mL aliquots of PBS. The collected bronchoalveolar lavage (BAL) fluid was centrifuged to remove the cells for subsequent counting and differential analysis. Recovered lavage fluid was used for protein and additional analysis of IL-6, IFNγ, and KC (murine IL-8 analog) by ELISA assay (assay kits obtained from R&D Systems, Minneapolis, Minn.).

The percent inhibition of neutrophil migration into the BAL fluid as a function of treatment groups and relative to a control group treated with PBS alone are provided in the table.

Data related to inhibition of ozone-induced neutrophil migration by MANS peptide and by myristoylated peptide SEQ ID NO: 15 in mice are found in Table 6.

TABLE 6

Inhibition of Ozone-induced Neutrophil Migration in Mice

| Treatment Group | % Neutrophils found in BAL fluid | % Inhibition of neutrophil migration into BAL fluid |
|---|---|---|
| MANS[1] + Ozone | 1.5 | 93.0 |
| SEQ ID NO: 15[2] + Ozone | 11.2 | 47.7 |
| PBS + Ozone | 21.4 | Not applicable |

TABLE 6-continued

Inhibition of Ozone-induced Neutrophil Migration in Mice

| Treatment Group | % Neutrophils found in BAL fluid | % Inhibition of neutrophil migration into BAL fluid |
|---|---|---|
| Ozone alone | 22.8 | Not applicable |
| Forced air | 0.2 | Not applicable |

[1]= MANS peptide = SEQ ID NO: 1
[2]= MA-GAQFSKTAAK = SEQ ID NO: 15

Concentrations of IL-6 in pg/ml in BAL fluid, as a function of intratracheal injection pretreatment and subsequent treatment with ozone, were obtained as follows. IL-6 levels were found to be: approximately 23 pg/ml in a group of mice pretreated with MANS peptide and then exposed to ozone; approximately 49 pg/ml in a group of mice pretreated with MANS-fragment-peptide SEQ ID NO: 15 and then exposed to ozone; approximately 197 pg/ml in a group of mice pretreated with PBS and exposed to ozone; approximately 400 pg/ml in a group of mice exposed directly to ozone without any pretreatment.

Concentrations of KC in pg/ml in BAL fluid, as a function of intratracheal injection pretreatment and subsequent treatment with ozone, were obtained as follows. KC levels were found to be: approximately 60 pg/ml in a group of mice pretreated with MANS peptide and then exposed to ozone; approximately 147 pg/ml in a group of mice pretreated wxith MANS-fragment-peptide SEQ ID NO: 15, and then exposed to ozone; approximately 240 pg/ml in a group of mice pretreated with PBS and exposed to ozone; approximately 467 pg/ml in a group of mice exposed directly to ozone without pretreatment; and approximately 23 pg/ml in a group of mice exposed to forced air.

Concentrations of IFNγ in pg/ml in BAL fluid as a function of intratracheal injection pretreatment and subsequent treatment with ozone were obtained as follows. IFNγ levels were found to be: approximately 13 pg/ml in a group of mice pretreated with MANS peptide and then exposed to ozone; approximately 9 pg/ml in a group of mice pretreated with MANS-fragment-peptide SEQ ID NO: 15 and then exposed to ozone; approximately 18 pg/ml in a group of mice pretreated with PBS and exposed to ozone; approximately 18 pg/ml in a group of mice exposed directly to ozone without pretreatment; and approximately 24 pg/ml in a group of mice exposed to forced air.

Administration of ozone to mice significantly increased infiltrated neutrophil cell numbers, as well as IL-6 and KC levels in the BAL. In comparison to the control group in which the mice were pretreated with PBS, the group pretreated with MANS peptide and the group pretreated with peptide SEQ ID NO: 15, each exhibited reduced neutrophil cell infiltration in the BAL fluid after ozone exposure (e.g., 93%±5% and 47.7%±5%, respectively vs. PBS control). In parallel, MANS peptide and peptide SEQ ID NO: 15 also markedly diminished KC concentrations (e.g., 75%±2% and 38%±5%, respectively, vs. PBS control) and IL-6 levels (e.g., 88%±8%, MANS and 75%±8% SEQ ID NO: 15 vs. PBS control) after ozone exposure but had little effect on interferon-γ levels. Collectively, these data evidence that MANS and SEQ ID NO: 15 peptides markedly diminish or inhibit ozone-induced neutrophil migration into the airways as well as decrease selective chemokine and cytokine. The IL-6 levels in the BAL fluids from animals pretreated with MANS peptide or peptide SEQ ID NO: 15 showed approximately 85% and 75% inhibition, respectively, compared to those pretreated with PBS. Also the KC levels in the BAL fluids from animals pretreated with MANS peptide or peptide SEQ ID NO: 15 showed approximately 80% and 40% inhibition compared to those pretreated with PBS.

Example 18

Chronic Bronchitis Model

The procedure is described by Voynow J A, Fischer B M, Malarkey D E, Burch L H, Wong T, Longphre M, Ho S B, Foster W M, Neutrophil Elastase induces mucus cell metaplasia in mouse lung, Am. J. Physiol. Lung Cell Mol. Physiol. 287:L1293-L1302, 2004 and is followed to develop a model of chronic bronchitis in the mouse. Specifically, goblet cell hyperplasia, a signature pathological feature of chronic bronchitis, is induced by chronic exposure of mice to human Neutrophil Elastase (NE) instilled into the airways.

Human NE are aspirated intratracheally by male Balb/c mice. A total of 30 mice (about 25-30 g in weight) are obtained commercially from a supplier such as Jackson Laboratories, Bar Harbor, Me. The mice are maintained on a 12 hr diurnal cycle, with food and water provided ad libitum. The animals receive NE by oropharyngeal aspiration on days 1, 4, and 7. Immediately after inhalational anesthesia with isofluorane (IsoFlo from Abbott Laboratories and Open-Circuit Gas Anesthesia System from Stoelting), animals are suspended by their upper incisors on a 60° incline board, and a liquid volume of human NE [50 ug (43.75 units)/40 μL PBS (Elastin Products, Owensville, Mo.) is delivered with the animal's tongue extended to the distal part of the oropharynx. With the tongue extended, the animal is unable to swallow, and the liquid volume is aspirated in the respiratory tract.

At 7 days after the last NE exposure, when the goblet cell hyperplasia modeling the airways in chronic bronchitis is at its maximum (see Voynow et al, 2004), mice (5 animals per group) are instilled intra-tracheally with 50 μL of either PBS (as control), or 100 uM of a solution of MANS peptide, a solution of RNS peptide, or a solution of a peptide such as SEQ ID NO: 15 dissolved in PBS. Fifteen minutes later, mucus secretion is triggered by administration of methacholine, using a Buxco system Nebulizer to provide a fine aerosol delivering methacholine at approximately 60 mM for 3 min. Fifteen minutes after methacholine administration, mice are sacrificed by inhalational exposure to 100% CO2 gas.

Histochemistry. After exposures described above, lungs from animals are flushed to remove blood, then are inflated with OCT (Optimum Cutting Temperature medium (Sakura Finetck, Torrance, Calif.), half diluted in saline. The lungs are immersed in 10% formaldehyde in PBS overnight at 4° C., and processed to paraffin wax. Five μm sections are treated with Periodic acid Schiff/haematoxylin to stain mucins in the airways, for example as described by Singer M, Vargaftig B B, Martin L D, Park J J, Gruber A D, Li Y, Adler K B, A MARCKS-related peptide blocks mucus hypersecretion in a murine model of asthma., Nature Medicine 10:193-196, 2004.

Histological mucus index. A histological mucus index (Whittaker L, Niu N. Temann U-A. Stoddard A, Flavell R A, Ray A. Horner R J, and Cohn L, Interleukin-13 mediates a fundamental pathway for airway epithelial mucus induced by CD4 T cells and interleukin-9, Am. J. Respir. Cell Mol. Biol. 27:593-602, 2002) is performed on AB/PAS-stained sections that include both central and peripheral airways. The slides are examined with a 10× objective, and images captured with a digital camera. A minimum of four representative cross- or sagittally sectioned airways is imaged per animal. Only airways where the complete circumference of the airway can be visualized and included in the image are analyzed. Airways that open directly in an alveolar space are not included. The extent of PAS-positive staining in each airway imaged will be semi-quantitatively determined by an examiner who does not know the treatment conditions for each section, using the following five-tier grading system: grade 0, no PAS staining; grade 1, 25% or less of the airway epithelium has PAS staining; grade 2, 26-50% of the airway epithelium has PAS staining; grade 3, 51-75% of the airway epithelium has PAS staining; and grade 4, >75% of the airway epithelium has PAS staining. This grading system is used to calculate a mucus index score for each group, and results are presented as means±SE.

All results are presented as means±standard error (n=5 animals, 10-20 sections for each). Significance levels will be calculated using one way ANOVA followed by Scheffe's test, using SPSS 6.1 software (*=significance between data with a threshold of $p<0.05$).

The foregoing examples are illustrative of the present invention and are not to be construed as limiting thereof. The invention is defined by the following claims, with equivalents of the claims to be included therein.

We claim:

1. A method of decreasing MARCKS-related mucus secretion and MARCKS-related release of mediators of inflammation from infiltrating inflammatory cells in tissues of a subject in need thereof comprising: administering to said subject a pharmaceutical composition comprising a pharmaceutically acceptable carrier in combination with an N-terminal myristoylated protein fragment of the N-terminal region of MARCKS protein, in a dual function therapeutically effective amount to reduce MARCKS-related secretion of at least one inflammatory mediator from at least one inflammatory cell in said subject and to reduce MARCKS-related mucus hypersecretion from at least one mucus secreting cell or tissue in said subject, whereby inflammation and mucus hypersecretion in said subject are reduced compared to that which would occur in the absence of said administration of said pharmaceutical composition, wherein said inflammatory mediator is secreted from an infiltrating inflammatory cell at a site of inflammation in the subject, and wherein said inflammation and mucus hypersecretion are caused by or are the clinical symptoms of a respiratory disease.

2. The method according to claim 1, wherein said N-terminal myristoylated protein fragment of the N-terminal region of MARCKS protein consists of the myristoylated N-terminal peptide (SEQ ID NO:1) or a N-terminal myristoylated peptide fragment thereof consisting of at least five contiguous amino acids of SEQ ID NO:1.

3. The method according to claim 2, wherein said N-terminal myristoylated peptide fragment consists of at least 10 amino acids of SEQ ID NO: 1.

4. The method according to claim 2, wherein said N-terminal myristoylated peptide fragment consists of at least 15 amino acids of SEQ ID NO: 1.

5. The method according to claim 2, wherein said N-terminal myristoylated peptide fragment consists of at least 20 amino acids of SEQ ID NO: 1.

6. The method according to claim 2, wherein said N-terminal myristoylated peptide fragment is selected from the group consisting of N-myristoyl-GAQFSKTAAKGEAAAERPGEAAV (SEQ ID NO: 2); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); N-myristoyl-GAQFSK (SEQ ID NO: 19); and N-myristoyl-GAQFS (SEQ ID NO: 20).

7. A method of decreasing MARCKS-related mucus secretion and MARCKS-related release of mediators of inflammation from infiltrating inflammatory cells in tissues of a subject in need thereof comprising:
administering to said subject a pharmaceutical composition comprising a pharmaceutically acceptable carrier and a combination of N-terminal myristoylated protein fragments of the N- terminal region of MARCKS protein, which fragments are selected from the group consisting of N-myristoyl-GAQFSKTAAKGEAAAERPGEAAVA (SEQ ID NO: 1); N-myristoyl-GAQFSKTAAKGEAAAERPGEAAV (SEQ ID NO: 2); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); N-myristoyl-GAQFSK (SEQ ID NO: 19); and N-myristoyl-GAQFS (SEQ ID NO: 20).

8. The method according to claim 7, wherein said pharmaceutical composition comprises a combination selected from two of said N-terminal myristoylated protein fragments.

9. The method according to claim 1, wherein said respiratory disease is selected from the group consisting of asthma, chronic bronchitis, chronic obstructive pulmonary disease (COPD), bronchiectasis, emphysema, pneumonia, influenza, rhinitis, and the common cold.

10. The method according to claim 1, wherein said respiratory disease is selected from the group consisting of asthma, chronic bronchitis, and COPD.

11. The method according to claim 1, wherein said subject is a mammal.

12. The method according to claim 1, wherein said administering is selected from the group consisting of topical administration, parenteral administration, rectal administration, pulmonary administration, inhalation administration, nasal administration, and oral administration.

13. The method according to claim 12, wherein said pulmonary administration comprises use of an aerosol from a dry powder inhaler, from a metered dose inhaler, or from a nebulizer.

14. The method according to claim 1, wherein said inflammatory cell is a leukocyte.

15. The method according to claim 1, wherein said inflammatory cell is a granulocyte.

16. The method according to claim 1, wherein said inflammatory cell is selected from the group consisting of a neutrophil, a basophil, an eosinophil, a monocyte, a macrophage, and a mast cell.

17. The method according to claim 1, wherein the therapeutically effective amount of the pharmaceutical composition is administered orally, parenterally, rectally, or through an air passage.

18. The method according to claim 1, further comprising administering to said subject an additional agent selected from the group consisting of an antibiotic, an antiviral compound, an antiparasitic compound, an anti-inflammatory compound, and an immunosuppressant.

19. The method according to claim 1, wherein said mucus secreting cell is an epithelial cell in the airways of said subject.

20. A method of decreasing the MARCKS-related release of mediators of inflammation from infiltrating inflammatory cells of a subject in need thereof comprising: administering to said subject a pharmaceutical composition comprising a pharmaceutically acceptable carrier in combination with an N-terminal myristoylated protein fragment of the N-terminal region of MARCKS protein, in a therapeutically effective amount to reduce MARCKS-related release of at least one inflammatory mediator from at least one inflammatory cell in said subject, whereby inflammation in said subject is reduced compared to that which would occur in the absence of said administration of said pharmaceutical composition, wherein said inflammatory mediator is secreted from an infiltrating inflammatory cell at a site of inflammation in the subject, and wherein said inflammation is caused by or is a major clinical symptom of a bowel disease, a skin disease, an autoimmune disease or a pain syndrome.

21. The method according to claim 20, wherein said N-terminal myristoylated protein fragment of the N-terminal region of MARCKS protein consists of the N-terminal myristoylated peptide (SEQ ID NO:1) or a N-terminal myristoylated peptide fragment thereof consisting of at least five contiguous amino acids of SEQ ID NO:1.

22. The method according to claim 21, wherein said N-terminal myristoylated peptide fragment consists of at least 10 amino acids of SEQ ID NO: 1.

23. The method according to claim 21, wherein said N-terminal myristoylated peptide fragment consists of at least 15 amino acids of SEQ ID NO: 1.

24. The method according to claim 21, wherein said N-terminal myristoylated peptide fragment consists of at least 20 amino acids of SEQ ID NO: 1.

25. The method according to claim 21, wherein said N-terminal myristoylated peptide fragment is selected from the group consisting of N-myristoyl-GAQFSKTAAKGEAAAERPGEAAV (SEQ ID NO: 2); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); N-myristoyl-GAQFSK (SEQ ID NO: 19); and N-myristoyl-GAQFS (SEQ ID NO: 20).

26. The method according to claim 20, wherein said inflammatory cell is a leukocyte.

27. The method according to claim 20, wherein said inflammatory cell is a granulocyte.

28. The method according to claim 20, wherein said inflammatory cell is selected from the group consisting of a neutrophil, a basophil, an eosinophil, a monocyte, a macrophage, and a mast cell.

29. The method according to claim 20, further comprising administering to said subject an additional agent selected from the group consisting of an antibiotic, an antiviral compound, an antiparasitic compound, an anti-inflammatory compound, and an immunosuppressant.

30. The method according to claim 20, wherein said inflammation is caused by or is a clinical symptom of arthritis, ulcerative colitis, multiple sclerosis, Guillain-Barre syndrome, Crohn's disease, irritable bowel syndrome, psoriasis, rosacea, eczema, psoriasis, severe acne, systemic lupus erythematosus, or insulin-dependent diabetes mellitus.

31. The method according to claim 20, wherein said administering is selected from the group consisting of topical administration, parenteral administration, rectal administration, pulmonary administration, inhalation administration, nasal administration, and oral administration.

\* \* \* \* \*

```
                        SEQUENCE LISTING

<160> NUMBER OF SEQ ID NOS: 26

<210> SEQ ID NO 1
<211> LENGTH: 24
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 1

Gly Ala Gln Phe Ser Lys Thr Ala Ala Lys Gly Glu Ala Ala Ala Glu
1               5                   10                  15

Arg Pro Gly Glu Ala Ala Val Ala
            20

<210> SEQ ID NO 2
<211> LENGTH: 23
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 2

Gly Ala Gln Phe Ser Lys Thr Ala Ala Lys Gly Glu Ala Ala Ala Glu
1               5                   10                  15

Arg Pro Gly Glu Ala Ala Val
            20

<210> SEQ ID NO 3
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 3

Gly Ala Gln Phe Ser Lys Thr Ala Ala Lys Gly Glu Ala Ala Ala Glu
1               5                   10                  15

Arg Pro Gly Glu Ala Ala
            20

<210> SEQ ID NO 4
<211> LENGTH: 21
<212> TYPE: PRT
<213> ORGANISM: Homo sapiens
<220> FEATURE:
```

```
<221> NAME/KEY: MISC_FEATURE
<222> LOCATION: (1)..(1)
<223> OTHER INFORMATION: Peptide may have an N-terminal myristate moiety

<400> SEQUENCE: 4

Gly Ala Gln Phe Ser Lys Thr Ala Ala Lys Gly Glu Ala Ala Ala Glu
1               5                   10                  15

Arg Pro Gly Glu Ala
            20

<210> SEQ ID NO 5
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 5

Gly Ala Gln Phe Ser Lys Thr Ala Ala Lys Gly Glu Ala Ala Ala Glu
1               5                   10                  15

Arg Pro Gly Glu
            20

<210> SEQ ID NO 6
<211> LENGTH: 19
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 6

Gly Ala Gln Phe Ser Lys Thr Ala Ala Lys Gly Glu Ala Ala Ala Glu
1               5                   10                  15

Arg Pro Gly

<210> SEQ ID NO 7
<211> LENGTH: 18
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 7

Gly Ala Gln Phe Ser Lys Thr Ala Ala Lys Gly Glu Ala Ala Ala Glu
1               5                   10                  15

Arg Pro

<210> SEQ ID NO 8
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 8

Gly Ala Gln Phe Ser Lys Thr Ala Ala Lys Gly Glu Ala Ala Ala Glu
1               5                   10                  15

Arg
```

```
<210> SEQ ID NO 9
<211> LENGTH: 16
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 9

Gly Ala Gln Phe Ser Lys Thr Ala Ala Lys Gly Glu Ala Ala Ala Glu
1               5                   10                  15

<210> SEQ ID NO 10
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 10

Gly Ala Gln Phe Ser Lys Thr Ala Ala Lys Gly Glu Ala Ala Ala
1               5                   10                  15

<210> SEQ ID NO 11
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 11

Gly Ala Gln Phe Ser Lys Thr Ala Ala Lys Gly Glu Ala Ala
1               5                   10

<210> SEQ ID NO 12
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 12

Gly Ala Gln Phe Ser Lys Thr Ala Ala Lys Gly Glu Ala
1               5                   10

<210> SEQ ID NO 13
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 13

Gly Ala Gln Phe Ser Lys Thr Ala Ala Lys Gly Glu
1               5                   10

<210> SEQ ID NO 14
<211> LENGTH: 11
<212> TYPE: PRT
```

```
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 14

Gly Ala Gln Phe Ser Lys Thr Ala Ala Lys Gly
1               5                   10

<210> SEQ ID NO 15
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 15

Gly Ala Gln Phe Ser Lys Thr Ala Ala Lys
1               5                   10

<210> SEQ ID NO 16
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 16

Gly Ala Gln Phe Ser Lys Thr Ala Ala
1               5

<210> SEQ ID NO 17
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 17

Gly Ala Gln Phe Ser Lys Thr Ala
1               5

<210> SEQ ID NO 18
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 18

Gly Ala Gln Phe Ser Lys Thr
1               5

<210> SEQ ID NO 19
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety
```

<400> SEQUENCE: 19

Gly Ala Gln Phe Ser Lys
1               5

<210> SEQ ID NO 20
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 20

Gly Ala Gln Phe Ser
1               5

<210> SEQ ID NO 21
<211> LENGTH: 1885
<212> TYPE: DNA
<213> ORGANISM: Homo sapiens
<220> FEATURE:
<221> NAME/KEY: CDS
<222> LOCATION: (309)..(1307)

<400> SEQUENCE: 21

```
tttattactt cttttttttt cgaactacac ttgggctcct ttttttgtgc tcgacttttc      60 caccctttt ccctccctcc tgtgctgctg cttttgatc tcttcgacta aattttttt       120 atccggagtg tatttaatcg gttctgttct gtcctctcca ccaccccac ccccctccct     180 ccggtgtgtg tgccgctgcc gctgttgccg ccgccgctgc tgctgctgct cgccccgtcg    240
ttacaccaac ccgaggctct tgtttcccc tcttggatct gttgagtttc tttgttgaag    300 aagccagc atg ggt gcc cag ttc tcc aag acc gca gcg aag gga gaa gcc    350
         Met Gly Ala Gln Phe Ser Lys Thr Ala Ala Lys Gly Glu Ala
             1               5                   10 gcc gcg gag agg cct ggg gag gcg gct gtg gcc tcg tcg cct tcc aaa    398
Ala Ala Glu Arg Pro Gly Glu Ala Ala Val Ala Ser Ser Pro Ser Lys
15                  20                  25                  30 gcg aac gga cag gag aat ggc cac gtg aag gta aac ggc gac gct tcg    446
Ala Asn Gly Gln Glu Asn Gly His Val Lys Val Asn Gly Asp Ala Ser
                35                  40                  45 ccc gcg gcc gcc gag tcg ggc gcc aag gag gag ctg cag gcc aac ggc    494
Pro Ala Ala Ala Glu Ser Gly Ala Lys Glu Glu Leu Gln Ala Asn Gly
    50                  55                  60 agc gcc ccg gcc gcc gac aag gag gag ccc gcg gcc gcc ggg agc ggg    542
Ser Ala Pro Ala Ala Asp Lys Glu Glu Pro Ala Ala Ala Gly Ser Gly
65                  70                  75 gcg gcg tcg ccc tcc gcg gcc gag aaa ggt gag ccg gcc gcc gcc gct    590
Ala Ala Ser Pro Ser Ala Ala Glu Lys Gly Glu Pro Ala Ala Ala Ala
    80                  85                  90 gcc ccc gag gcc ggg gcc agc ccg gta gag aag gag gcc ccc gcg gaa    638
Ala Pro Glu Ala Gly Ala Ser Pro Val Glu Lys Glu Ala Pro Ala Glu
95                  100                 105                 110 ggc gag gct gcc gag ccc ggc tcg ccc acg gcc gcg gag gga gag gcc    686
Gly Glu Ala Ala Glu Pro Gly Ser Pro Thr Ala Ala Glu Gly Glu Ala
                115                 120                 125 gcg tcg gcc gcc tcc tcg act tct tcg ccc aag gcc gag gac ggg gcc    734
Ala Ser Ala Ala Ser Ser Thr Ser Ser Pro Lys Ala Glu Asp Gly Ala
    130                 135                 140 acg ccc tcg ccc agc aac gag acc ccg aaa aaa aaa aag aag cgc ttt    782
Thr Pro Ser Pro Ser Asn Glu Thr Pro Lys Lys Lys Lys Lys Arg Phe
```

```
                    145                 150                   155
tcc ttc aag aag tct ttc aag ctg agc ggc ttc tcc ttc aag aag aac     830
Ser Phe Lys Lys Ser Phe Lys Leu Ser Gly Phe Ser Phe Lys Lys Asn
    160                 165                 170 aag aag gag gct gga gaa ggc ggt gag gct gag gcg ccc gct gcc gaa     878
Lys Lys Glu Ala Gly Glu Gly Glu Ala Glu Ala Pro Ala Ala Glu
175                 180                 185                 190 ggc ggc aag gac gag gcc gcc ggg ggc gca gct gcg gcc gcc gag         926
Gly Gly Lys Asp Glu Ala Ala Gly Gly Ala Ala Ala Ala Ala Glu
                195                 200                 205 gcg ggc gcg gcc tcc ggg gag cag gca gcg gcg ccg ggc gag gag gca     974
Ala Gly Ala Ala Ser Gly Glu Gln Ala Ala Pro Gly Glu Glu Ala
            210                 215                 220 gca gcg ggc gag gag ggg gcg gcg ggt ggc gac tcg cag gag gcc aag    1022
Ala Ala Gly Glu Glu Gly Ala Ala Gly Gly Asp Ser Gln Glu Ala Lys
        225                 230                 235 ccc cag gag gcc gct gtc gcg cca gag aag ccg ccc gcc agc gac gag    1070
Pro Gln Glu Ala Ala Val Ala Pro Glu Lys Pro Pro Ala Ser Asp Glu
    240                 245                 250 acc aag gcc gcc gag gag ccc agc aag gtg gag gag aaa aag gcc gag    1118
Thr Lys Ala Ala Glu Glu Pro Ser Lys Val Glu Glu Lys Lys Ala Glu
255                 260                 265                 270 gag gcc ggg gcc agc gcc gcc gcc tgc gag gcc ccc tcc gcc gcc ggg    1166
Glu Ala Gly Ala Ser Ala Ala Ala Cys Glu Ala Pro Ser Ala Ala Gly
                275                 280                 285 ctg gtg tgc ccc cgg aga gga ggc agc ccc cgc gga gga gcc cgc ggc    1214
Leu Val Cys Pro Arg Arg Gly Gly Ser Pro Arg Gly Gly Ala Arg Gly
            290                 295                 300 cgc cgc agc ctc aat caa gcc tgc gca gcc ccc tca cag gag gcc cag    1262
Arg Arg Ser Leu Asn Gln Ala Cys Ala Ala Pro Ser Gln Glu Ala Gln
        305                 310                 315 ccc gag tgc agt cca gaa gcc ccc cca gcg gag gcg gca gag taa        1307
Pro Glu Cys Ser Pro Glu Ala Pro Pro Ala Glu Ala Ala Glu
    320                 325                 330 aagagcaagc ttttgtgaga taatcgaaga acatttctc ccccgtttgt ttggttggag   1367
tggtgccagg tactggattt tggagaactt gtctacaacc agggattgat tttaaagatg  1427
tcttttttta ttttactttt tttaagcac caaattttgt tgttttttt ttctcccctc   1487
cccacagatc ccatctcaaa tcattctgtt aaccaccatt ccaacaggtc gaggagagct  1547
taaacacctt cttcctctgg ccttgtttct cttttatttt ttattttttc gcatcagtat  1607
taatgttttt gcatactttg catctttatt caaaagtgta aactttcttt gtcaatctat  1667
ggacatgccc atatatgaag gagatgggtg ggtcaaaaag ggatatcaaa tgaagtgata  1727
ggggtcacaa tggggaaatt gaagtggtgc ataacattgc caaaatagtg tgccactaga  1787
aatggtgtaa aggctgtctt ttttttttt tttaaagaaa agttattacc atgtattttg   1847
tgaggcaggt ttacaacact acaactcgtg ccgaattc                         1885

<210> SEQ ID NO 22
<211> LENGTH: 332
<212> TYPE: PRT
<213> ORGANISM: Homo sapiens

<400> SEQUENCE: 22

Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30
```

```
Gly Gln Glu Asn Gly His Val Lys Val Asn Gly Asp Ala Ser Pro Ala
             35                  40                  45

Ala Ala Glu Ser Gly Ala Lys Glu Glu Leu Gln Ala Asn Gly Ser Ala
 50                  55                  60

Pro Ala Ala Asp Lys Glu Glu Pro Ala Ala Gly Ser Gly Ala Ala
 65                  70                  75                  80

Ser Pro Ser Ala Ala Glu Lys Gly Glu Pro Ala Ala Ala Ala Pro
                 85                  90                  95

Glu Ala Gly Ala Ser Pro Val Glu Lys Glu Ala Pro Ala Glu Gly Glu
                100                 105                 110

Ala Ala Glu Pro Gly Ser Pro Thr Ala Ala Glu Gly Glu Ala Ala Ser
            115                 120                 125

Ala Ala Ser Ser Thr Ser Ser Pro Lys Ala Glu Asp Gly Ala Thr Pro
130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190

Lys Asp Glu Ala Ala Gly Gly Ala Ala Ala Ala Ala Glu Ala Gly
            195                 200                 205

Ala Ala Ser Gly Glu Gln Ala Ala Ala Pro Gly Glu Glu Ala Ala Ala
210                 215                 220

Gly Glu Glu Gly Ala Ala Gly Gly Asp Ser Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Ala Gly Leu Val
            275                 280                 285

Cys Pro Arg Arg Gly Gly Ser Pro Arg Gly Gly Ala Arg Gly Arg Arg
290                 295                 300

Ser Leu Asn Gln Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330

<210> SEQ ID NO 23
<211> LENGTH: 2589
<212> TYPE: DNA
<213> ORGANISM: Homo sapiens
<220> FEATURE:
<221> NAME/KEY: CDS
<222> LOCATION: (370)..(1368)

<400> SEQUENCE: 23
caaccaggga gatttctcca ttttcctctt gtctacagtg cggctacaaa tctgggattt      60
ttttattact tcttttttt  tcgaactaca cttgggctcc ttttttttgtg ctcgactttt     120 ccaccctttt tccctccctc ctgtgctgct gcttttttgat ctcttcgact aaaattttt     180 tatccggagt gtatttaatc ggttctgttc tgtcctctcc accacccca ccccctccc     240 tccggtgtgt gtgccgctgc cgctgttgcc gccgccgctg ctgctgctgc tcgcccgtc     300 gttacaccaa cccgaggctc tttgtttccc ctcttggatc tgttgagttt ctttgttgaa    360
```

```
gaagccagc atg ggt gcc cag ttc tcc aag acc gca gcg aag gga gaa gcc    411
          Met Gly Ala Gln Phe Ser Lys Thr Ala Ala Lys Gly Glu Ala
            1               5                  10 gcc gcg gag agg cct ggg gag gcg gct gtg gcc tcg tcg cct tcc aaa      459
Ala Ala Glu Arg Pro Gly Glu Ala Ala Val Ala Ser Ser Pro Ser Lys
 15              20                  25                  30 gcg aac gga cag gag aat ggc cac gtg aag gta aac ggc gac gct tcg      507
Ala Asn Gly Gln Glu Asn Gly His Val Lys Val Asn Gly Asp Ala Ser
                 35                  40                  45 ccc gcg gcc gcc gag tcg ggc gcc aag gag gag ctg cag gcc aac ggc      555
Pro Ala Ala Ala Glu Ser Gly Ala Lys Glu Glu Leu Gln Ala Asn Gly
             50                  55                  60 agc gcc ccg gcc gcc gac aag gag gag ccc gcg gcc gcc ggg agc ggg      603
Ser Ala Pro Ala Ala Asp Lys Glu Glu Pro Ala Ala Ala Gly Ser Gly
         65                  70                  75 gcg gcg tcg ccc tcc tcg gcc gag aaa ggt gag ccg gcc gcc gcc gct      651
Ala Ala Ser Pro Ser Ser Ala Glu Lys Gly Glu Pro Ala Ala Ala Ala
     80                  85                  90 gcc ccc gag gcc ggg gcc agc ccg gta gag aag gag gcc ccc gcg gaa      699
Ala Pro Glu Ala Gly Ala Ser Pro Val Glu Lys Glu Ala Pro Ala Glu
 95                 100                 105                 110 ggc gag gct gcc gag ccc ggc tcg gcc acg gcc gcg gag gga gag gcc      747
Gly Glu Ala Ala Glu Pro Gly Ser Ala Thr Ala Ala Glu Gly Glu Ala
                115                 120                 125 gcg tcg gcc gcc tcc tcg act tct tcg ccc aag gcc gag gac ggg gcc      795
Ala Ser Ala Ala Ser Ser Thr Ser Ser Pro Lys Ala Glu Asp Gly Ala
            130                 135                 140 acg ccc tcg ccc agc aac gag acc ccg aaa aaa aaa aag aag cgc ttt      843
Thr Pro Ser Pro Ser Asn Glu Thr Pro Lys Lys Lys Lys Arg Phe
        145                 150                 155 tcc ttc aag aag tct ttc aag ctg agc ggc ttc tcc ttc aag aag aac      891
Ser Phe Lys Lys Ser Phe Lys Leu Ser Gly Phe Ser Phe Lys Lys Asn
    160                 165                 170 aag aag gag gct gga gaa ggc ggt gag gct gag gcg ccc gct gcc gaa      939
Lys Lys Glu Ala Gly Glu Gly Gly Glu Ala Glu Ala Pro Ala Ala Glu
175                 180                 185                 190 ggc ggc aag gac gag gcc gcc ggg ggc gca gct gcg gcc gcc gcc gag      987
Gly Gly Lys Asp Glu Ala Ala Gly Gly Ala Ala Ala Ala Ala Ala Glu
                195                 200                 205 gcg ggc gcg gcc tcc ggg gag cag gca gcg gcg ccg ggc gag gag gcg     1035
Ala Gly Ala Ala Ser Gly Glu Gln Ala Ala Ala Pro Gly Glu Glu Ala
            210                 215                 220 gca gcg ggc gag gag ggg gcg gcg ggt ggc gac ccg cag gag gcc aag     1083
Ala Ala Gly Glu Glu Gly Ala Ala Gly Gly Asp Pro Gln Glu Ala Lys
        225                 230                 235 ccc cag gag gcc gct gtc gcg cca gag aag ccg ccc gcc agc gac gag     1131
Pro Gln Glu Ala Ala Val Ala Pro Glu Lys Pro Pro Ala Ser Asp Glu
    240                 245                 250 acc aag gcc gcc gag gag ccc agc aag gtg gag gag aaa aag gcc gag     1179
Thr Lys Ala Ala Glu Glu Pro Ser Lys Val Glu Glu Lys Lys Ala Glu
255                 260                 265                 270 gag gcc ggg gcc agc gcc gcc gcc tgc gag gcc ccc tcc gcc gcc ggg     1227
Glu Ala Gly Ala Ser Ala Ala Ala Cys Glu Ala Pro Ser Ala Ala Gly
                275                 280                 285 ccc ggc gcg ccc ccg gag cag gag gca gcc ccc gcg gag gag ccc gcg     1275
Pro Gly Ala Pro Pro Glu Gln Glu Ala Ala Pro Ala Glu Glu Pro Ala
            290                 295                 300 gcc gcc gca gcc tcg tca gcc tgc gca gcc ccc tca cag gag gcc cag     1323
Ala Ala Ala Ala Ser Ser Ala Cys Ala Ala Pro Ser Gln Glu Ala Gln
        305                 310                 315
```

```
ccc gag tgc agt cca gaa gcc ccc cca gcg gag gcg gca gag taa        1368
Pro Glu Cys Ser Pro Glu Ala Pro Pro Ala Glu Ala Ala Glu
    320                 325                 330 aagagcaagc ttttgtgaga taatcgaaga actttctcc cccgtttgtt tgttggagtg   1428
gtgccaggta ctgttttgga gaacttgtct acaaccaggg attgatttta aagatgtctt   1488
ttttattt   acttttttt   aagcaccaaa ttttgttgtt tttttttttc tccctcccc   1548
acagatccca tctcaaatca ttctgttaac caccattcca acaggtcgag gagagcttaa   1608
acaccttctt cctctgcctt gtttctcttt tatttttat ttttcgcat cagtattaat    1668
gtttttgcat actttgcatc tttattcaaa agtgtaaact ttctttgtca atctatggac   1728
atgcccatat atgaaggaga tgggtgggtc aaaaagggat atcaaatgaa gtgataggg    1788
tcacaatggg gaaattgaag tggtgcataa cattgccaaa atagtgtgcc actagaaatg   1848
gtgtaaaggc tgtcttttt ttttttttta agaaaagtt attaccatgt attttgtgag    1908
gcaggtttac aacactacaa gtcttgagtt aagaaggaaa gaggaaaaaa gaaaaaacac   1968
caatacccag atttaaaaaa aaaaaaacga tcatagtctt aggagttcat ttaaaccata   2028
ggaactttc acttatctca tgttagctgt accagtcagt gattaagtag aactacaagt   2088
tgtataggct ttattgttta ttgctggttt atgaccttaa taaagtgtaa ttatgtatta   2148
ccagcagggt gttttaact gtgactattg tataaaaaca aatcttgata tccagaagca    2208
catgaagttt gcaactttcc accctgccca tttttgtaaa actgcagtca tcttggacct   2268
tttaaaacac aaattttaaa ctcaaccaag ctgtgataag tggaatggtt actgtttata   2328
ctgtggtatg ttttgatta cagcagataa tgctttcttt tccagtcgtc tttgagaata   2388
aaggaaaaa aatcttcaga tgcaatggtt ttgtgtagca tcttgtctat catgttttgt   2448
aaatactgga gaagctttga ccaattgac ttagagatgg aatgtaactt tgcttacaaa    2508
aattgctatt aaactcctgc ttaaggtgtt ctaattttct gtgagcacac taaaagcgaa   2568
aaataaatgt gaataaaatg t                                             2589
```

<210> SEQ ID NO 24
<211> LENGTH: 332
<212> TYPE: PRT
<213> ORGANISM: Homo sapiens

<400> SEQUENCE: 24

Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Gly Ser Gly Ala Ala
65                  70                  75                  80

Ser Pro Ser Ser Ala Glu Lys Gly Glu Pro Ala Ala Ala Ala Pro
                85                  90                  95

Glu Ala Gly Ala Ser Pro Val Glu Lys Glu Ala Pro Ala Glu Gly Glu
            100                 105                 110

Ala Ala Glu Pro Gly Ser Ala Thr Ala Ala Glu Gly Glu Ala Ala Ser
        115                 120                 125

Ala Ala Ser Ser Thr Ser Ser Pro Lys Ala Glu Asp Gly Ala Thr Pro
    130                 135                 140

```
Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
            165                 170                 175

Glu Ala Gly Glu Gly Gly Glu Ala Glu Ala Pro Ala Ala Glu Gly Gly
        180                 185                 190

Lys Asp Glu Ala Ala Gly Gly Ala Ala Ala Ala Ala Glu Ala Gly
        195                 200                 205

Ala Ala Ser Gly Glu Gln Ala Ala Ala Pro Gly Glu Glu Ala Ala Ala
        210                 215                 220

Gly Glu Glu Gly Ala Ala Gly Gly Asp Pro Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
                260                 265                 270

Gly Ala Ser Ala Ala Cys Glu Ala Pro Ser Ala Ala Gly Pro Gly
        275                 280                 285

Ala Pro Pro Glu Gln Glu Ala Ala Pro Ala Glu Pro Ala Ala Ala
        290                 295                 300

Ala Ala Ser Ser Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330

<210> SEQ ID NO 25
<211> LENGTH: 25
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 25

Lys Lys Lys Lys Lys Arg Phe Ser Phe Lys Lys Ser Phe Lys Leu Ser
1               5                   10                  15

Gly Phe Ser Phe Lys Lys Asn Lys Lys
            20                  25

<210> SEQ ID NO 26
<211> LENGTH: 24
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Peptide may have an N-terminal myristate moiety

<400> SEQUENCE: 26

Gly Thr Ala Pro Ala Ala Glu Gly Ala Gly Glu Val Lys Arg Ala
1               5                   10                  15

Ser Ala Glu Ala Lys Gln Ala Phe
            20
```